United States Patent
Mutharasan et al.

(10) Patent No.: US 8,171,795 B1
(45) Date of Patent: May 8, 2012

(54) SELF-EXCITING, SELF-SENSING PIEZOELECTRIC CANTILEVER SENSOR FOR DETECTION OF AIRBORNE ANALYTES DIRECTLY IN AIR

(75) Inventors: Rajakkannu Mutharasan, West Chester, PA (US); David L. deLesdernier, Kennett Square, PA (US); Gossett Augustus Campbell, Gilbertsville, PA (US); David R. Maraldo, Gilbertsville, PA (US); Peter A. Nagy, Newtown Square, PA (US)

(73) Assignee: Drexel University, Philadelphia, PA (US)

( * ) Notice: Subject to any disclaimer, the term of this patent is extended or adjusted under 35 U.S.C. 154(b) by 1344 days.

(21) Appl. No.: 11/747,183

(22) Filed: May 10, 2007

Related U.S. Application Data

(63) Continuation-in-part of application No. 11/625,919, filed on Jan. 23, 2007, now Pat. No. 7,942,056.

(60) Provisional application No. 60/761,172, filed on Jan. 23, 2006, provisional application No. 60/807,020, filed on Jul. 11, 2006, provisional application No. 60/746,951, filed on May 10, 2006.

(51) Int. Cl.
*G01H 1/00* (2006.01)
(52) U.S. Cl. .......................... 73/579; 73/61.75
(58) Field of Classification Search .................... 73/579, 73/617, 622, 642, 644
See application file for complete search history.

(56) References Cited

U.S. PATENT DOCUMENTS

| | | | | |
|---|---|---|---|---|
| 5,079,199 A | * | 1/1992 | Ochi et al. | 501/135 |
| 5,162,691 A | * | 11/1992 | Mariani et al. | 310/321 |
| 5,283,037 A | * | 2/1994 | Baer et al. | 422/82.01 |
| 5,631,514 A | | 5/1997 | Garcia et al. | |
| 5,719,324 A | * | 2/1998 | Thundat et al. | 73/24.01 |
| 5,742,377 A | * | 4/1998 | Minne et al. | 355/71 |
| 5,825,275 A | | 10/1998 | Wuttig et al. | |
| 5,883,705 A | * | 3/1999 | Minne et al. | 355/71 |

(Continued)

FOREIGN PATENT DOCUMENTS

EP 0 631 319 A1 12/1994
(Continued)

OTHER PUBLICATIONS

Zhou J. et al., "Zeolite-modified microcantilever gas sensor for indoor air quality control," Sensors and Actuators B, Oct. 1, 2003, 94(3), 337-342.

(Continued)

*Primary Examiner* — Samir M Shah
(74) *Attorney, Agent, or Firm* — Woodcock Washburn, LLP

(57) ABSTRACT

A method for detection of airborne biological agent using a piezoelectric cantilever sensor that includes a piezoelectric layer and a non-piezoelectric layer. A recognition entity is placed on one or both of the two layers. The antibody that recognizes and binds to the airborne species may be chemically immobilized on the cantilever sensor surface. In one embodiment, the cantilever sensor is attached to a base at only one end. In another embodiment, the sensor includes first and second bases and at least one of the piezoelectric layer and the non-piezoelectric layer is affixed to each of the first and second bases to form a piezoelectric cantilever beam sensor. In this embodiment, resonance is measured via stress on the piezoelectric layer and it has been demonstrated that such sensors are robust and exhibit excellent sensing characteristics in gaseous media with sufficient sensitivity to detect airborne species at relatively low concentrations.

27 Claims, 58 Drawing Sheets

U.S. PATENT DOCUMENTS

| | | | |
|---|---|---|---|
| 6,252,335 B1* | 6/2001 | Nilsson et al. | 310/328 |
| 6,289,717 B1* | 9/2001 | Thundat et al. | 73/23.2 |
| 6,336,366 B1* | 1/2002 | Thundat et al. | 73/514.34 |
| 6,545,273 B1* | 4/2003 | Singh et al. | 850/55 |
| 6,589,727 B1 | 7/2003 | Klenerman et al. | 435/4 |
| 6,813,815 B2* | 11/2004 | Namerikawa et al. | 29/25.35 |
| 7,061,166 B2* | 6/2006 | Kuniyasu | 310/365 |
| 7,066,004 B1 | 6/2006 | Kohler et al. | |
| 7,089,813 B2* | 8/2006 | Takeuchi et al. | 73/865 |
| 7,195,909 B2 | 3/2007 | Klenerman et al. | 435/287.2 |
| 7,262,546 B2* | 8/2007 | Namerikawa et al. | 310/366 |
| 7,263,874 B2 | 9/2007 | Fitch et al. | 73/54.25 |
| 7,329,536 B2* | 2/2008 | Zeng et al. | 435/287.2 |
| 7,458,265 B2* | 12/2008 | Shih et al. | 73/579 |
| 2002/0170290 A1 | 11/2002 | Bright et al. | |
| 2003/0194697 A1 | 10/2003 | Klenerman et al. | 435/5 |
| 2003/0224551 A1 | 12/2003 | Kim et al. | 438/49 |
| 2004/0112723 A1 | 6/2004 | Jung et al. | |
| 2005/0248235 A1* | 11/2005 | Namerikawa et al. | 310/328 |
| 2005/0277852 A1 | 12/2005 | Shih et al. | 600/587 |
| 2006/0053870 A1 | 3/2006 | Berndt | 73/61.75 |
| 2006/0123510 A1* | 6/2006 | Cunningham et al. | 73/580 |
| 2006/0228657 A1 | 10/2006 | Masters et al. | 430/954 |
| 2007/0089515 A1 | 4/2007 | Shih et al. | 73/579 |
| 2007/0089519 A1* | 4/2007 | Hao et al. | 73/649 |
| 2007/0169553 A1 | 7/2007 | Mutharasan et al. | |
| 2007/0218534 A1 | 9/2007 | Klenerman et al. | 435/173.7 |
| 2008/0035180 A1* | 2/2008 | Mutharasan et al. | 134/32 |

FOREIGN PATENT DOCUMENTS

| | | |
|---|---|---|
| EP | 1 536 227 A2 | 6/2005 |
| JP | 2000-321117 A | 11/2000 |
| JP | 2005-156526 A | 6/2005 |
| WO | WO 98/50773 A2 | 11/1998 |
| WO | WO 2005/043126 A2 | 5/2005 |
| WO | WO2005/043126 A3 | 5/2005 |
| WO | PCT/US2007/011402 | 5/2007 |

OTHER PUBLICATIONS

Yi Jeong W. et al., "In situ cell detection using piezoelectric lead zirconate titanate-stainless steel cantilevers," J Applied Physics, Jan. 1, 2003, 93(1), 619-625.

Campbell et al., "Detection of pathogen *Escherichia coli* O157:H7 using self-excited PZT-glass microcantilevers," Biosensors & Bioelectronics, Sep. 15, 2005, 21(3), 462-473.

Seung S. Lee, et al., "Self-excited piezoelectric cantilever oscillators," Transducers, 1995, 417-420.

U.S. Appl. No. 11/659,919, filed Jan. 23, 2007, Mutharasan, et al.

U.S. Appl. No. 11/747,183, filed May 10, 2007, Mutharasan, et al.

U.S. Appl. No. 60/746,951, filed May 10, 2006, Mutharasan, et al.

U.S. Appl. No. 60/761,172, filed Jan. 23, 2006, Mutharasan, et al.

U.S. Appl. No. 60/807,020, filed Jul. 11, 2006, Mutharasan, et al.

Campbell, G.A., et al., "Piezoelectric excited millimeter-sized cantilever (PEMC) sensor detects *Escherichia coli* O157:H7 in two-hour incubated samples at 4 CFU per gram of beef," J. of Rapid Methods and Automation in Mirobiology, no date available, 1-39.

Campbell, G.A., et al., "Detection and quantification of proteins using self-excited PZT-glass millimeter-sized cantilever," Biosensors and Bioelectronics, 2004, 26-45.

Campbell, G.A., et al., "Kinetics of *Bacillus anthracis* spore binding to antibody functionalized PEMC sensors in presence of *Bacillus thuringiensis* and *Bacillus cereus*," J. Publications, Am. Chem. Soc., 2006, 25 pages.

Campbell, G.A., et al., "*Escherichia coli* O157:H7 detection limit of millimeter-sized PZT cantilever sensors in 700 cells/mL," Analytical Sci., 2005, 11-25.

Campbell, G.A., "Detection of *Staphylococcus* enterotoxin B at pictogram levels using piezoelectric-excited millimeter-sized cantilever sensors," Submitted on-line to J. of Analytical Chem, 2006, 1-24.

Campbell, G.A., et al., "Detect *Escherichia coli* O157:H7 in ground beef samples using piezoelectric excited millimeter-sized cantilever (PEMC) sencors," Submitted on-line to Biosensors and Bioelectrionics, 2006, 2-34.

Campbell, G.A., et al., "A method for measuring *Escherichia coli* O157:H7 at 1 cell/mL in 1 liter sample using antibody functional piezoelectric-excited millimeter-sized cantilever sensor," Paper submitted on-line to J. of Analytical Chemistry, 2006, 1-23.

Campbell, G.A., et al., Detection of pathogen *Escherichia coli* O157:H7 using self-excited PZT-glass microcantilevers, Biosensors and Bioelectronics, 2004, 14-25.

Carr, D.W., et al., "Fabrication of nanoelectromechanical systems in single crystal silicon using silicon on insulator substrates and electron beam lithography," J. Vac. Sci. Technology, B, 1997, 15(6), 2760-2763.

Campbell, "Piezoelectric-excited millimeter-sized cantilever (PEMC) sensors detect *Bacillus anthraics* at 300 spores/mL", Department of Chemical Engineering Drexel University, Aug. 2, 2005, pp. 37-45.

Maraldo et al., "Resonant-mode millimeter-sized cantilever biosensor for continuous detection of proteins and pathogens in flowing liquids", Department of Chemistry and Biological Engineering, Drexel University, May 15, 2006, 21 pages.

Wilson et al., "Piezoelectric-excited millimeter-sized cantilever (PEMC) sensor provides viscosity and density measurements", Department of Chemical and Biological Engineering, Drexel University, Submitted to Review of Scientific Instruments, May 30, 2005, 26 pages.

\* cited by examiner

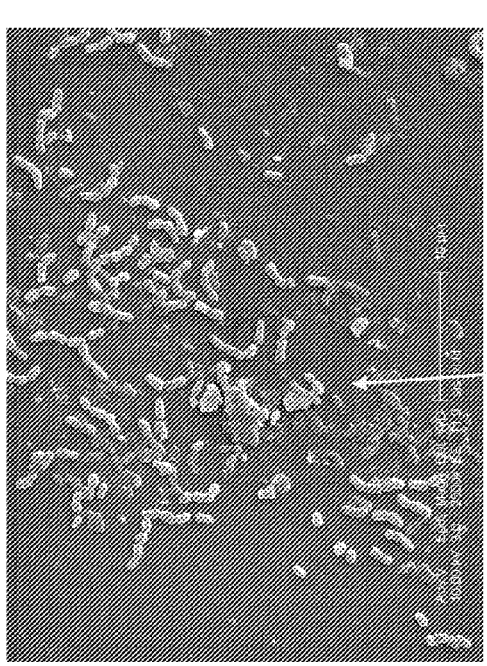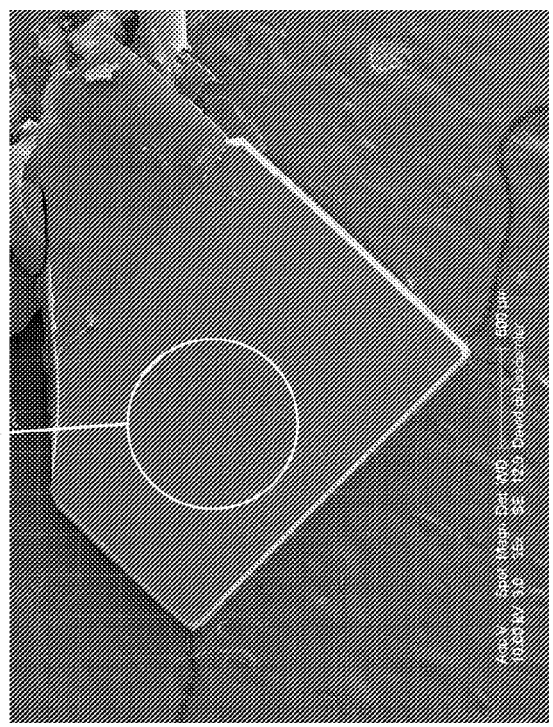
FIGURE 32

FIGURE 47

Table 1

Dimensions and Frequencies for overhang PEMC Devices
Corresponding to Figure 1A

| PEMC | PZT Type | Length (mm) a | b | c | Width a (mm) | Thickness (mm) | Resonant Frequency in Air (kHz) | | | | | |
|---|---|---|---|---|---|---|---|---|---|---|---|---|
| oPEMC#1 | Composite | 1.00 | 2.20 | 1.10 | 2.032 | 0.250 | 187.00 | 288.00 | ---- | 1001.30 | 1270.40 | 2841.00 | 4668.00 |
| oPEMC#2 | Composite | 1.40 | 1.90 | 3.00 | 2.032 | 0.250 | 143.97 | 200.29 | 857.35 | 988.77 | ---- | 2803.50 | 4562.00 |
| oPEMC#3 | Composite | 1.40 | 2.00 | 3.00 | 1.016 | 0.250 | 143.90 | ---- | 1814.80 | 1958.70 | ---- | ---- | ---- |
| oPEMC#4 | Ceramic | 1.00 | 1.50 | 0.20 | 1.016 | 0.4405 | 250.00 | 650.00 | 850.00 | 1650.00 | ---- | ---- | 4650.00 |
| oPEMC#5 | Ceramic | 0.60 | 0.90 | 0.80 | 1.016 | 0.4405 | 200.00 | ---- | 1000.00 | 1550.00 | 1900.00 | ---- | 4500.00 |

FIGURE 48

Table 2: Quality Factors of overhang PEMC Devices in Air

| overhang PEMC device | Quality factors in air | | | | | | |
|---|---|---|---|---|---|---|---|
| | Q1 | Q2 | Q3 | Q4 | Q5 | Q6 | Q7 |
| oPEMC#1 | 10 | 12 | ---- | 10 | 32 | 45 | 49 |
| oPEMC#2 | 24 | 11 | 66 | 27 | ---- | 56 | 24 |
| oPEMC#3 | 11 | ---- | 59 | 26 | ---- | ---- | ---- |
| oPEMC#4 | 3 | 13 | 17 | 11 | ---- | ---- | 23 |
| oPEMC#5 | 5 | ---- | 33 | 16 | 15 | ---- | 30 |

FIGURE 49

| PEMC Beam | Length (mm) | | Width (mm) | Thickness (mm) | | Resonant frequencies in air (Hz) | | | |
|---|---|---|---|---|---|---|---|---|---|
| | PZT | Glass | | PZT | Glass | f1 | f2 | f3 | f4 |
| aPEMCB#1 | 5 | 10 | 2 | 0.127 | 0.160 | 194,000 | 800,000 | 2,050,000 | ----- |
| aPEMCB#2 | 3 | 6 | 2 | 0.127 | 0.160 | 240,000 | 281,000 | 900,000 | 2,360,000 |
| fPEMCB#1 | 5 | 20 | 2 | 0.127 | 0.160 | 213,000 | 738,000 | 888,000 | 2,250,000 |
| fPEMCB#2 | 3 | 12 | 2 | 0.127 | 0.160 | 195,000 | 780,000 | ----- | 2,060,000 |
| abPEMCB#1 | 5 | 20 | 2 | 0.127 | 0.160 | 215,000 | 734,000 | 896,000 | ----- |
| abPEMCB#2 | 5 | 25 | 2 | 0.127 | 0.160 | 214,000 | 765,000 | ----- | 1,970,000 |
| oPEMCB#1 | 3 | 6 | 2 | 0.127 | 0.160 | 244,000 | ----- | ----- | 1,960,000 |

FIGURE 50

| PEMCB | Quality factors in air | | | | Quality factors in water | | | |
|---|---|---|---|---|---|---|---|---|
| | Q1 | Q2 | Q3 | Q4 | Q1 | Q2 | Q3 | Q4 |
| aPEMCB#1 | 20 | 10 | 10 | ----- | ----- | ----- | ----- | ----- |
| aPEMCB#2 | 34 | 40 | 10 | 12 | ----- | 25 | 10 | 6 |
| fPEMCB#1 | 22 | 29 | 20 | 10 | 18 | 22 | 10 | ----- |
| fPEMCB#2 | 26 | 10 | 17 | ----- | 19 | 22 | 10 | 10 |
| abPEMCB#1 | 22 | 25 | 15 | ----- | ----- | ----- | ----- | ----- |
| abPEMCB#2 | 25 | 20 | 12 | 17 | 21 | 15 | 10 | 8 |
| oPEMCB#1 | 25 | ----- | ----- | 16 | 20 | ----- | ----- | 10 |

SELF-EXCITING, SELF-SENSING PIEZOELECTRIC CANTILEVER SENSOR FOR DETECTION OF AIRBORNE ANALYTES DIRECTLY IN AIR

CROSS REFERENCE TO RELATED APPLICATIONS

The present application is a continuation in part application and claims priority to U.S. application Ser. No. 11/625,919, filed Jan. 23, 2007, entitled "Self-Exciting, Self-Sensing Piezoelectric Cantilever Sensor", which is hereby incorporated by reference in its entirety. U.S. application Ser. No. 11/625,919 claims priority to U.S. Provisional Patent Application No. 60/761,172, entitled "PIEZOELECTRIC CANTILEVER SENSORS," filed Jan. 23, 2006, and U.S. Provisional Patent Application No. 60/807,020, entitled "PIEZOELECTRIC CANTILEVER SENSORS," filed Jul. 11, 2006, both of which are hereby incorporated by reference in their entirety. The present application also claims priority to U.S. Provisional Patent Application No. 60/746,951, entitled "Detection of Airborne Pathogens Directly in Air," filed May 10, 2006, which is hereby incorporated by reference in its entirety.

TECHNICAL FIELD

The technical field generally relates to sensors, and more specifically relates to piezoelectric cantilever sensors and to detecting and measuring analytes utilizing a piezoelectric cantilever sensor.

BACKGROUND

Cantilever sensors can be broadly divided into two categories, depending upon dimensions of the sensor: micro-cantilevers and macro-cantilevers. Micro-cantilever sensors can be utilized in both static (bending) mode and dynamic (resonance) mode. In static mode, the deformation of the cantilever arm is measured to determine if an analyte (substance under analysis) is present. In dynamic mode, a resonance frequency is measured to determine if an analyte is present. Macro-cantilever sensors typically are not utilized in the static mode because bending of the cantilever arm is often limited. Macro-cantilever sensors can be utilized under liquid immersion conditions or in a gas or vacuum. Typically, greater sensitivity is achievable when a cantilever sensor is utilized in a gas/vacuum than in a liquid. Liquid dampening tends to adversely affect sensitivity. However, measuring analytes in liquid medium has many practical applications.

One type of known micro-cantilever sensor is a silicon-based micro-cantilever sensor. A typical silicon-based micro-cantilever sensor comprises a micro-cantilever that acts as a resonator. The micro-cantilever is driven by an external actuator at the base of the micro-cantilever to generate vibrations in the resonator. Typically, the vibrations are detected by an external optical detector. One disadvantage of typical silicon-based micro-cantilevers is the complex external optical components required for detection. Further, optical detection means disadvantageously limit application of the micro-cantilever sensor to optically clear samples. Another disadvantage is the weight and complexity added to the sensor due to the external actuator. Yet another disadvantage is that the external actuator can be located only at the base of the micro-cantilever, which limits its effectiveness in driving the cantilever's vibration. A further disadvantage of silicon-based micro-cantilever sensors is that they are mechanically fragile. Thus, silicon-based micro-cantilever sensors can not be used in high liquid flow rate environments. Further, typical silicon-based micro-cantilever sensors lose detection sensitivity in liquid media due to viscous damping.

Another type of known cantilever sensor is a quartz-based piezoelectric cantilever sensor. Quartz is a weak piezoelectric, and thus, much like silicon-based cantilever sensors, quartz-based piezoelectric cantilever sensors lose detection sensitivity in liquid media due to viscous damping. Further, the detection sensitivity of quartz-based sensors is limited by the planar geometry of the sensor.

Conventional piezoelectric cantilevers are known to be fabricated with a piezoelectric layer attached to a non-piezoelectric layer over part or the entire surface of the piezoelectric layer. In some conventional piezoelectric cantilevers, the piezoelectric layer is fixed at one end so that when the piezoelectric material is excited, the non-piezoelectric layer flexes to accommodate the strain caused in the piezoelectric material. When the frequency of excitation is the same as the natural frequency of the underlying mechanical structure, resonance occurs. This type of piezoelectric cantilever sensor is known to operate at frequencies lower than about 100 kHz at millimeter size. Currently, higher frequencies are obtainable only by making the cantilever sensor very short (less than 1.0 mm in length), very narrow (less than 0.1 mm in width), and very thin (less than 100 microns in thickness). However, reducing the dimensions of the cantilever sensor, particularly the width, thusly, makes the cantilever sensor less usable in a liquid medium due to viscous damping. Damping increases inversely with square of cantilever width.

Most current bio-sensing technologies rely on fluorescence, lasers, fiber-optics-based methods, quartz crystal microbalance technology, electrochemical enzyme immunoassays, and/or binding to metal particles. Most of these techniques are neither direct, nor quantitative. Many of these techniques are also quite slow. In addition, most of the aforementioned techniques do not lend themselves to measurement of changes in mass, which may provide a convenient way to measure a variety of different parameters.

A mass sensor based on resonance frequency requires three components, an actuator (driver), a resonator, and a detector. One example of a mass sensor is a silicon-based micro-cantilever, which can be easily integrated with existing silicon based methodologies. In a silicon-based micro-cantilever mass sensor, the micro-cantilever acts as the resonator and is driven by an external lead zirconate titanate (PZT) actuator at the base of the micro-cantilever to generate vibrations in the resonator, which may be detected by an external optical detector. For bio-detection, receptors are immobilized on the cantilever surface. Binding of antigens to the receptors immobilized on the cantilever surface increases the cantilever mass and causes a decrease in the resonance frequency. Detection of target molecules is achieved by monitoring the mechanical resonance frequency. In spite of the popularity of silicon-based micro-cantilevers, they rely on complex external optical components for detection. In addition, the PZT vibration driver adds to the weight and complexity of the sensor. Further, the external actuator can only be located at the base of the micro-cantilever, which greatly limits its effectiveness in driving the cantilever's vibration. The optical detection means also limits the application to optically clear samples.

In addition to mass detection, silicon-based micro-cantilevers have also been used as sensors for small molecules by detecting the stress generated on the cantilever by the adsorption of species onto receptors associated with the cantilever. Antibody or DNA receptors are coated on the surface of the micro-cantilevers to bind target biological molecules. The stress generated at the time of binding or unbinding of the target molecules to the receptors on the micro-cantilever surface induces a deflection of the micro-cantilever that may be detected by external optical components or by an adsorption-stress-induced DC voltage on a piezo-resistive coating layer on the cantilever surface.

Compared to silicon-based sensors, piezoelectric millimeter-sized cantilever sensors are not as bulky and complex. Piezoelectric devices are excellent transduction candidates because of their short response times and high piezoelectric coefficients. Because they are piezoelectric, both the driving and sensing of the mechanical resonance can be conveniently done electrically within the resonator. Currently, piezoelectric biosensors are based on commercially available quartz crystal microbalances (QCM), a disk device that uses thickness-mode resonance for sensing. Although quartz is a weak piezoelectric material, it is widely used as a layer thickness monitor in part due to the availability of large quartz single crystals to make the membranes. The typical mass detection sensitivity of a 5 MHz QCM that has a minimum detectable mass density (DMD) of $10^{-9}$ g/cm$^2$ is about $10^{-8}$ g/Hz, about four orders of magnitude less sensitive than millimeter sized piezoelectric cantilevers.

Microcantilevers exist that are about 100 microns length, a few tens of microns wide, and a few microns thick. Such microcantilevers are used in bending or in resonance mode for detection. The disadvantage of these microcantilevers is that their resonance characteristics are very strongly diminished due to viscous damping. Further, their use in liquid media has been accomplished at very low flow rates of microliters/min.

D. W. Carr and H. G. Craighead, "Fabrication of nanoelectromechanical systems in single crystal silicon using silicon on insulator substrates and electron beam lithography," *J. vac. Sci. Technology. B.*, 15(6), 1997. pp 2760-2763, discloses the fabrication of beam sensors and multiple beam sensors in a mesh configuration of the order of a few hundred nanometers, and have achieved high resonant frequencies of 40 MHz. Copending U.S. application Ser. No. 11/659,919, filed Jan. 23, 2007, entitled, "Self-Exciting, Self-Sensing Piezoelectric Cantilever Sensor" was co-invented by the present inventor and discusses the architecture and basic operation of millimeter sized piezoelectric-excited cantilever sensors in a liquid sample environment.

Therefore, there exists a need to improve the sensing capabilities of existing sensors and a need for the provision of sensors with an improved ability to perform detection of airborne species.

SUMMARY

A self-exciting and self-sensing piezoelectric cantilever sensing apparatus includes a piezoelectric layer and a non-piezoelectric layer attached to the piezoelectric layer such that a distal end of the non-piezoelectric layer extends beyond a distal end of the piezoelectric layer or a distal end of the piezoelectric layer extends beyond a distal end of the non-piezoelectric layer. That is, the piezoelectric layer is coupled to the non-piezoelectric layer such that the piezoelectric layer and the non-piezoelectric layer are not coextensive In various configurations of the piezoelectric cantilever sensing apparatus, the piezoelectric layer, the non-piezoelectric layer, or both are anchored to at least one base. Electrodes are operatively associated with the piezoelectric layer. The self-exciting, self-sensing piezoelectric cantilever sensor is utilized to sense mass change. To determine the mass of an analyte on the sensing apparatus, the resonance frequency of the mechanical member of the cantilever sensor is measured. The measured resonance frequency is compared with a baseline resonance frequency to determine a difference in frequency. The difference in frequency is indicative of a mass of an analyte on the sensing apparatus.

According to embodiments of the invention, detection of airborne pathogens in air, is accomplished without requiring sample collection in liquid or solid matrices. According to a one aspect, a method for airborne detection of target analytes, such as biological or chemical substance, is accomplished by exposing a sensing apparatus to the airborne analyte. A recognition entity, located on the sensing apparatus, binds to the analyte and is detectable while the analyte is present in a gas. Specific example recognition entities include chemical coatings for the detection of chemicals and immobilized antibodies for the detection of biologicals.

In one aspect of the invention, a sensing apparatus includes a sensor that includes a piezoelectric layer; a non-piezoelectric layer and a recognition entity located on either of the two layers. In a first embodiment, the sensor is a cantilever assembly that is fixed at only one end. Here, the piezoelectric layer is connected to a base and the non-piezoelectric layer is attached to the end of the piezoelectric layer in an overlap fashion. Electrodes are attached to the piezoelectric layer and are electrically driven to excite the piezoelectric layer to resonance. A recognition region on the non-piezoelectric layer attracts the analyte when exposed in a airflow and causes a change in mass of the cantilever that is formed by the combination of the piezoelectric and non-piezoelectric layers and the recognition area. The change in resonant frequency when the analyte is attached compared to a baseline resonant frequency is determined and the frequency shift is indicative of the amount of analyte held on the recognition entity.

The formation of the sensor may be changed to accommodate different frequency detection points. A second type of sensor involves the use of a beam type of sensor where the non-piezoelectric layer is attached to a base structure on both ends. The piezoelectric layer is placed on the non-piezoelectric layer and excited to resonance as mentioned above. A recognition entity on either of the non-piezoelectric or piezoelectric layers causes a mass change upon exposure to an aerosolized analyte and results in a frequency shift of the resonant frequency of the beam sensor. Thus, an analyte can be detected and its mass determined. A third type of sensor is a variation of the beam sensor where the piezoelectric layer is the beam and the non-piezoelectric layer is attached onto the top of the beam.

An apparatus to detect airborne analytes includes an exposure tube containing a cantilever sensor attached to a nebulizer which aerosolizes the analyte so that the analyte exists in an airflow across the sensor. An analyzer measures the resonant frequency of the sensor and determines if and how much of the analyte is present in the airflow.

These and various other advantages and features of novelty that characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a preferred embodiment of the invention.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

The foregoing summary, as well as the following detailed description, is better understood when read in conjunction with the appended drawings. For the purpose of illustrating a self-exciting, self-sensing piezoelectric cantilever sensor, there is shown in the drawings exemplary constructions thereof; however, a self-exciting, self-sensing piezoelectric cantilever sensor is not limited to the specific methods and instrumentalities disclosed. In the drawings:

FIG. 32 shows a scanning electron micrograph of a sensor tested in accordance with the method of the present invention showing anthrax spores immobilized on the surface of the sensor;

FIG. 47 includes Table 1;

FIG. 48 includes Table 2;

FIG. 49 includes Table 3; and

FIG. 50 includes Table 4.

DETAILED DESCRIPTION OF ILLUSTRATIVE EMBODIMENTS

Figure 1:
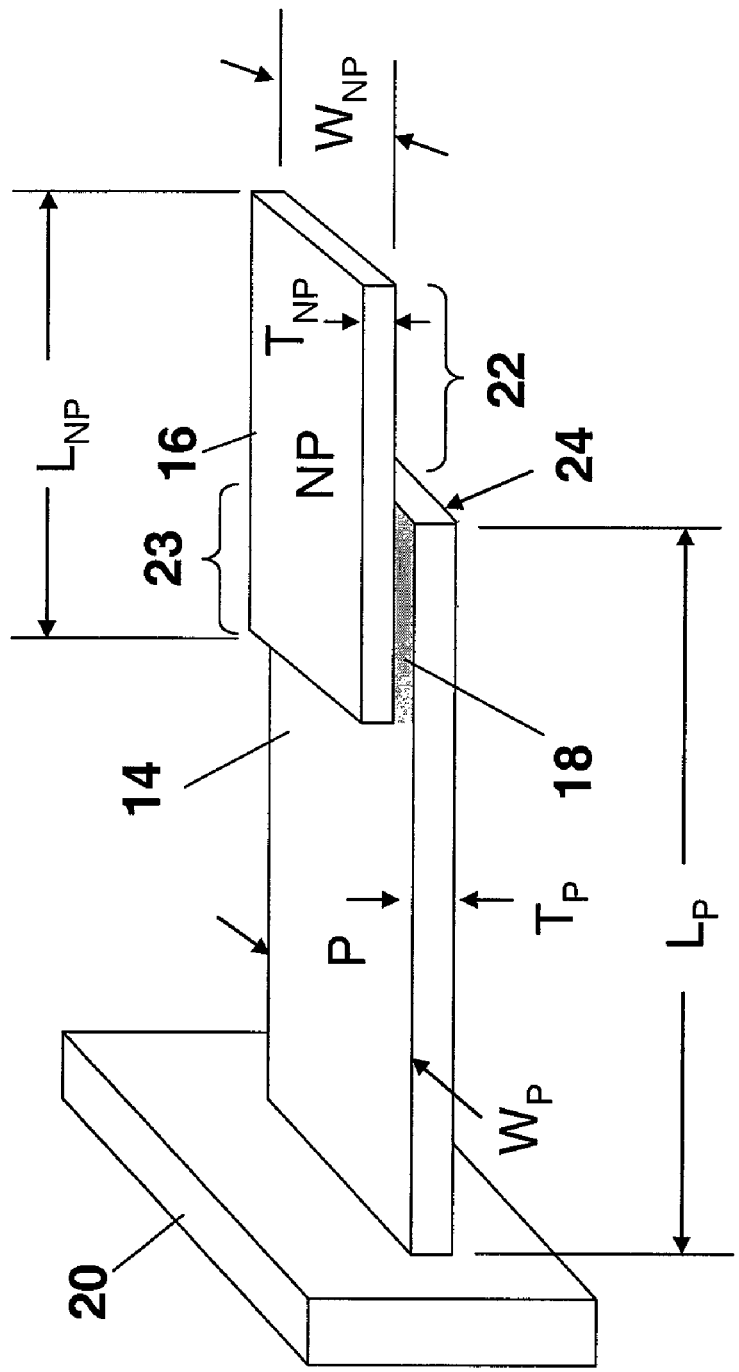
FIG. 1 is an illustration of an example configuration of a self-exciting, self-sensing piezoelectric cantilever sensor.

A self-exciting, self-sensing piezoelectric cantilever sensor as described herein provides the ability to detect and measure extremely small amounts of an analyte. The self-exciting, self-sensing piezoelectric cantilever sensor can be utilized to detect and measure an analyte immersed in a liquid and an analyte contained in a gas or vacuum. In various example configurations, the self-exciting, self-sensing piezoelectric cantilever sensor comprises at least one piezoelectric layer and at least one non-piezoelectric layer, wherein the piezoelectric layer is coupled to the non-piezoelectric layer such that the piezoelectric layer and the non-piezoelectric layer are not coextensive. The piezoelectric layer, the non-piezoelectric layer, or both can be coupled to at least one base. The piezoelectric layer and the non-piezoelectric layer can be of varying widths, lengths, and thicknesses.

The self-exciting, self-sensing piezoelectric cantilever sensor is utilizable to determine the mass of an analyte accumulated thereon. In an example embodiment, a portion of the self-exciting, self-sensing piezoelectric cantilever sensor is placed in a medium (e.g., liquid, gas, vacuum). While in the medium, a resonance frequency of the self-exciting, self-sensing piezoelectric cantilever sensor is measured and compared to a baseline resonance frequency. The difference in the measured resonance frequency and the baseline resonance frequency is indicative of an amount of mass of analyte accumulated (e.g., bound, adsorbed, absorbed) on the self-exciting, self-sensing piezoelectric cantilever sensor.

Analytes can be directly or indirectly bound to the surface of the non-piezoelectric portion of the self-exciting, self-sensing piezoelectric cantilever sensor. Binding of an analyte to the non-piezoelectric portion of the self-exciting, self-sensing piezoelectric cantilever sensor results in a change in mass of the self-exciting, self-sensing piezoelectric cantilever sensor, a change in stiffness of the self-exciting, self-sensing piezoelectric cantilever sensor, or a combination thereof. The changes in mass and/or stiffness are measurable as changes in resonance frequency, and can be monitored and measured by an appropriate analysis device, such as an operational amplifier, an impedance analyzer, a network analyzer, an oscillator circuit, or the like, for example. Resonance frequency changes, wherein at least a portion of the self-exciting, self-sensing piezoelectric cantilever sensor is immersed in a liquid, are detectable and measurable. Resonance frequency changes, wherein at least a portion of the self-exciting, self-sensing piezoelectric cantilever sensor is immersed in a gas or a vacuum, also are detectable and measurable.

The self-exciting, self-sensing piezoelectric cantilever sensor is operateable at high frequencies, such as, on the order of 0.1 MHz. to 6 MHz, for example. At these high frequencies, a Q factor (the ratio of the resonance peak frequency relative to the resonance peak width at half peak height), on the order of 10 to 100, under liquid immersion is obtainable. The self-exciting, self-sensing piezoelectric cantilever sensor is operateable at relative high frequencies in liquid media, gas media, and a vacuum. The self-exciting, self-sensing piezoelectric cantilever sensor thus provides extreme sensitivity to mass changes. The self-exciting, self-sensing piezoelectric cantilever sensor is especially suitable for analytes that are present at very low concentrations in media such as in body fluids, water, and food materials, for example.

The self-exciting, self-sensing piezoelectric cantilever sensor described herein provides the ability to detect changes in mass accumulated thereon as small as 100 attogram/Hz ($100 \times 10^{-18}$ grams/Hertz) or less when immersed in a liquid media. Thus, with respect to detecting changes in mass, the self-exciting, self-sensing piezoelectric cantilever sensor is approximately 1 million times more sensitive than a quartz crystal micro-cantilever sensor, approximate 100,000 times more sensitive than standard analytical instruments, and about 10,000 times more sensitive than conventional, three-layer piezoelectric cantilever designs.

The self-exciting, self-sensing piezoelectric cantilever sensor permits detection of extremely small concentrations of analyte that bind to the non-piezoelectric portion thereof. Utilizing the self-exciting, self-sensing piezoelectric cantilever sensor, pathogens and proteins are detectable at concentrations as low as a few pathogens/mL and, for proteins of average size (60 kilo-Daltons, kDa), at less than 1 pathogen/mL. Furthermore, any analyte that binds to an organic or inorganic functional group on the non-piezoelectric portion is detectable. The self-exciting, self-sensing piezoelectric cantilever sensor is operable in media having relatively high flow rates. The piezoelectric cantilevers sensors is operable in media having flow rates of 0.5 to 10.0 mL/minute, which is approximately 1000 times the flow rate used successfully with known bending mode micro-cantilevers.

Various example applications of the piezoelectric cantilever include the detection of bioterrorism agents, such as *Bacillus anthracis*, the detection of food-borne pathogens, such as *E. coli*, the detection of pathogens in food and water, the detection of certain cell types in body fluids (e.g., circulating tumor cells), the detection of biomarkers in body fluids (e.g., proteins that mark specific pathophysiology-alpha-fetoprotein, beta-2-microglobulin, bladder tumor antigen, breast cancer marker CA-15-3, and other CAs (cancer antigens), calcitonin, carcinoembryonic antigen, and others), the detection of markers of explosives such as trinitrotoluene, the presence of dinitrotoluene, and the detection of airborne and waterborne toxins. The self-exciting, self-sensing piezoelectric cantilever sensor also can be used for the detection of biological entities at picogram levels, and for the detection of protein-protein interactions, both steady state and kinetic.

Pathogens, such as E-coli for example, are detectable utilizing the self-exciting, self-sensing piezoelectric cantilever sensor. Detection of a model protein, lipoprotein, DNA, and/or RNA at a concentration 1.0 femtogram per mL ($10^{-15}$ grams) and pathogens at 1 pathogen/mL, respectively is achievable by measuring directly in liquid using the self-exciting, self-sensing piezoelectric cantilever sensor immobilized with antibodies specific to the target analyte at a frequency of about 1 to 2 MHz. The self-exciting, self-sensing piezoelectric cantilever sensor is capable of detecting a target analyte without false positives or negatives even when contaminating entities are present. The self-exciting, self-sensing piezoelectric cantilever sensor described herein is particularly advantageous when utilized with a raw sample, and no preparation, concentrating step, and/or enrichment of any type. Detection of an analyte utilizing the self-exciting, self-sensing piezoelectric cantilever sensor can be conducted directly in raw samples under flow conditions, such as 0.5 to 10.0 mL/minute for example. If clean samples are available, such as in a laboratory environment, detection at 1 femtogram/mL is achievable. This sensitivity is approximately 100 times more sensitive than the sensitivity associated with known optical techniques.

As described below, the sensitivity of the self-exciting, self-sensing piezoelectric cantilever sensor is due in part to the geometric design thereof. The relative lengths and widths of the piezoelectric and non-piezoelectric layers of the self-exciting, self-sensing piezoelectric cantilever sensor determine the sensitivity, and also the shape of the peak of the frequency spectrum provided by the self-exciting, self-sensing piezoelectric cantilever sensor. As described in more detail below, the self-exciting, self-sensing piezoelectric cantilever sensor comprises a piezoelectric layer and a non-piezoelectric layer coupled together such that a portion of the piezoelectric layer extends beyond the non-piezoelectric layer, or a portion of the non-piezoelectric layer extends beyond the piezoelectric layer, or a combination thereof. Thus, the piezoelectric layer and the non-piezoelectric layer are not coextensive. That is, the self-exciting, self-sensing piezoelectric cantilever sensor is configured such that an entire surface of the non-piezoelectric layer is not coupled to an entire surface of the piezoelectric layer.

The sensitivity of the self-exciting, self-sensing piezoelectric cantilever sensor is due in part to utilizing the piezoelectric layer of the cantilever sensor for both actuation and sensing and the electromechanical properties of the piezoelectric layer of the self-exciting, self-sensing piezoelectric cantilever sensor. At resonance, the oscillating cantilever concentrates stress in the piezoelectric layer toward a base portion of the self-exciting, self-sensing piezoelectric cantilever. This results in an amplified change in the resistive component of the piezoelectric layer, and a large shift in resonance frequency. Directing this stress to a portion of the piezoelectric layer having a low bending modulus (e.g., more flexible) allows for exploitation of the associated shift in resonance frequency to detect extremely small changes in mass of the self-exciting, self-sensing piezoelectric cantilever sensor. For example, if both the piezoelectric layer and the non-piezoelectric layer of a piezoelectric cantilever sensor are anchored at the same end (e.g., potted in epoxy), the sensor is less sensitive to changes in mass because the bending stress in the sensing piezoelectric layer proximal to the anchored end is lower compared to the case when only the piezoelectric layer is anchored. This is because the bending modulus of the two combined layers is higher than the case of anchoring the piezoelectric layer only. Bending modulus is the product of elastic modulus and moment of inertia about the neutral axis. And, moment of inertia is proportional to the cube power of thickness.

FIG. 1 is an illustration of a self-exciting, self-sensing piezoelectric cantilever sensor 12 comprising a piezoelectric portion 14 and a non-piezoelectric portion 16. Piezoelectric portions are labeled with an uppercase letter p ("P"), and non-piezoelectric portions are labeled with the uppercase letters np ("NP"). The self-exciting, self-sensing piezoelectric cantilever sensor 12 depicts an embodiment of an unanchored, overhang, self-exciting, self-sensing piezoelectric cantilever sensor. The self-exciting, self-sensing piezoelectric cantilever sensor 12 is termed "unanchored" because the non-piezoelectric layer 16 is not attached to the base portion 20. The self-exciting, self-sensing piezoelectric cantilever sensor 12 is termed, "overhang" because the non-piezoelectric layer 16 extends beyond the distal tip 24 of the piezoelectric layer 14 to create an overhanging portion 22 of the non-piezoelectric layer 16. The piezoelectric portion 14 is coupled to the non-piezoelectric portion 16 via adhesive portion 18. The piezoelectric portion 14 and the non-piezoelectric portion overlap at region 23. The adhesive portion 18 is positioned between the overlapping portions of the piezoelectric portion 14 and the non-piezoelectric portion 16. The piezoelectric portion 14 is coupled to a base portion 20.

The piezoelectric portion 14 can comprise any appropriate material such as lead zirconate titanate, lead magnesium niobate-lead titanate solid solutions, strontium lead titanate, quartz silica, piezoelectric ceramic lead zirconate and titanate (PZT), piezoceramic-polymer fiber composites, or the like, for example. The non-piezoelectric portion 16 can comprise any appropriate material such as glass, ceramics, metals, polymers and composites of one or more of ceramics, and polymers, such as silicon dioxide, copper, stainless steel, titanium, or the like, for example.

The self-exciting, self-sensing piezoelectric cantilever sensor can comprise portions having any appropriate combination of dimensions. Further, physical dimensions can be non-uniform. Thus, the piezoelectric layer and/or the non-piezoelectric layer can be tapered. For example, the length (e.g., $L_P$ in FIG. 1) of the piezoelectric portion (e.g., piezoelectric portion 14) can range from about 0.1 to about 10 mm. The length (e.g., $L_{NP}$ in FIG. 1) of the non-piezoelectric portion (e.g., non-piezoelectric portion 16) can range from about 0.1 to about 10 mm. The overlap region (e.g., overlap region 23) can range from about 0.1 to about 10 mm in length. The width (e.g., $W_P$ in FIG. 1) of the piezoelectric portion (e.g., piezoelectric portion 14), and the width (e.g., $W_{NP}$ in FIG. 1) of the non-piezoelectric portion (e.g., non-piezoelectric portion 16), can range from about 0.1 mm to about 4.0 mm. The width (e.g., $W_P$ in FIG. 1) of the piezoelectric portion can differ from the width (e.g., $W_{NP}$ in FIG. 1) of the non-piezoelectric portion as well. The thickness of the (e.g., $T_P$ in FIG. 1) of the piezoelectric portion (e.g., piezoelectric portion 14), and the thickness (e.g., $T_{NP}$ in FIG. 1) of the non-piezoelectric portion (e.g., non-piezoelectric portion 16), can range from about 0.1 mm to about 4.0 mm. The thickness (e.g., $T_P$ in FIG. 1) of the piezoelectric portion also can differ from the thickness (e.g., $T_{NP}$ in FIG. 1) of the non-piezoelectric portion.

Figure 2:
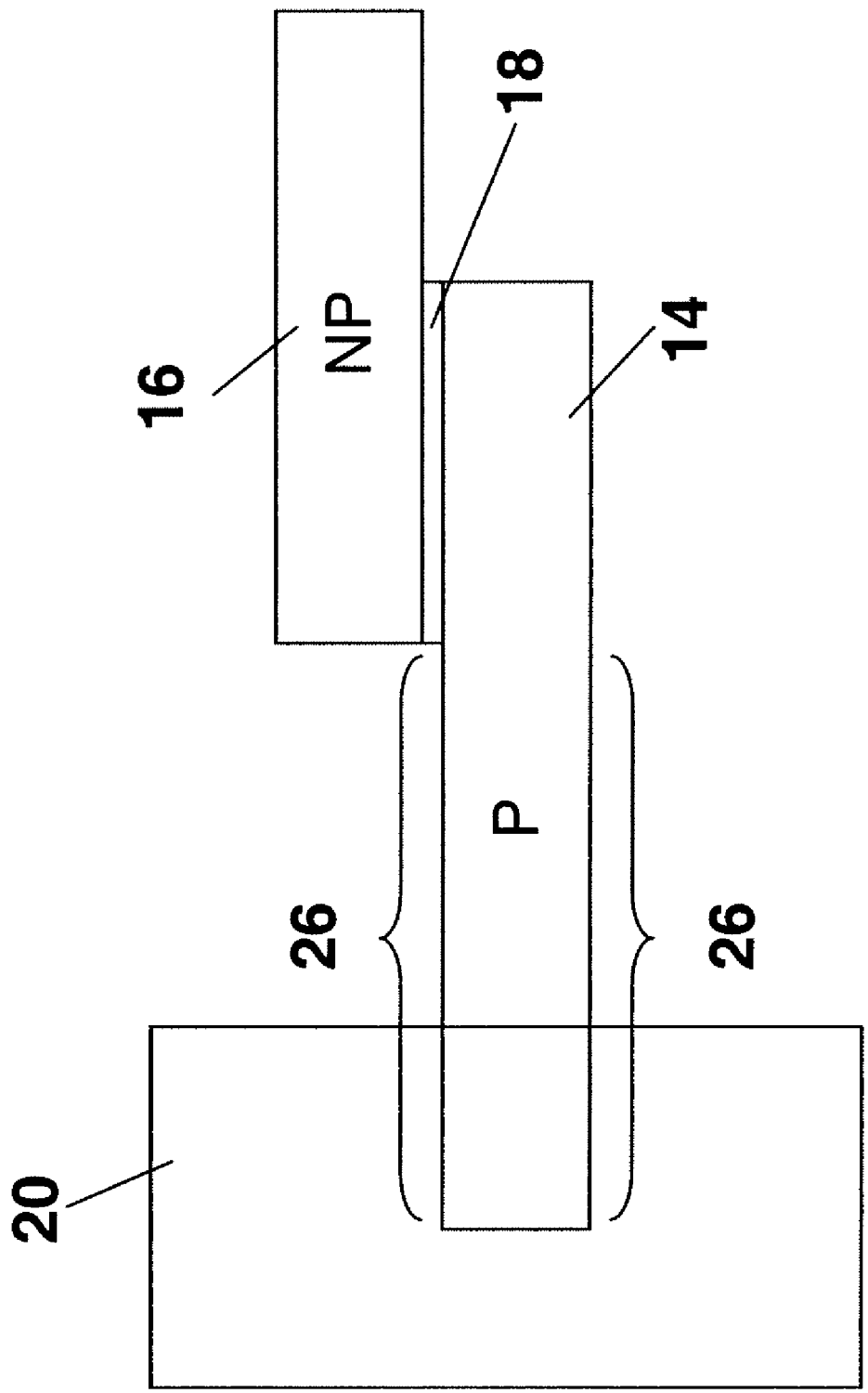
FIG. 2 is a cross-sectional view of an example self-exciting, self-sensing piezoelectric cantilever sensor depicting electrode placement regions for electrodes operationally associated with the piezoelectric layer.
Figure 3:
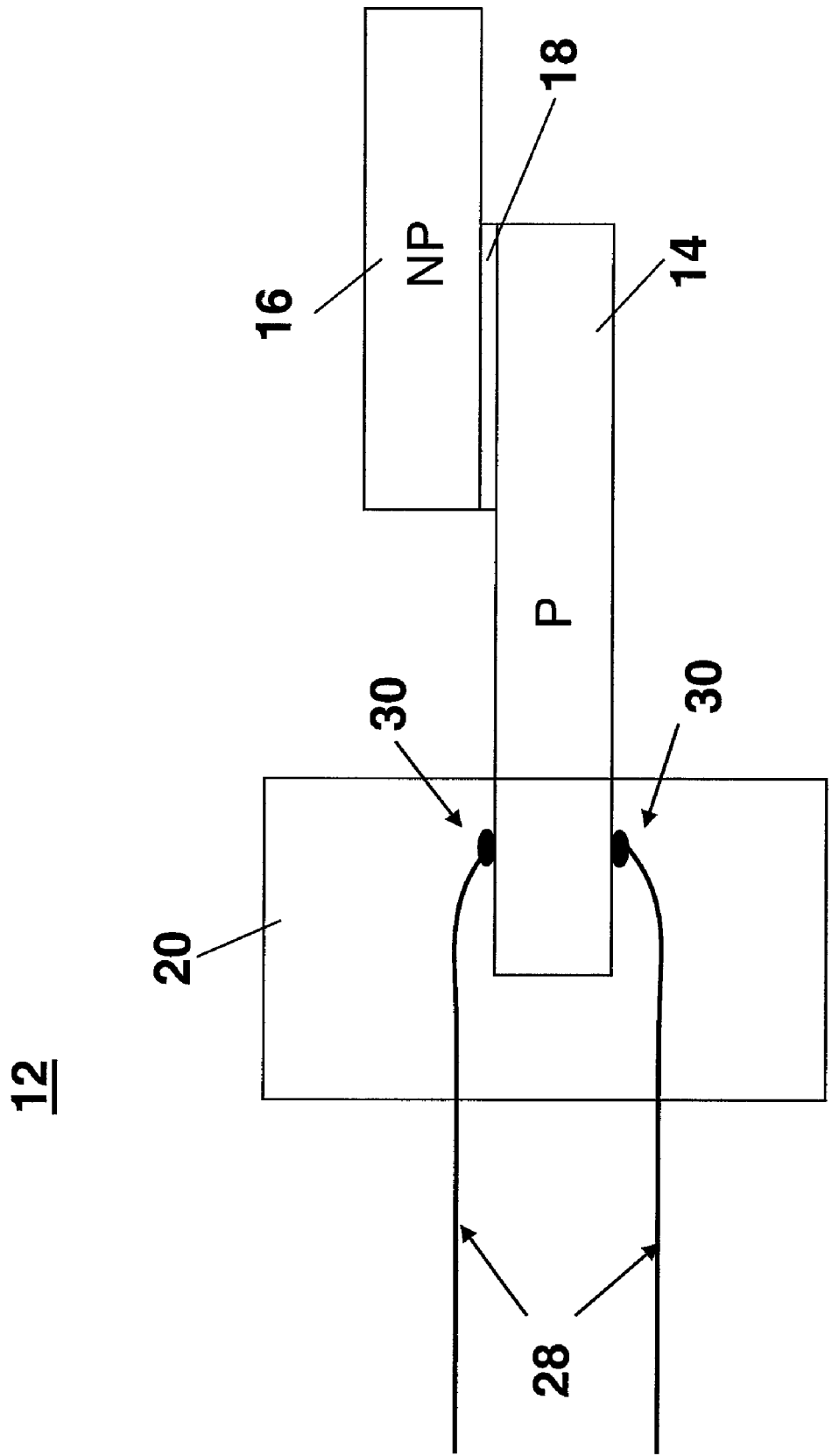
FIG. 3 is a cross-sectional view of an example self-exciting, self-sensing piezoelectric cantilever sensor showing depicting example electrode placement within a base portion of the self-exciting, self-sensing piezoelectric cantilever sensor.
Figure 4:
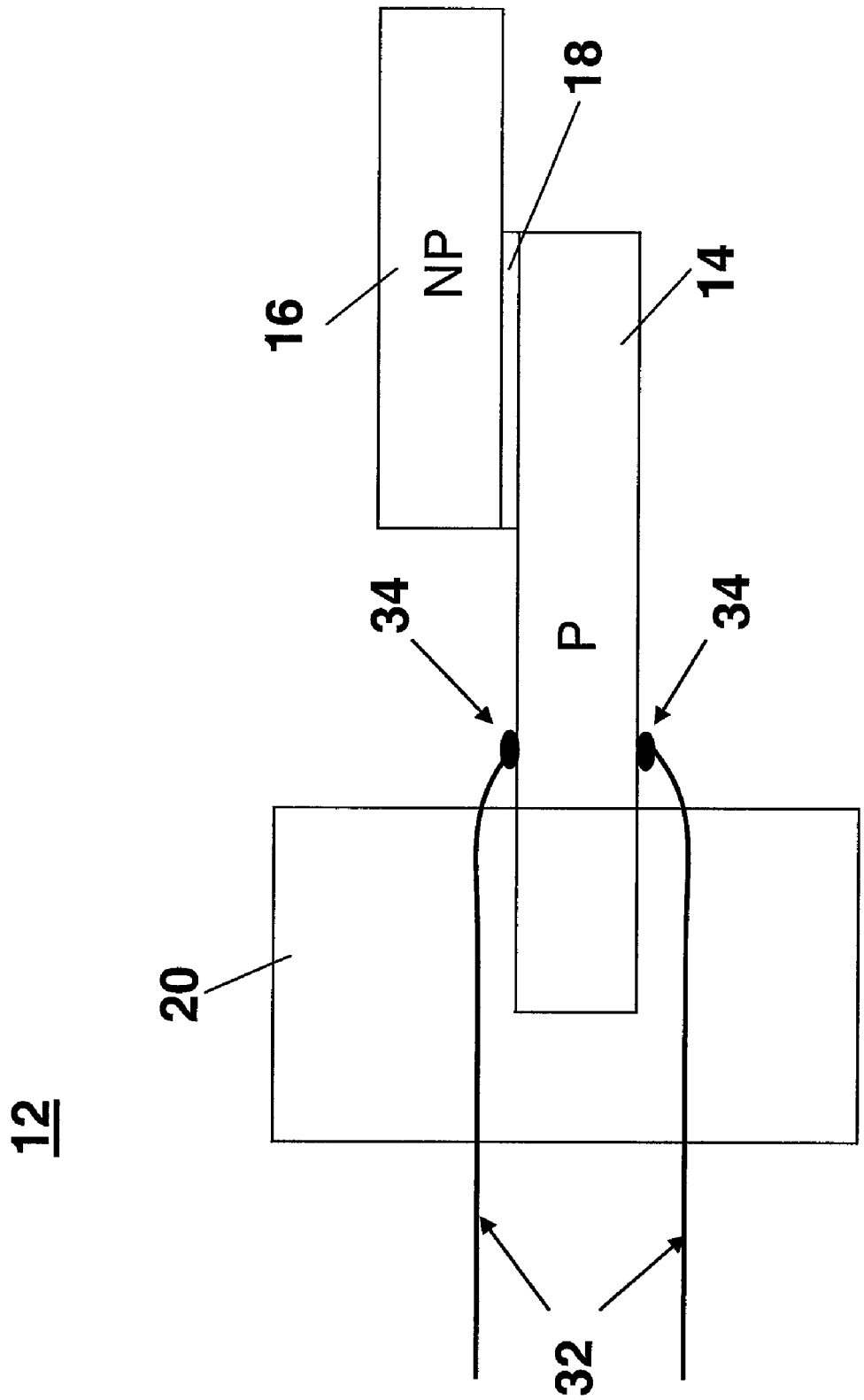
FIG. 4 is a cross-sectional view of an example self-exciting, self-sensing piezoelectric cantilever sensor showing depicting example electrode placement not within a base portion of the self-exciting, self-sensing piezoelectric cantilever sensor.

FIG. 2 is a cross-sectional view of the self-exciting, self-sensing piezoelectric cantilever sensor 12 depicting electrode placement regions 26 for electrodes operationally associated with the piezoelectric portion 14. Electrodes can be placed at any appropriate location on the piezoelectric portion of the self-exciting, self-sensing piezoelectric cantilever sensor as indicated by brackets 26. For example, as shown in FIG. 3, electrodes 28 can be coupled to the piezoelectric portion 14 within the base portion 20. Or, as depicted in FIG. 4, electrodes 32 can be coupled to the piezoelectric portion 14 at any location not within the base portion 20 and not overlapped by the non-piezoelectric portion 16. Electrodes need not be placed symmetrically about the piezoelectric portion 14. In an example embodiment, one electrode can be coupled to the piezoelectric portion 14 within the base portion 20 and the other electrode can be coupled to the piezoelectric portion 14 not within the base portion 20. Electrodes, or any appropriate means (e.g., inductive means, wireless means), can be utilized to provide an electrical signal to and receive an electrical signal from the piezoelectric portion 14. In an example embodiment, electrodes can be coupled to the piezoelectric portion 14 via a bonding pad or the like (depicted as elements 30 in FIG. 3 and elements 34 in FIG. 4). Example bonding pads can comprise any appropriate material (e.g., gold, silicon oxide) capable of immobilization of a receptor material and/or an absorbent material appropriate for use in chemical sensing or for bio-sensing.

Electrodes can be placed at any appropriate location. In an example embodiment, electrodes are operatively located near a location of concentrated stress in the piezoelectric layer 14. As described above, the sensitivity of the self-exciting, self-sensing piezoelectric cantilever sensor is due in part to advantageously directing (concentrating) the stress in the piezoelectric layer 14 and placing electrodes proximate thereto. The configurations of the self-exciting, self-sensing piezoelectric cantilever sensor described herein (and variants thereof) tend to concentrate oscillation associated stress in the piezoelectric layer 14. At resonance, in some of the configurations of the self-exciting, self-sensing piezoelectric cantilever sensor, the oscillating cantilever concentrates stress in the piezoelectric layer 14 toward the base portion 20. This results in an amplified change in the resistive component of the piezoelectric layer 14, and a large shift in resonance frequency at the locations of high stress. Directing this stress to a portion of the piezoelectric layer 14 having a low bending modulus (e.g., more flexible) allows for exploitation of the associated shift in resonance frequency to detect extremely small changes in mass of the self-exciting, self-sensing piezoelectric cantilever sensor. Thus, in example configurations of the self-exciting, self-sensing piezoelectric cantilever sensor, the thickness of the piezoelectric layer 14 located near the base portion 20 is thinner than portions of the piezoelectric layer 14 further away from the base portion 20. This tends to concentrate stress toward the thinner portion of the piezoelectric layer 14. In example configurations, electrodes are located at or near the locations of the oscillation associated concentrated stress near the base portion of the self-exciting, self-sensing piezoelectric cantilever sensor. In other example configurations of the self-exciting, self-sensing piezoelectric cantilever sensor electrodes are positioned proximate the location of concentrated stress in the piezoelectric layer regardless of the proximity of the concentrated stress to a base portion of the self-exciting, self-sensing piezoelectric cantilever sensor.

Figure 5:
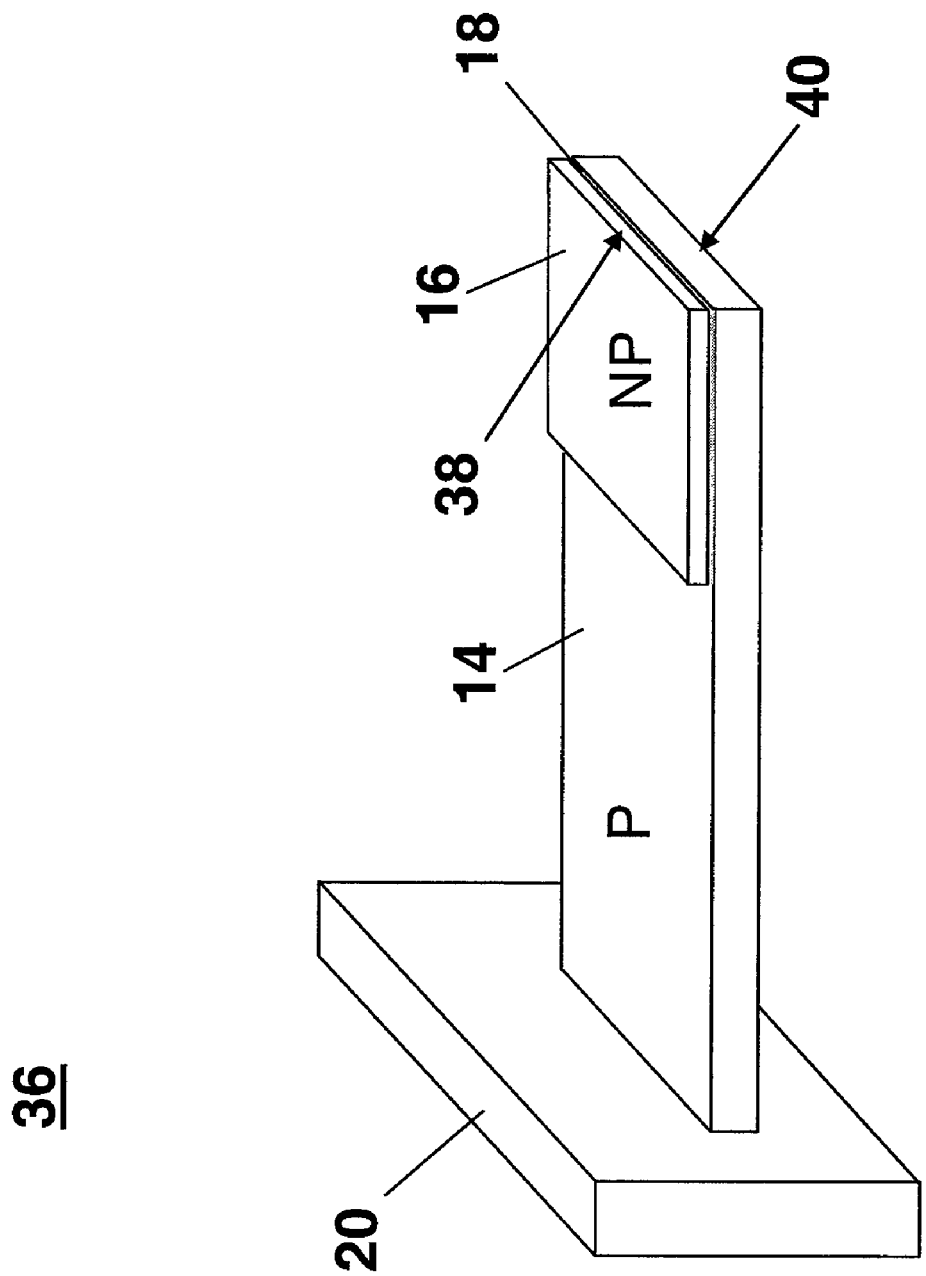
FIG. 5 is an illustration of an example configuration of a self-exciting, self-sensing piezoelectric cantilever sensor wherein the distal end of the piezoelectric layer is flush with the distal end of the non-piezoelectric layer.

The self-exciting, self-sensing piezoelectric cantilever sensor can be configured in accordance with a plurality of configurations, some of which are depicted in FIG. 5 through FIG. 16. It is to be understood however, that the configurations depicted herein do not represent all possible configurations, but rather a representative sample of configurations of the self-exciting, self-sensing piezoelectric cantilever sensor. FIG. 5 is an illustration of an example configuration 36 of an unanchored self-exciting, self-sensing piezoelectric cantilever sensor wherein the distal end 40 of the piezoelectric portion 14 is flush with the distal end 38 of the non-piezoelectric portion 16. The self-exciting, self-sensing piezoelectric cantilever sensor 36 is termed "unanchored" because the non-piezoelectric portion 16 is not attached to the base portion 20. The piezoelectric portion 14 is coupled to the non-piezoelectric portion 16 via adhesive portion 18. The adhesive portion 18 is positioned between the overlapping portions of the piezoelectric portion 14 and the non-piezoelectric portion 16. The piezoelectric portion 14 is coupled to a base portion 20.

Figure 6:
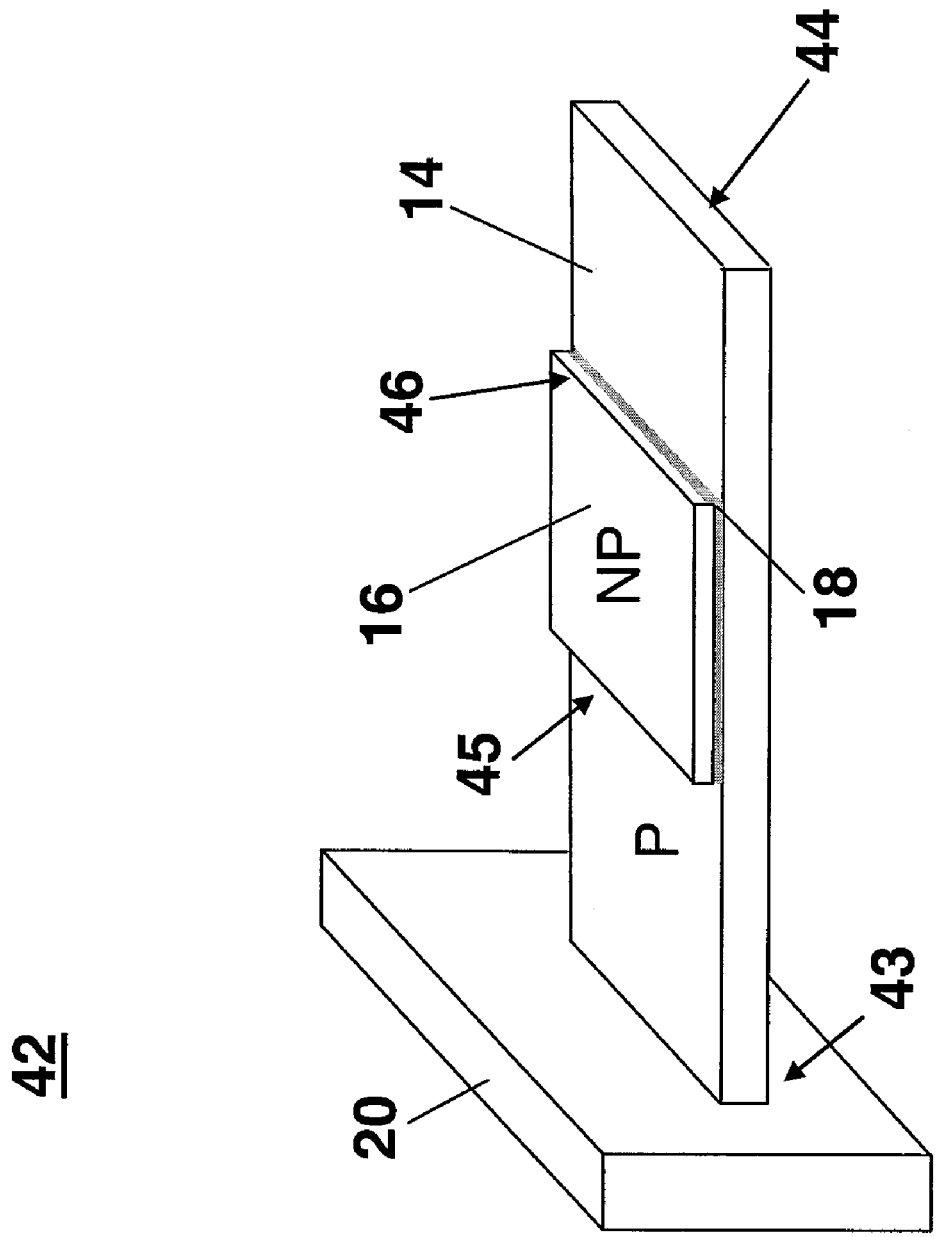
FIG. 6 is an illustration of an example configuration of a self-exciting, self-sensing piezoelectric cantilever sensor wherein the distal end of the piezoelectric layer extends beyond the distal end of the non-piezoelectric layer and the proximate end of the piezoelectric layer extends beyond the proximate end of the non-piezoelectric layer.

FIG. 6 is an illustration of an example configuration 42 of an unanchored self-exciting, self-sensing piezoelectric cantilever sensor wherein the distal end 44 of the piezoelectric portion 14 extends beyond the distal end 46 of the non-piezoelectric portion 16 and the proximate end 43 of the piezoelectric portion 14 extends beyond the proximate end 45 of the non-piezoelectric portion 16. The piezoelectric portion 14 is coupled to the non-piezoelectric portion 16 via adhesive portion 18. The adhesive portion 18 is positioned between the overlapping portions of the piezoelectric portion 14 and the non-piezoelectric portion 16. The piezoelectric portion 14 is coupled to the base portion 20.

The self-exciting, self-sensing piezoelectric cantilever sensor also can be configured to comprise multiple base portions. Example configurations of the self-exciting, self-sensing piezoelectric cantilever sensor comprising multiple base portions are depicted in FIG. 7 through FIG. 14. Configuring the self-exciting, self-sensing piezoelectric cantilever sensor to comprise multiple base portions is not intuitive because the expectation of one skilled in the art would be that affixation of both ends of the self-exciting, self-sensing piezoelectric cantilever sensor would provide a poor response as a result of the restrictions of the displacement of the self-exciting, self-sensing piezoelectric cantilever sensor as a result of its affixation to the multiple base portions. For configurations of the self-exciting, self-sensing piezoelectric cantilever sensor comprising two base portions, in an example embodiment, the stress of in the piezoelectric portion is measured, rather than the displacement of the piezoelectric portion. Configuring the self-exciting, self-sensing piezoelectric cantilever sensor to comprise two base portions provides a stable and robust sensor that can perform under relatively high media flow conditions and provide excellent mass change sensitivity. Along with providing a mechanically robust self-exciting, self-sensing piezoelectric cantilever sensor that can withstand a relatively wide range of media flow conditions with minimal determination in performance, configuring the self-exciting, self-sensing piezoelectric cantilever sensor to comprise two base portions provides a fundamental frequency (e.g., greater than 100 kHz) that is three to four times higher than a cantilever sensor having a single base portion and of similar dimensions.

Figure 7:
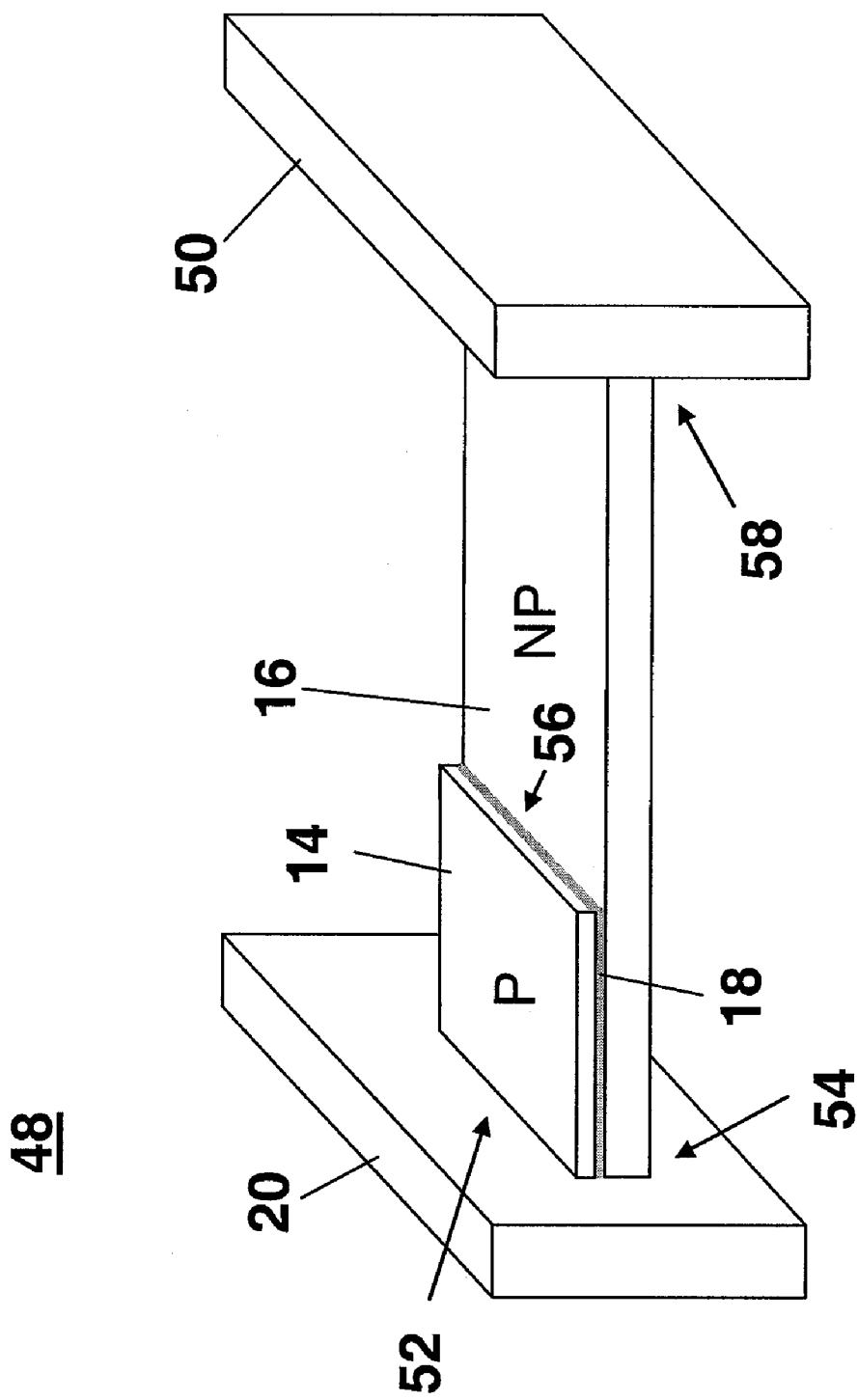
FIG. 7 is an illustration of an example configuration of a self-exciting, self-sensing piezoelectric cantilever sensor having two base portions.

FIG. 7 is an illustration of an example configuration 48 of an anchored self-exciting, self-sensing piezoelectric cantilever sensor comprising two base portions 20, 50. The self-exciting, self-sensing piezoelectric cantilever sensor 48 is termed "anchored" because the non-piezoelectric portion 16 is attached to the base portion 20. In the configuration depicted in the self-exciting, self-sensing piezoelectric cantilever sensor 48, both the proximate end 52 of the piezoelectric portion 14 and the proximate end 54 of the non-piezoelectric portion 16 are attached to the base portion 20. The piezoelectric portion and the non-piezoelectric portion can be attached to the base portion via any appropriate means. The distal end 58 of the non-piezoelectric portion 16 also is attached to the base portion 50. The distal end 58 of the non-piezoelectric portion 16 extends beyond the distal portion 56 of the piezoelectric portion 14. The piezoelectric portion 14 is coupled to the non-piezoelectric portion 16 via adhesive portion 18. The adhesive portion 18 is positioned between the overlapping portions of the piezoelectric portion 14 and the non-piezoelectric portion 16.

Figure 8:
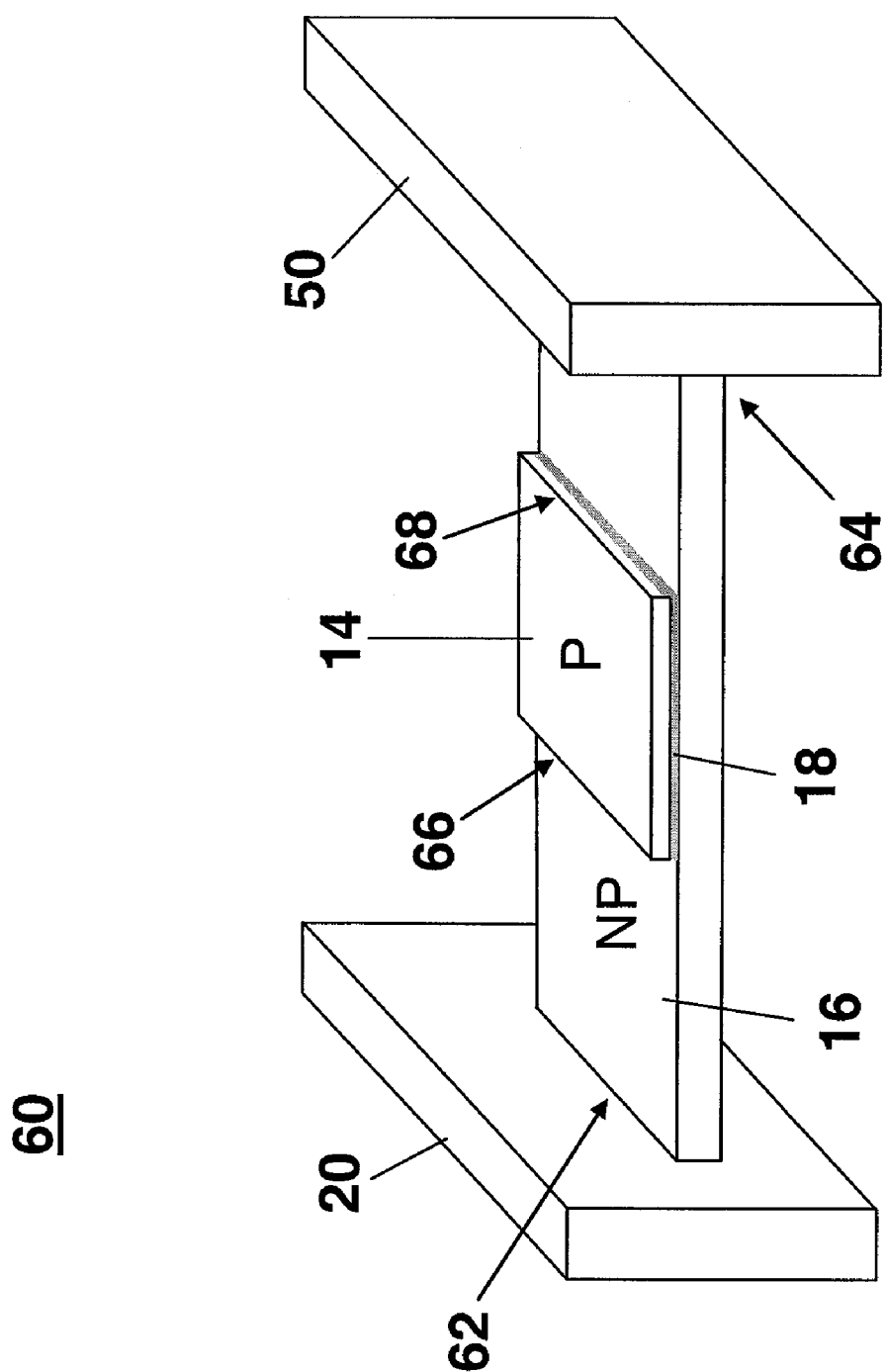
FIG. 8 is an illustration of another example configuration of a self-exciting, self-sensing piezoelectric cantilever sensor, wherein the piezoelectric layer is not attached to either base portion.

FIG. 8 is an illustration of an example configuration 60 of an anchored self-exciting, self-sensing piezoelectric cantilever sensor comprising two base portions 20, 50, wherein the piezoelectric portion 14 is not attached to either base portion 20 or base portion 50. In the configuration depicted in the self-exciting, self-sensing piezoelectric cantilever sensor 60, the proximate end 62 of the non-piezoelectric portion 16 is attached to the base portion 20 and the distal end 64 of the non-piezoelectric portion 16 is attached to the base portion 50. The proximate end 62 of the non-piezoelectric portion 16 extends beyond the proximate end 66 of the piezoelectric portion 14 and the distal end 64 of the non-piezoelectric portion 16 extends beyond the distal end 68 of the piezoelectric portion 14. The piezoelectric portion 14 is coupled to the non-piezoelectric portion 16 via adhesive portion 18. The adhesive portion 18 is positioned between the overlapping portions of the piezoelectric portion 14 and the non-piezoelectric portion 16.

Figure 9:
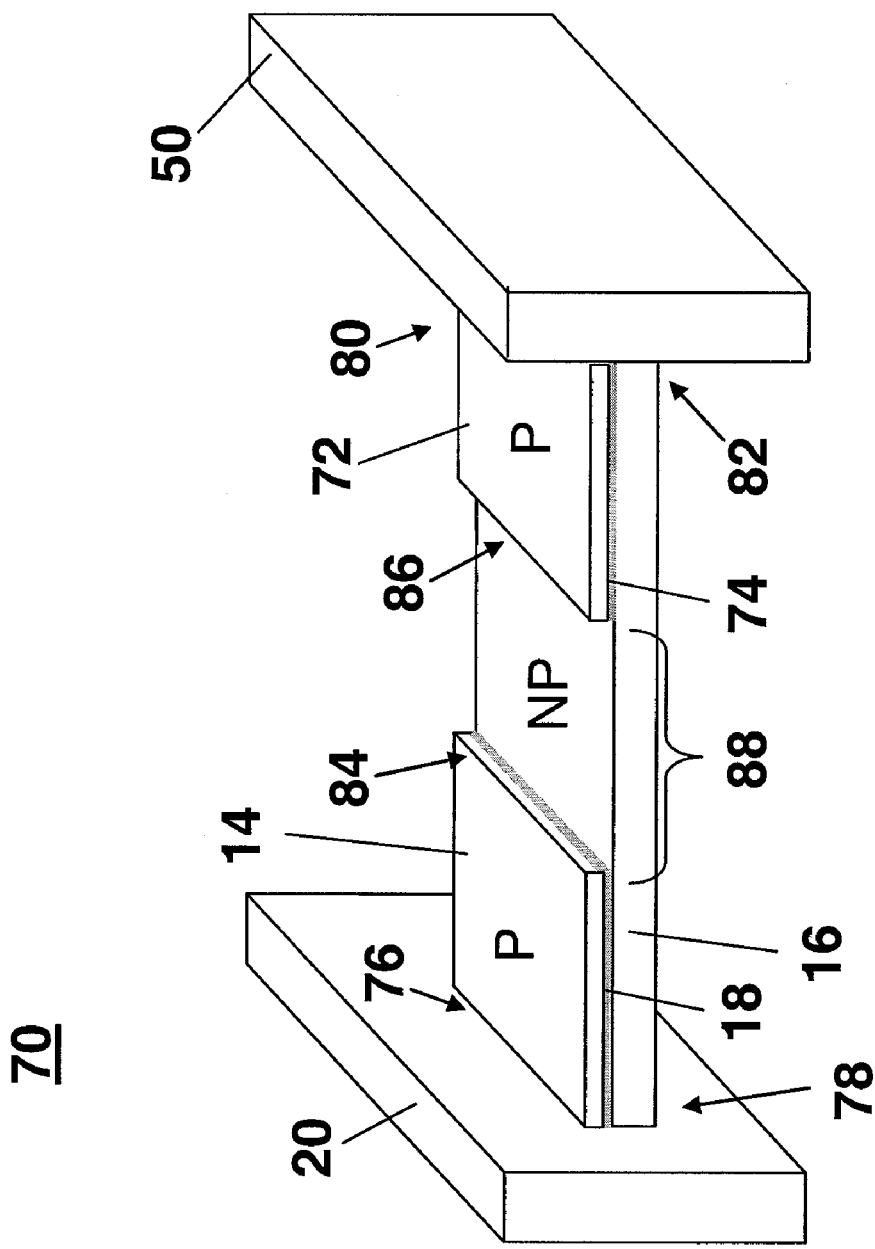
FIG. 9 is an illustration of an example configuration of a self-exciting, self-sensing piezoelectric cantilever sensor having the piezoelectric layer anchored at two ends.

FIG. 9 is an illustration of an example configuration 70 of an anchored self-exciting, self-sensing piezoelectric cantilever sensor comprising two base portions 20, 50, comprising two piezoelectric portions 14, 72, and comprising two adhesive portions 18, 74. In the configuration depicted in the self-exciting, self-sensing piezoelectric cantilever sensor 70, the proximate end 76 of the piezoelectric portion 14 and the proximate end 78 of the non-piezoelectric portion 16 are attached to the base portion 20. The distal end 80 of the piezoelectric portion 72 and the distal end 82 of the non-piezoelectric portion 16 are attached to the base portion 50. The proximate end 78 of the non-piezoelectric portion 16 extends beyond the proximate end 86 of the piezoelectric portion 72. The distal end 82 of the non-piezoelectric portion 16 extends beyond the distal end 84 of the piezoelectric portion 14. The distal end 84 of the piezoelectric portion 14 and the proximate end 86 of the piezoelectric portion 72 form a space 88 therebetween. The piezoelectric portion 14 is coupled to the non-piezoelectric portion 16 via adhesive portion 18. The piezoelectric portion 72 is coupled to the non-piezoelectric portion 16 via adhesive portion 74. The adhesive portions 18 and 74 are positioned, respectively, between the overlapping portions of the piezoelectric portion 14 and the non-piezoelectric portion 16, and the piezoelectric portion 72 and the non-piezoelectric portion 16.

Figure 10:
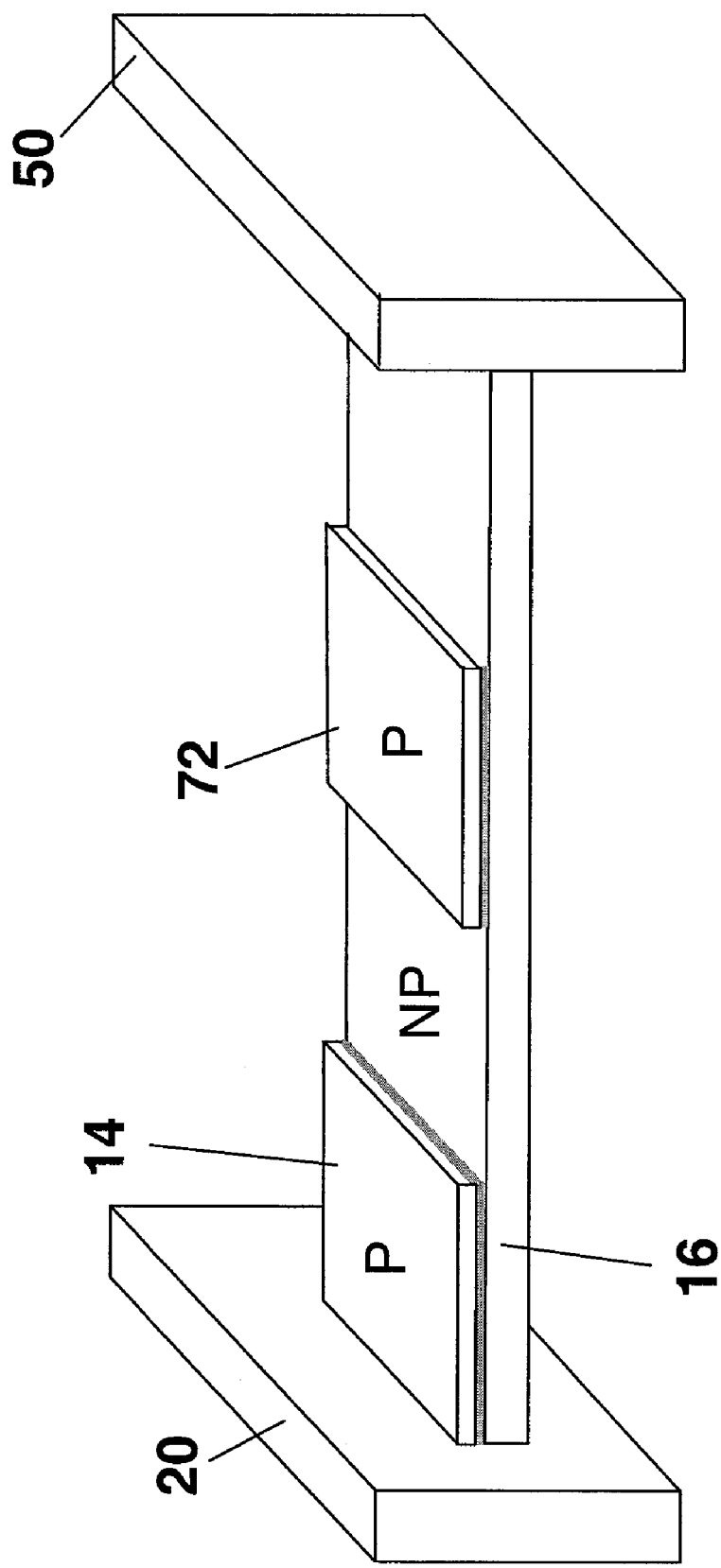
FIG. 10 is an illustration of an example configuration of a self-exciting, self-sensing piezoelectric cantilever sensor wherein the piezoelectric layer comprises two portions, one of which is anchored.
Figure 11:
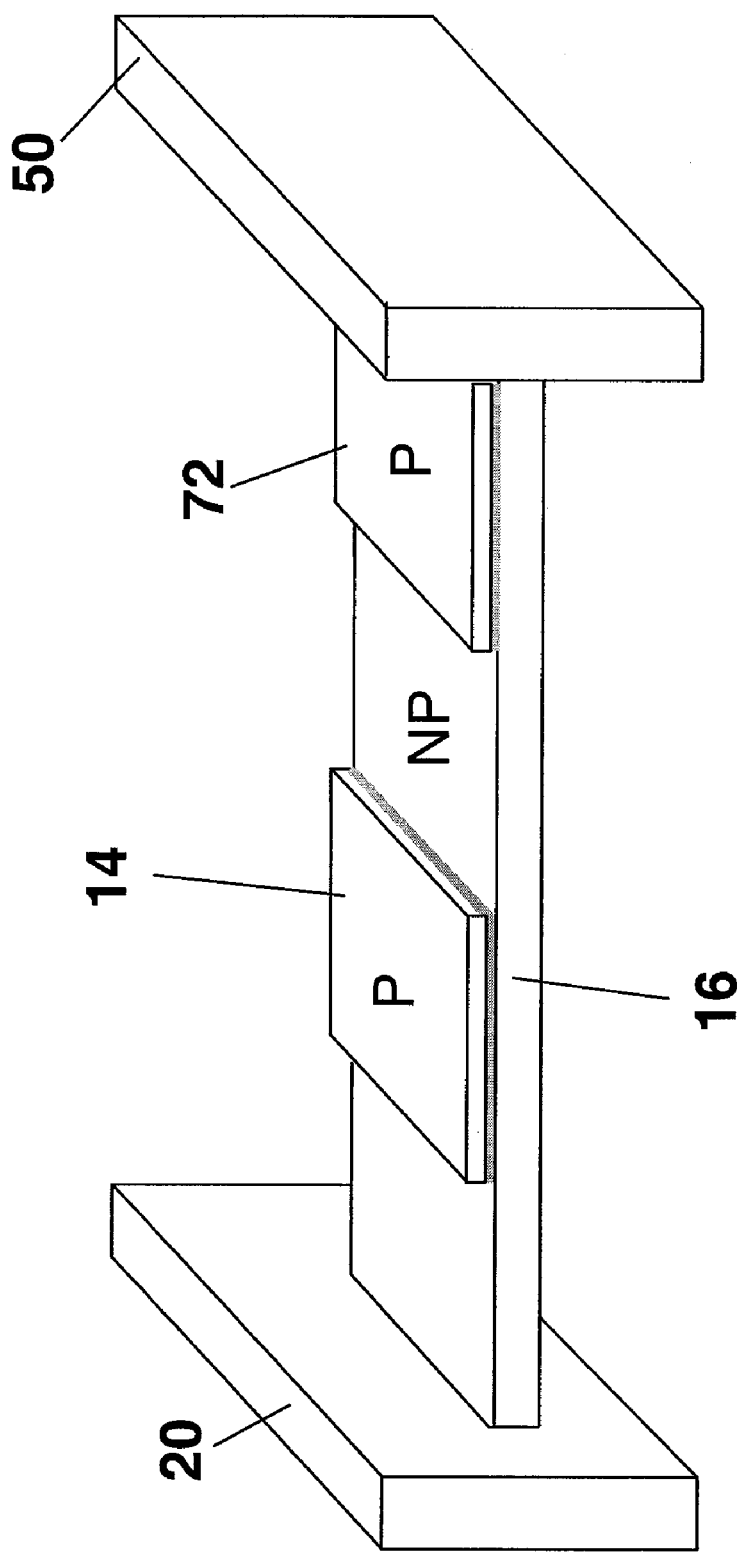
FIG. 11 is another illustration of an example configuration of a self-exciting, self-sensing piezoelectric cantilever sensor wherein the piezoelectric layer comprises two portions, one of which is anchored.
Figure 12:
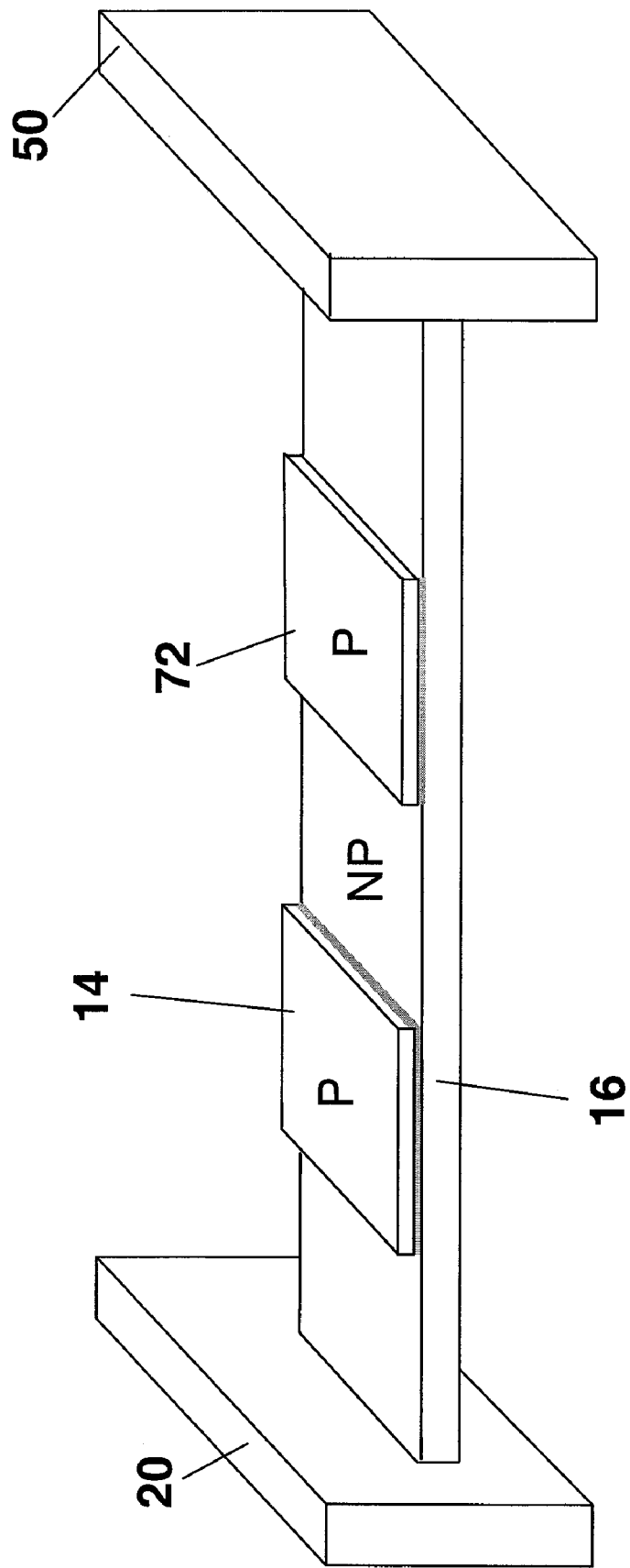
FIG. 12 is an illustration of an example configuration of a self-exciting, self-sensing piezoelectric cantilever sensor wherein the piezoelectric layer comprises two portions, neither which is anchored.

In various alternate example configurations of the configuration 70 depicted in FIG. 9, only one of the piezoelectric portions 14, 72 is attached to a respective base portion 20, 50. For example, in one example configuration as depicted in FIG. 10, the piezoelectric portion 14 is attached to the base portion 20 and the piezoelectric portion 72 is not attached to the base portion 50. In another example configuration, as depicted in FIG. 11, the piezoelectric portion 72 is attached to the base portion 50 and the piezoelectric portion 14 is not attached to the base portion 20. In yet another example configuration, as depicted in FIG. 12, neither the piezoelectric portion 14 nor the piezoelectric portion 72 is attached to a respective base portion 20, 50. In the various example configurations in which a piezoelectric layer comprises multiple portions, electrodes can be attached to any appropriate piezoelectric portion or portions. For example, in the example configuration depicted in FIG. 9, FIG. 10, FIG. 11, and FIG. 12, electrodes can be attached to piezoelectric portion 14, piezoelectric portion 72, or a combination thereof.

Figure 13:
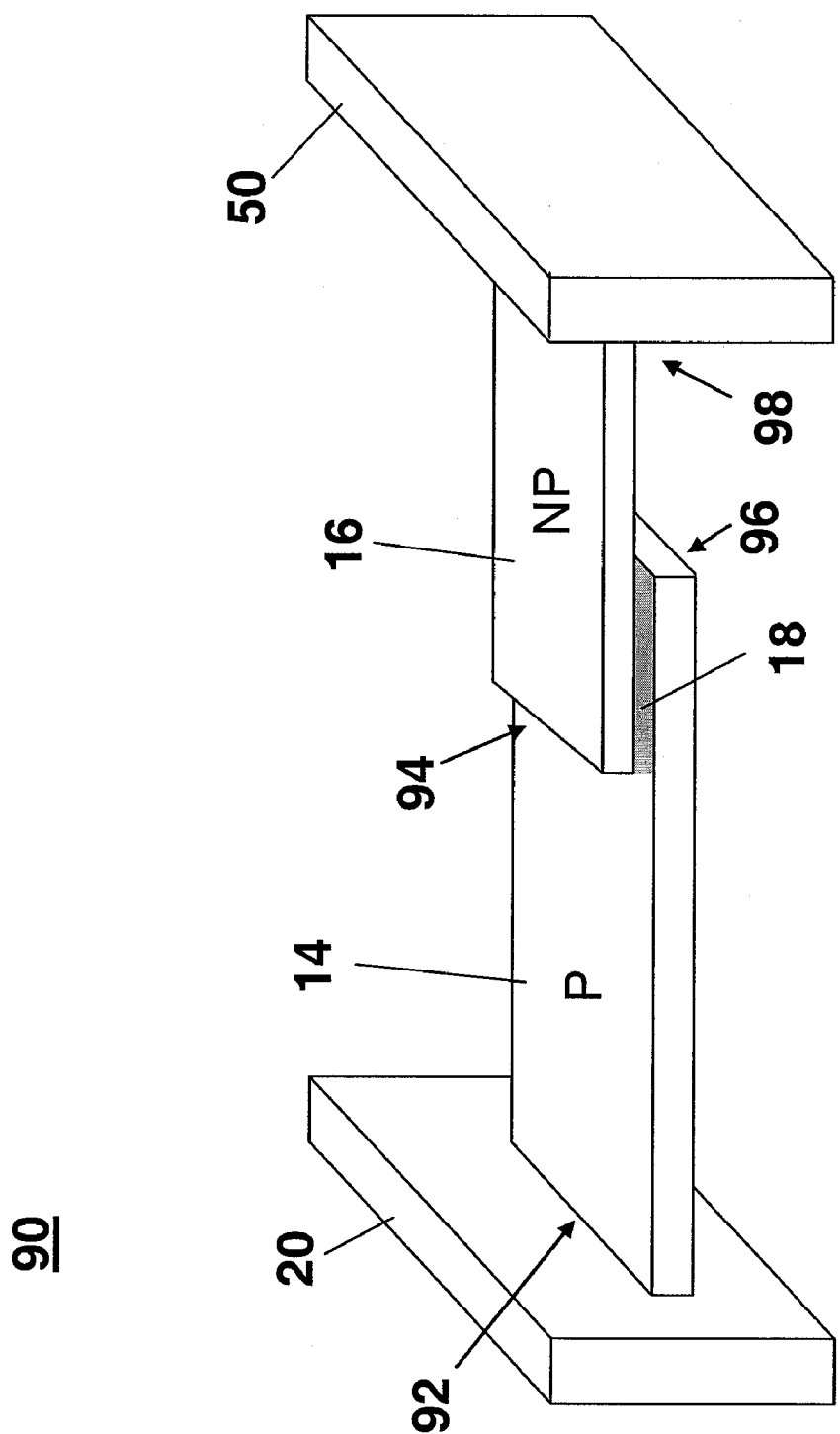
FIG. 13 is an illustration of an example configuration of a self-exciting, self-sensing piezoelectric cantilever sensor having an anchored non-piezoelectric portion and a non-anchored piezoelectric portion

FIG. 13 is an illustration of an example configuration 90 of an anchored self-exciting, self-sensing piezoelectric cantilever sensor comprising two base portions 20, 50, wherein the piezoelectric portion 14 is attached to the base portion 20 and the non-piezoelectric portion 16 is attached to the base portion 50. The piezoelectric portion 14 is coupled to the non-piezoelectric portion 16 via adhesive portion 18. The adhesive portion 18 is positioned between the overlapping portions of the piezoelectric portion 14 and the non-piezoelectric portion 16. The distal end 98 of the non-piezoelectric portion 16 extends beyond the distal end 96 of the piezoelectric portion 14. The proximate end 92 of the piezoelectric portion 14 extends beyond the proximate end 94 of the non-piezoelectric portion 16.

Figure 14:
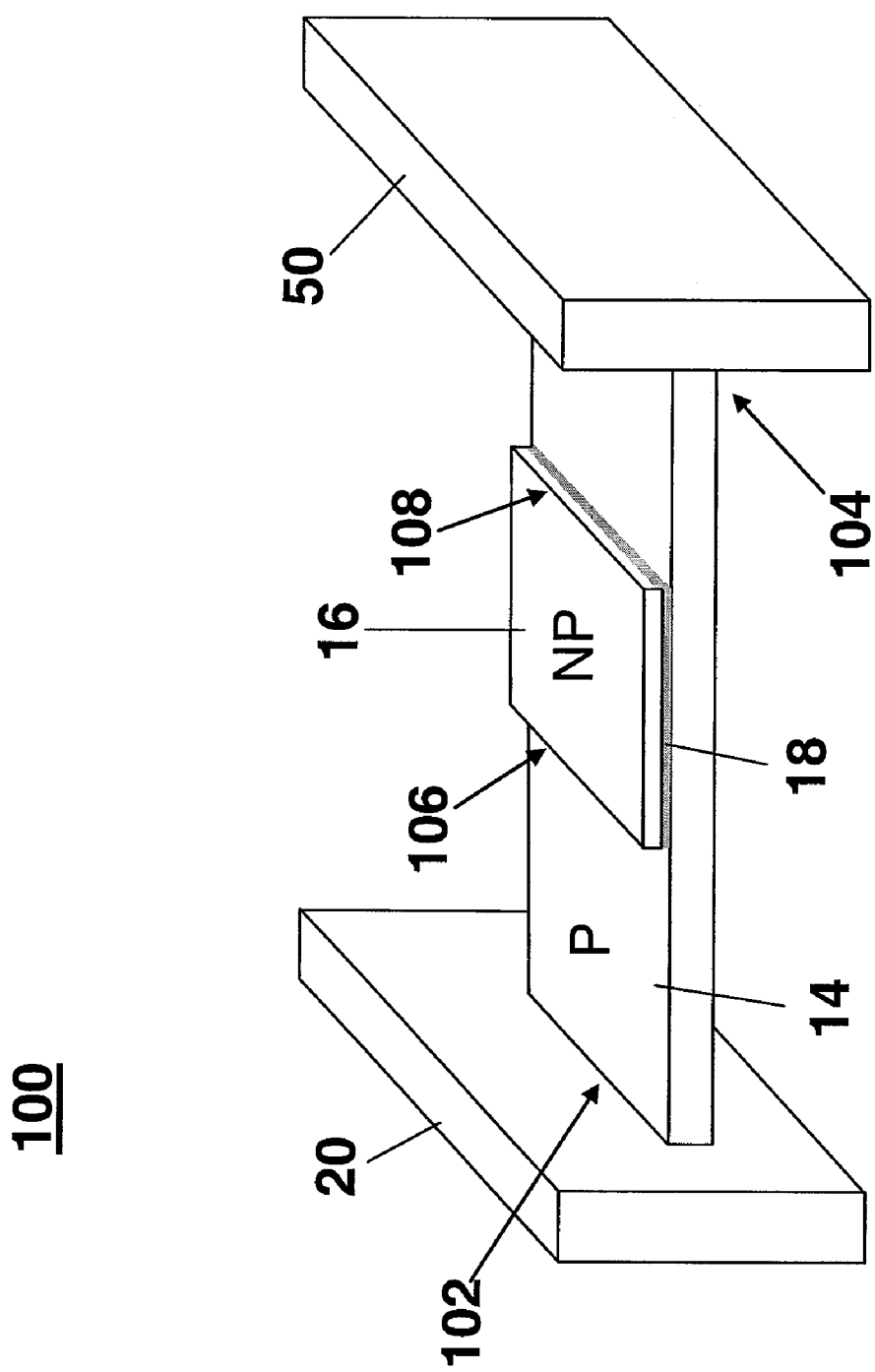
FIG. 14 is an illustration of an example configuration of a self-exciting, self-sensing piezoelectric cantilever sensor, wherein the non-piezoelectric layer is not attached to either base portion.

FIG. 14 is an illustration of an example configuration 100 of an anchored self-exciting, self-sensing piezoelectric cantilever sensor comprising two base portions 20, 50, wherein the non-piezoelectric portion 16 is not attached to either base portion 20 or base portion 50. In the configuration depicted in the self-exciting, self-sensing piezoelectric cantilever sensor 100, the proximate end 102 of the piezoelectric portion 14 is attached to the base portion 20 and the distal end 104 of the piezoelectric portion 14 is attached to the base portion 50. The proximate end 102 of the piezoelectric portion 14 extends beyond the proximate end 106 of the non-piezoelectric portion 16 and the distal end 104 of the piezoelectric portion 14 extends beyond the distal end 108 of the non-piezoelectric portion 16. The piezoelectric portion 14 is coupled to the non-piezoelectric portion 16 via adhesive portion 18. The adhesive portion 18 is positioned between the overlapping portions of the piezoelectric portion 14 and the non-piezoelectric portion 16.

Figure 15:
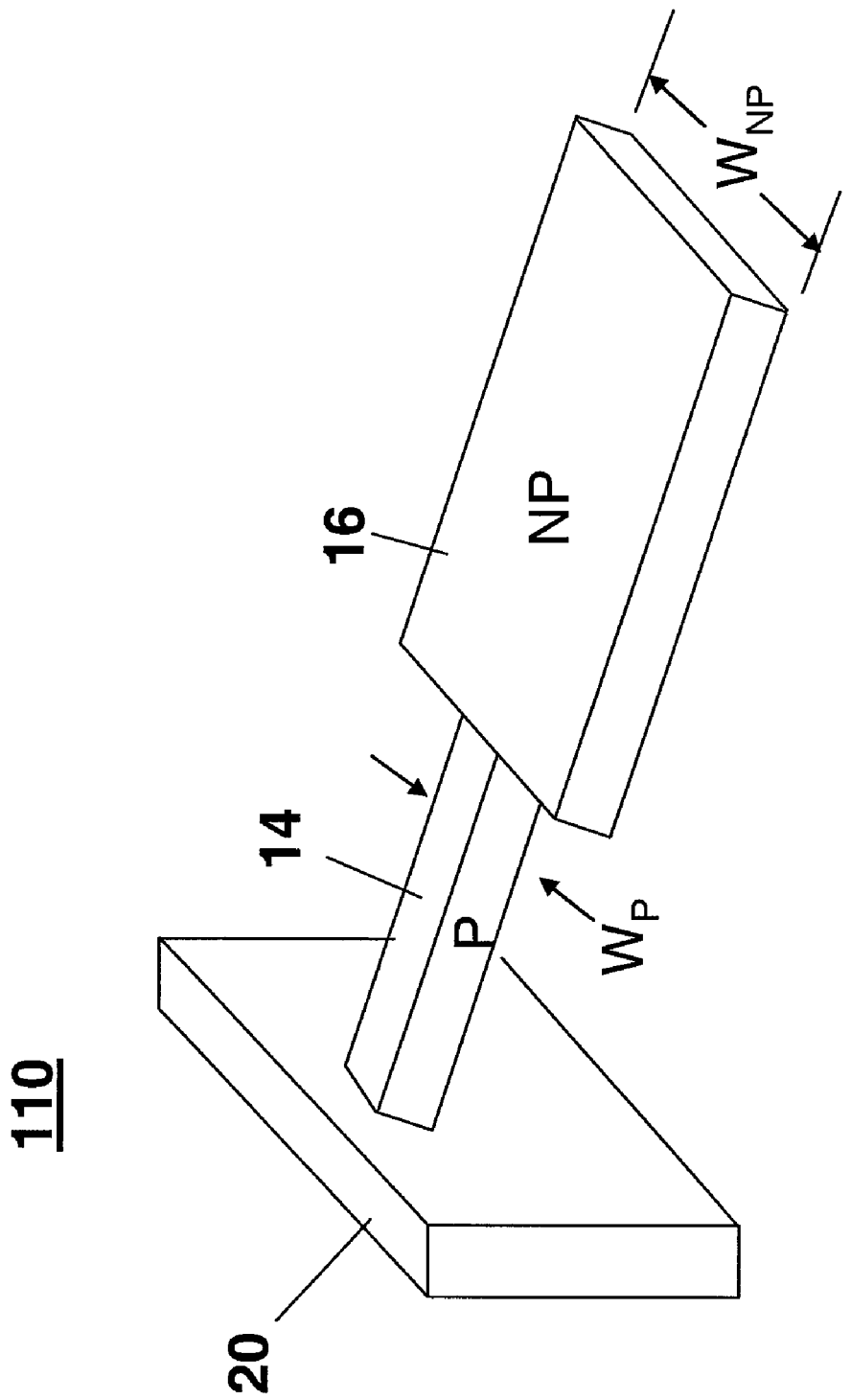
FIG. 15 is illustration of another example configuration of a self-exciting, self-sensing piezoelectric cantilever sensor wherein the piezoelectric portion has a different width than the piezoelectric portion.

FIG. 15 is an illustration of an example configuration 110 of an unanchored self-exciting, self-sensing piezoelectric cantilever sensor comprising a piezoelectric portion 14 and a non-piezoelectric portion 16, wherein the width, Wp, of the piezoelectric portion is less than the width, $W_{NP}$, of the non-piezoelectric portion 16. The configuration 110 depicted in FIG. 15 is similar to the configuration 12 depicted in FIG. 1, with the exception that $W_P$ is less than $W_{NP}$. According, the self-exciting, self-sensing piezoelectric cantilever sensor 110 depicts an embodiment of an unanchored, overhang, self-exciting, self-sensing piezoelectric cantilever sensor. The piezoelectric portion 14 is coupled to the non-piezoelectric portion 16 via adhesive portion (adhesive portion not shown in FIG. 15). The adhesive portion is positioned between the overlapping portions of the piezoelectric portion 14 and the non-piezoelectric portion 16. The piezoelectric portion 14 is coupled to a base portion 20.

Figure 16:
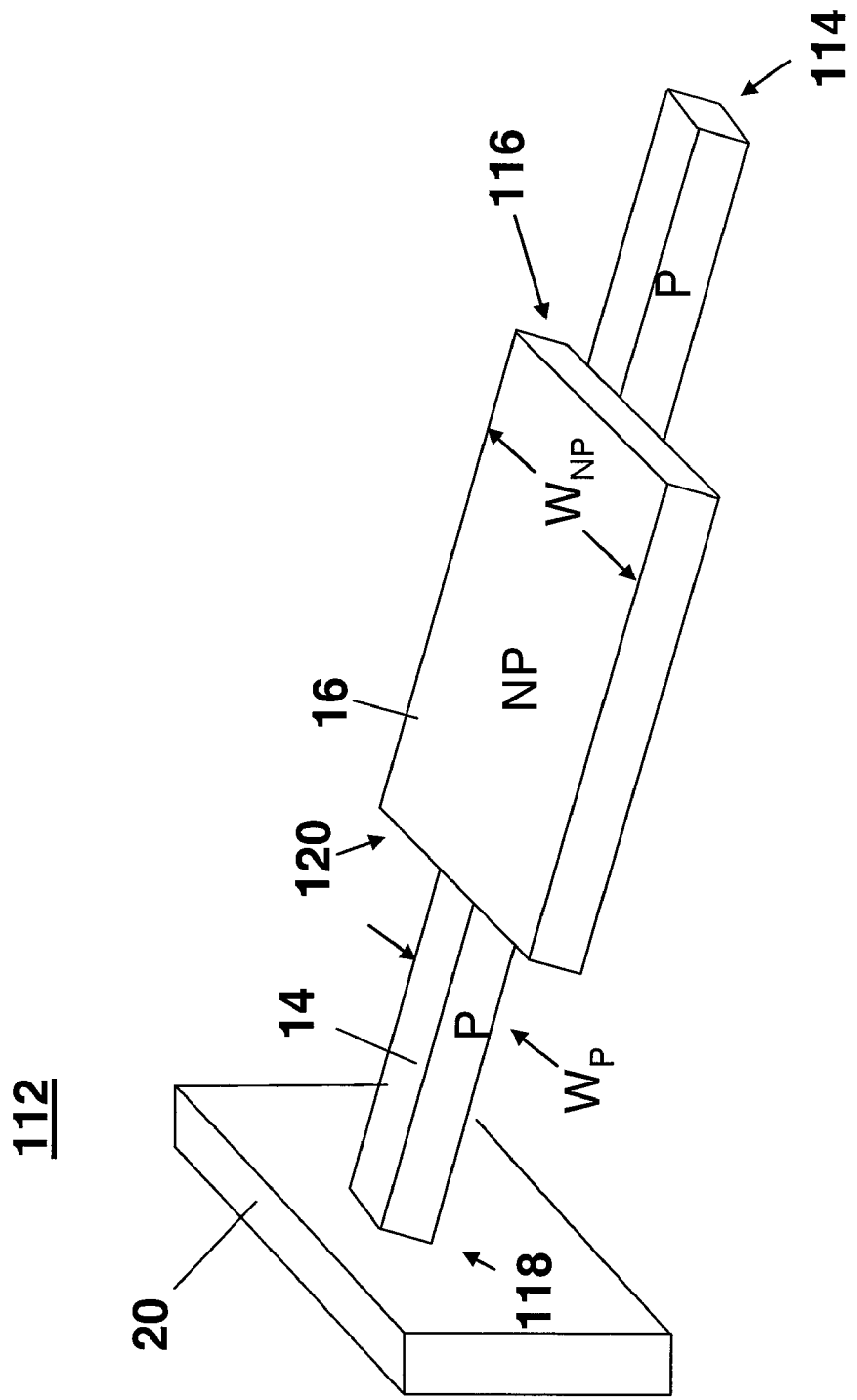
FIG. 16 is an illustration of an example configuration of a self-exciting, self-sensing piezoelectric cantilever sensor comprising a piezoelectric layer and a non-piezoelectric layer, wherein the width, of the piezoelectric layer is less than the width of the non-piezoelectric layer 16, and the distal end of the piezoelectric layer extends beyond the distal end of the non-piezoelectric layer and the proximate end of the piezoelectric layer extends beyond the proximate end of the non-piezoelectric layer.

FIG. 16 is an illustration of an example configuration 112 of an unanchored self-exciting, self-sensing piezoelectric cantilever sensor comprising a piezoelectric portion 14 and a non-piezoelectric portion 16, wherein the width, $W_P$, of the piezoelectric portion is less than the width, $W_{NP}$, of the non-piezoelectric portion 16, and wherein the distal end 114 of the piezoelectric portion 14 extends beyond the distal end 116 of the non-piezoelectric portion 16 and the proximate end 118 of the piezoelectric portion 14 extends beyond the proximate end 120 of the non-piezoelectric portion 16. The configuration 112 depicted in FIG. 16 is similar to the configuration 42 depicted in FIG. 6, with the exception that $W_P$ is less than $W_{NP}$. The piezoelectric portion 14 is coupled to the non-piezoelectric portion 16 via adhesive portion (adhesive portion not shown in FIG. 16). The adhesive portion is positioned between the overlapping portions of the piezoelectric portion 14 and the non-piezoelectric portion 16. The piezoelectric portion 14 is coupled to the base portion 20.

Figure 17:
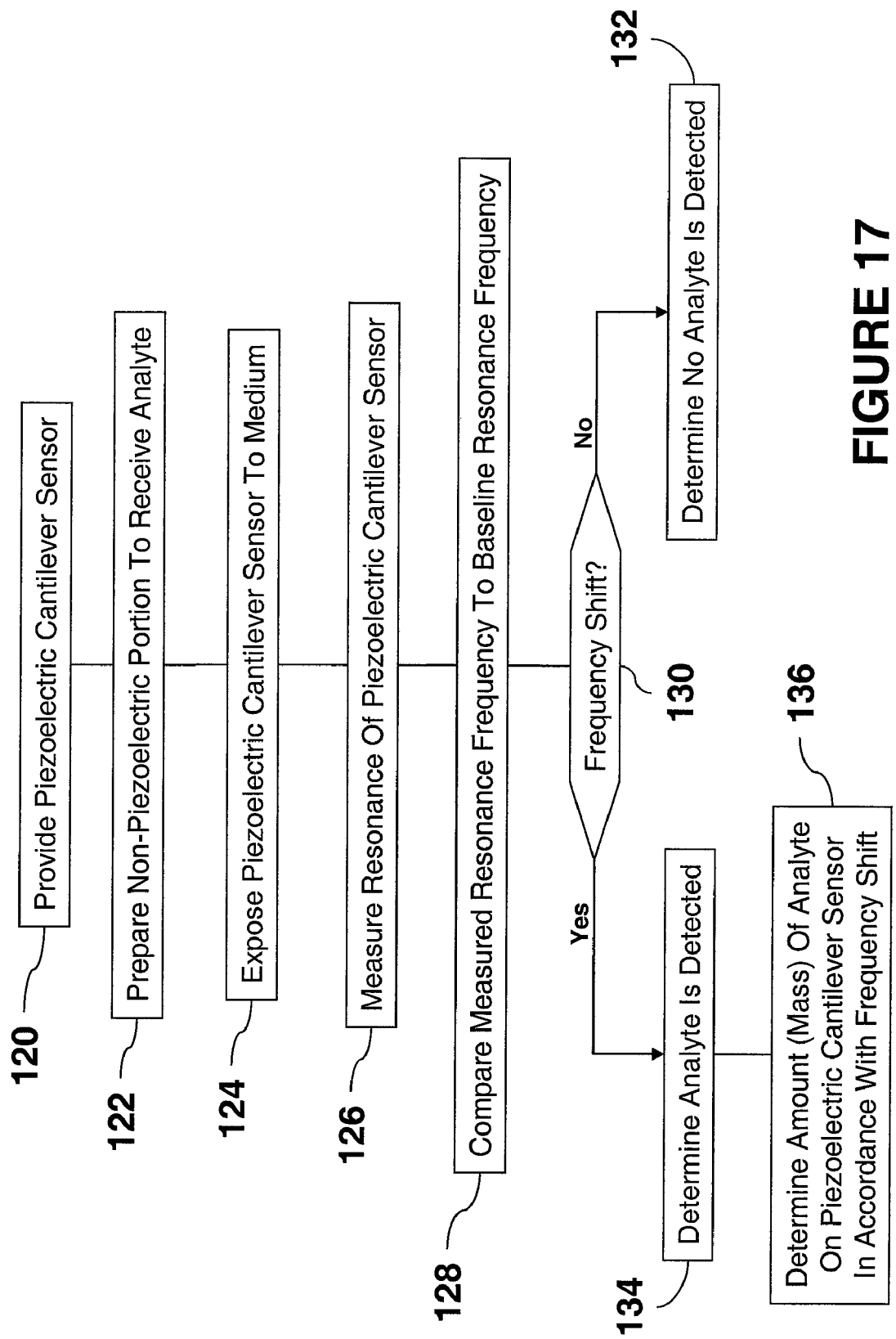
FIG. 17 is a flow diagram of an example process for detecting an analyte utilizing the self-exciting, self-sensing piezoelectric cantilever sensor.

FIG. 17 is a flow diagram of an example process for detecting an analyte utilizing the self-exciting, self-sensing piezoelectric cantilever sensor. The self-exciting, self-sensing piezoelectric cantilever sensor is provided at step 120. The self-exciting, self-sensing piezoelectric cantilever sensor can be configured in accordance with the descriptions provided above, or configured in accordance with any appropriate variant is thereof. The self-exciting, self-sensing piezoelectric cantilever sensor is prepared to receive an analyte at step 122. In an example embodiment, an analyte attractor is applied to the non-piezoelectric portion of the self-exciting, self-sensing piezoelectric cantilever sensor. The attractor is specific to an analyte. Thus the attractor will attract a target analyte and not attract other substances. For example, the non-piezoelectric portion of the self-exciting, self-sensing piezoelectric cantilever sensor can comprise an attractor for attracting bioterrorism agents, such as *Bacillus anthracis*, food-borne pathogens, such as *E. coli*, pathogens in food and water, cell types in body fluids (e.g., circulating tumor cells), biomarkers in body fluids (e.g., proteins that mark specific pathophysiology-alpha-fetoprotein, beta-2-microglobulin, bladder tumor antigen, breast cancer marker CA-15-3, and other CAs (cancer antigens), calcitonin, carcinoembryonic antigen, and others), markers of explosives such as trinitrotoluene, dinitrotoluene, airborne and waterborne toxins, biological entities, such as a protein, or a combination thereof, for example.

The self-exciting, self-sensing piezoelectric cantilever sensor is exposed to a medium at step 124. The medium can comprise any appropriate medium, such as a liquid, a gas, a combination of a liquid and a gas, or a vacuum, for example. The medium can exhibit a wide variety of flow conditions. If a target analyte is present in the medium, the target analyte will accumulate on the non-piezoelectric portion of the self-exciting, self-sensing piezoelectric cantilever sensor that has been treated with the attractor. As described above, accumulation (e.g., binding) of the target analyte on the non-piezoelectric portion of the self-exciting, self-sensing piezoelectric cantilever sensor will result in a change in stiffness of the self-exciting, self-sensing piezoelectric cantilever sensor and/or an increase the mass of the self-exciting, self-sensing piezoelectric cantilever sensor, which will decrease the resonance frequency of the self-exciting, self-sensing piezoelectric cantilever sensor.

The resonance frequency of the self-exciting, self-sensing piezoelectric cantilever sensor is measure at step 126. The resonance frequency can be measured by any appropriate means, such as an operational amplifier, an impedance analyzer, a network analyzer, an oscillator circuit, or the like, for example. When the piezoelectric material of the piezoelectric portion of the self-exciting, self-sensing piezoelectric cantilever sensor is excited, the non-piezoelectric portion of the self-exciting, self-sensing piezoelectric cantilever sensor flexes to accommodate the strain caused in the piezoelectric material. When the frequency of excitation is the same as the natural frequency of the underlying mechanical structure, resonance occurs.

The measured resonance frequency is compared to a baseline resonance frequency at step 128. The baseline resonance frequency is the resonance frequency of the self-exciting, self-sensing piezoelectric cantilever sensor having no analyte accumulated thereon. If a difference in frequency (frequency shift) between the measured resonance frequency and the baseline resonance frequency is not measured (at step 130), it is determined, at step 132, that no analyte is detected. If a difference in frequency between the measured resonance frequency and the baseline resonance frequency is measured (at step 130), it is determined, at step 134, that an analyte is detected, i.e., an analyte is present in the medium. At step 136, the amount of mass of the analyte that has accumulated on the non-piezoelectric portion of the self-exciting, self-sensing piezoelectric cantilever sensor is determined in accordance with the frequency shift measured at step 130.

Figure 18:
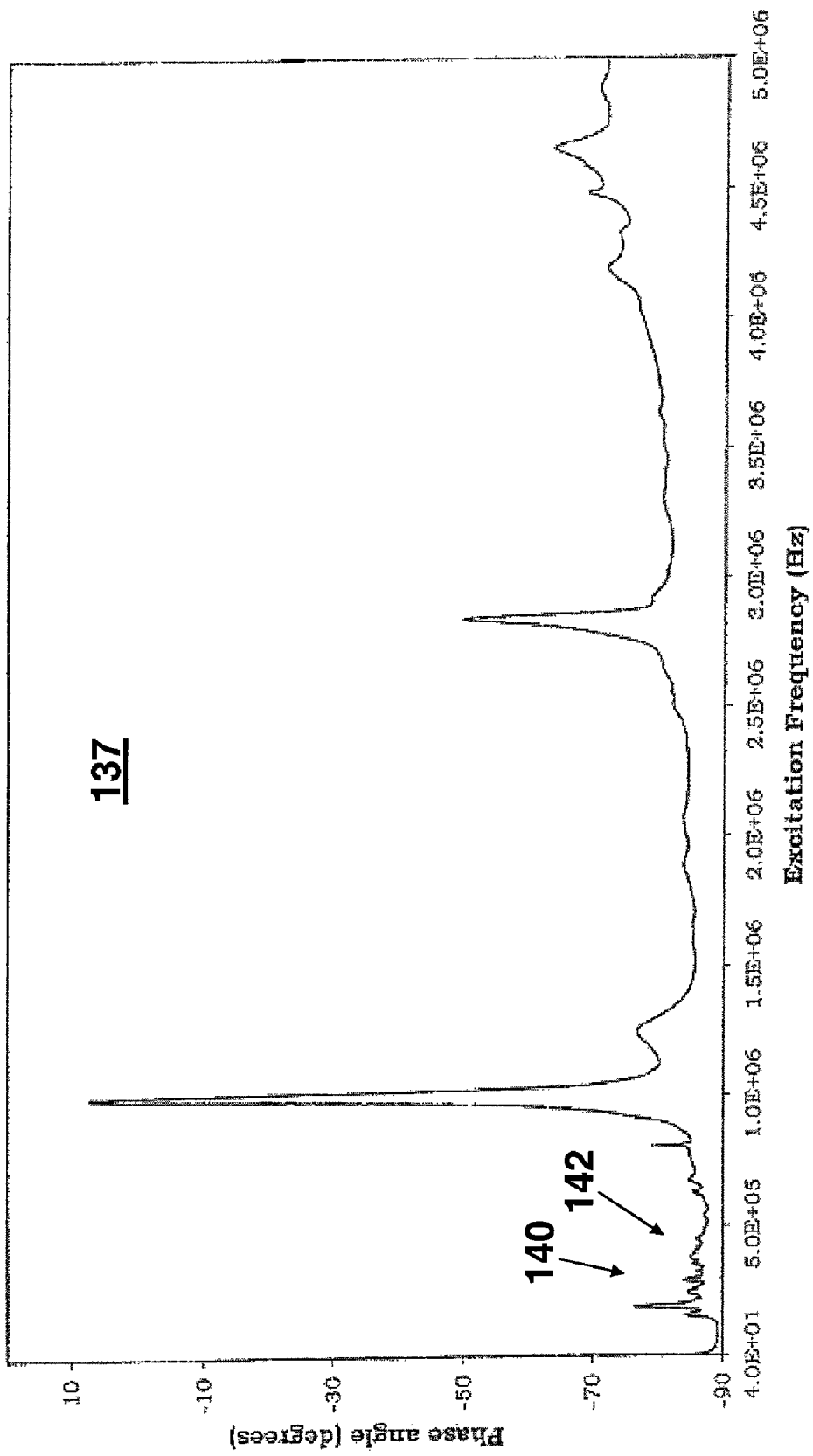
FIG. 18 is a plot of an example resonance spectrum of the configuration of the self-exciting, self-sensing piezoelectric cantilever sensor depicted in FIG. 1, operated in air.

Various experiments have been conducted utilizing various configurations of the self-exciting, self-sensing piezoelectric cantilever sensor. FIG. 18 is a plot 137 of an example resonance spectrum of the configuration 12 of the self-exciting, self-sensing piezoelectric cantilever sensor, depicted in FIG. 1, operated in air. The width, $W_P$, and the width, $W_{NP}$, were each approximately 2 mm. The plot 137 shows the phase angle (between the excitation voltage and the excitation current) versus excitation frequency, at an excitation voltage of 100 mV. The first resonance frequency mode 140 occurred approximately between 150 and 200 kHz and the second resonance frequency mode 142 occurred between 250 and 300 kHz. The resonance spectrum shows higher order characteristic peaks at approximately 980 kHz, 2.90 MHz and 4.60 MHz.

Quality factors were determined as a ratio of the resonant frequency to the peak width at half the peak height. As a result, the quality factor is a measure of the sharpness of the resonant peaks. Experimentation has shown that the quality factor of the self-exciting, self-sensing piezoelectric cantilever sensor does not decrease significantly when the sensor is placed in different environments ranging from vacuum to liquid flow environments. Also, experimentation has shown that the Q values for the various configurations of the self-exciting, self-sensing piezoelectric cantilever sensor typically range between 10 and 70, depending upon the respective frequency mode where the peak is detected. The various configurations of the self-exciting, self-sensing piezoelectric cantilever sensor, when used in vacuum, air, and viscous environments, including flows, typically did not have more than a 20%-35% decrease in Q value. This relatively small loss in the overall value of the quality factor reflects the ability of the self-exciting, self-sensing piezoelectric cantilever sensor to accurately detect chemicals and various biological items in viscous environments, including water and bloodstreams.

Experimentation has shown that the sensitivity of the self-exciting, self-sensing piezoelectric cantilever sensor is a function of the dimensions thereof. Specific changes in the geometry of the self-exciting, self-sensing piezoelectric cantilever sensor enhanced the sensor's mass change sensitivity, and thus, the sensor's response to the detection of low concentration of analyte. The resonance spectrum, a plot of phase angle versus excitation frequency, in air, showed dominant bending mode resonant peaks at 102±0.05, 970±0.05, and 1810±0.05 kHz, respectively. By changing the geometry of the of the self-exciting, self-sensing piezoelectric cantilever sensor, the sensor's resonance characteristics were enhanced. The corresponding bending resonant modes occurred at higher frequencies and had larger phase angles, suggesting that resonant peaks of the self-exciting, self-sensing piezoelectric cantilever sensor are more sensitive and are less dampened.

In an example experiment, the mass change sensitivity of the self-exciting, self-sensing piezoelectric cantilever sensor was measured. A known mass of paraffin wax was added to a glass surface of the self-exciting, self-sensing piezoelectric cantilever sensor and the change in resonant frequency was used to compute the mass sensitivity, expressed in g/Hz. Direct measurement was made of the mass change sensitivity in liquid; as well as the ratio of known mass to the change in resonant frequency in liquid before and after mass was added. The mass sensitivity of the resonant mode investigated under liquid was determined to be $1.5 \times 10^{-15}$ g/Hz.

Application of Piezoelectric Cantilever Sensors to the Detection of Airborne Analytes Applicants has found no published information concerning the detection of a target analyte in a gas phase. The present invention addresses the detection of a target analyte in a gas phase by binding the analyte to a recognition entity within a sensor. The recognition entity exhibits an affinity for the target analyte. Examples of biological recognition entities include polyclonal and monoclonal antibodies, single-chain antibodies (scFvs), aptamer (synthetic DNA that is specially developed to detect a target molecule), recombinant and natural phage, and the like. In one embodiment, when using frequency transduction methods such as described herein, a detector makes use of immobilized antibodies as a recognition entity to detect concentrations of airborne analytes. Immobilized antibodies are antibodies that are attached as a recognition entity onto the surface of a sensor that is used for airborne detection. This type of airborne detection provides a rapid and accurate detection of biological substances, such as pathogens including bacteria, virus, oocysts, prions, and spores, as well as non-biological substances, such as chemicals. Biological threats, such as bacteria, spores, and the like may be detected as well as chemical threats such as explosive or toxic chemicals.

In one aspect of the invention, airborne detection of a analyte using a recognition entity, such as described above, is performed by exposing a sensor having recognition entity, such as a coated surface of a sensor, to an airflow. The airflow may or may not contain the analyte. If the airflow does not contain the analyte, then no detection is expected. However, if the analyte is present in the airflow then the analyte bonds to the recognition entity and affects characteristics of the sensor. The changed characteristics can be detected with a transducer that detects the presence of analyte now bonded to the sensor. Specifically, the transducer mechanism can operate via optical, frequency, capacitance, electrical conductivity, bending mode, or static mode cantilever. The transducer mechanism can determine the change in characteristic of the sensor as a result of the bonding of the analyte with the recognition entity. As a result, the changed characteristic, (i.e. size, frequency, mass, capacitance, electrical conductivity, bending mode, etc) can be detected and quantified. Once quantified, the amount of the analyte bonded to the recognition entity can be determined using calculation means known to those of skill in the art such as a computer, an embedded processor, or digital or analog circuitry. One such transducer mechanism is frequency wherein the mechanical resonance of the sensor changes as analyte becomes bonded to the recognition surface of the sensor. Example embodiments using frequency transduction are presented below. However, other transduction mechanisms are possible as described above.

In one embodiment of frequency transduction for the detection of airborne analytes, piezoelectric-excited millimeter-sized cantilever (PEMC) sensors, because of their high sensitivity, are found by the inventors to be useful for the detection of airborne species. A PEMC surface prepared with a recognition entity, such as an antibodies or DNA molecules, will respond to the targeted analyte, which may be a pathogen, a protein, or a biomolecule. Such an event causes a change in the cantilever mass which manifests as a resonance frequency change, and can be monitored by an appropriate analyzer. Suitable analyzers may include, lock-in amplifiers, impedance analyzers, network analyzers or even an oscillator circuit.

In the present application, a technique for detection of an airborne pathogen is described. One aspect includes a method of contacting a target organism or molecule, in air, with a PEMC sensor including a recognition molecule to sense the presence of the target organism or molecule. One advantage of the present invention is that this can be carried out without having to collect the target organism or molecule in a liquid medium for sensing. Traditional approaches deploy a sensor in a liquid environment. It is known that a dynamic sensing surface, such as an oscillating surface, resists the attachment of undesirable particulate contaminates. Since PEMC sensors are vibrating while in contact with the gas stream, only chemical bound attachment can occur thereby reducing or eliminating false positives from gas borne particulate contaminants in an airflow sample. This principle becomes an advantage of the current invention because the PEMC sensors can, by their operation, provide specificity in detection to the exclusion of contaminants.

In one embodiment of this invention, the position and/or orientation of the sensor surface with respect to a flowing air stream in a low velocity flow region is specified. Preferably, air flow velocities of about 0.01 to about 30 meter/second are used for detection. The low velocity flow region provides increased contact time between the target species and the sensor surface for binding. Contact time between the target species and the sensor surface can also be enhanced by the specific position or orientation of the sensor surface relative to the air flow. Preferably, the sensor surface is oriented substantially orthogonal to the air flow, though other orientations are also possible. Binding affinity of the spore to the antigen on the sensor may depend on local humidity. Keeping the humidity in the range of 10 to 95% provides sufficient binding and a value of 95% provides excellent binding affinity. While binding has been observed in the flow velocity range of 0.01 to 30 m/s, the lower end of this range shows higher binding kinetics. In some embodiments, an airflow velocity of 0.01 to 10 meters/second was an acceptable rate.

The methods of the present invention have been demonstrated to detect anthrax spores at concentrations as low as 40 spores per liter of air, measuring directly in air without the need for preparation of liquid or gel matrix based samples.

FIGS. 19A-19G show embodiments of various piezoelectric cantilever sensors which may be used in the methods of the present invention. It should be noted that the figures of the present application are not to scale unless otherwise indicated and that the figures are conceptual in presentation. In FIGS. 19A-19G, each sensor is comprised of a piezoelectric layer 14 (labeled P), an adhesive layer 18 (located between the overlapping portions of the piezoelectric layer and the non-piezoelectric layer), and a non-piezoelectric layer 16 (labeled NP) that includes a portion that extends as a tip. Base 20 is where the piezoelectric layer 14 is attached. Base 20 typically has electrodes (not shown) or some other similar means, associated therewith for connection to the piezoelectric layer 14, though the electrodes need not be associated with the base 20 as long as the electrodes are connected to the piezoelectric layer 14. The electrodes may be placed anywhere on the piezoelectric layer 14. There may also be a bonding pad that is made of gold, $SiO_2$, a material capable of immobilization of a receptor material, and/or an absorbent material appropriate for use in chemical sensing or for bio-sensing. One of skill in the art will recognize that the designs described in FIGS. 19A-19G are only a subset of the possible geometries. Thus, variations of those designs are within the scope of the present application. For Example, the non-piezoelectric part of the sensor may be attached to the piezoelectric layer in one or many discrete numbers, either across the entire width of the piezoelectric layer or a part of it.

A cantilever or a beam (simple or composite) sensor is mechanically oscillated by AC electrical excitation of the PZT layer. When excitation frequency coincides with the mechanical resonance frequency or its higher modes, oscillation magnitude (deflection from equilibrium) is larger than at lower or higher frequency. Therefore at resonance the PZT experiences a higher stress level compared with levels present at non-resonance frequency. The stress level in the PZT varies along its length, and depends on the mode shape. The mode shape in turn also depends on the bending modulus of the cantilever. For example, referring to FIG. 19A, bending modulus at section R is much higher than at Section S. Location of the exitation electrode solder point at or near the location of higher stress is advantageous as it gives a larger signal as measured by electrical impedance. The sensitivity of a free-end cantilever or a beam sensor is higher at higher resonance frequency. The various example structures illustrated in FIGS. 19A-19G and FIGS. 35-46 are designed to achieve a dominant high-order resonance mode in the range of 60 kHz to 6 MHz. The location of the discrete non-piezoelectric layer can be designed such that certain high-order modes are enhanced, and non-flexural modes are reduced in intensity.

Piezoelectric layer 14 may be constructed out of lead zirconate titanate, lead magnesium niobate-lead titanate solid solutions, strontium lead titanate, quartz silica, piezoelectric ceramic lead zirconate and titanate (PZT) or Piezoceramic-polymer 1-3 fiber composites. The non-piezoelectric layer 16 may be constructed from ceramics, metals, polymers and composites of one or more of ceramics, metals, and polymers, such as silicon dioxide, copper, stainless steel, and titanium. Any known material for use in constructing the non-piezoelectric layer of conventional piezoelectric cantilevers may be employed to construct the non-piezoelectric layer. The electrodes may be any suitable, conventional electrodes. In one embodiment, the electrodes may be insulated or non-insulated depending on the exposure environment of the various piezoelectric cantilever sensors.

Detection is accomplished by measuring an oscillation (i.e. a resonance frequency) of the apparatus and comparing the measured oscillation (resonance frequency) to a baseline oscillation (resonance frequency) to determine a frequency shift. The determined frequency shift may then be used to determine the presence of an analyte that adheres to a recognition entity deposited on one of the piezoelectric or non-piezoelectric layers of the sensor. The combination of piezoelectric layer, the non-piezoelectric layer, and the recognition entity comprise the cantilever which oscillates when exited by electrodes attached to the piezoelectric layer.

One aspect of the invention is an apparatus and method for measuring any analyte that can be bound directly or indirectly to a surface. The binding of the analyte results in one or both of a mass change or a stiffness change. These changes can be measured as a resonance frequency change, and can be monitored by an appropriate analysis device, such as a lock-in amplifier, impedance analyzer, network analyzer or an oscillator circuit. Embodiments of the invention include novel geometric designs of the piezoelectric cantilever. Conventional piezoelectric cantilevers are fabricated with the piezoelectric layer attached to a non-piezoelectric layer over an entire surface of the piezoelectric layer. In some conventional piezoelectric cantilevers, the piezoelectric layer is fixed at one end so that when the piezoelectric material is excited, the non-piezoelectric layer flexes to accommodate the strain caused in the piezoelectric material. When the frequency of excitation is the same as the natural frequency of the underlying mechanical structure, resonance occurs. This type of a cantilever sensor is good for operation at frequencies lower than about 100 kHz at millimeter size. Higher frequencies are possible only by making the cantilever very short (less than 1 mm).

Another version of a conventional piezoelectric cantilever includes the piezoelectric material is not affixed at one end. This is the so-called "unanchored piezoelectric cantilever." The unanchored piezoelectric cantilever presents its first bending mode resonance at over 100 kHz, while conventional anchored cantilevers present their first bending mode resonance at 2-60 kHz. The second bending mode resonance generally lies in the range of 200 kHz, and higher modes are present at 400 kHz, 800 kHz and potentially even higher frequencies.

Any mode that exhibits a Q value higher than 10 is convenient in a practical sense. Q values are the ratio of the resonance peak frequency relative to the resonance peak width at half peak height. Not all modes that show high Q value, however, provide sensitive detection. The difference in resonance frequency between air and water, and air and vacuum gives a measure of sensitivity, as the differences in density cause a frequency shift in the resonance frequency. In many piezoelectric cantilever sensors, the change in media from air to vacuum causes a resonance frequency change of 4 to 25 kHz depending on the particular geometry of the sensor The relative length and widths of the piezoelectric and non-piezoelectric layers determines the sensitivity, and also the shape of the peak of the frequency spectrum provided by the sensor. This can be seen from the spectra of various piezoelectric cantilever sensors included as figures herein.

The instant invention permits detection of extremely small concentrations of analyte that will bind to the piezoelectric cantilever surface. In the examples, detection of pathogens and proteins has been demonstrated at low concentrations in air. Furthermore, any analyte that will bind to an organic or inorganic functional group on the PEMC surface can be detected. Thus, both chemical and biological agents can be detected in an airborne environment using the PEMC-based devices.

There are various potential applications for the cantilevers of the present invention, such as for the detection of bioterrorism agents, such as *Bacillus anthracis*, the detection of airborne pathogens, the detection of markers of explosives such as trinitrotoluene, such as the presence of dinitrotoluene, and the detection of airborne toxins. The piezoelectric cantilever of the present invention may also be used for the detection of biological entities at picogram levels, and for the detection of protein-protein interactions, both steady state and kinetic.

As an example use application, there are non-biological entities that have a high affinity to certain chemical coatings, and thus an airborne analyte sensor, such as the PEMC or PEMCB sensors, can be used in non-biological applications such as the detection of toxic or explosive chemicals. For example, a polymer coating of aSXFA-[poly(1-(4-hydroxy-4-trifluoromethyl-5,5,5-trifluoro)pent-1-enyl)methylsiloxane] as a recognition entity may be used to detect 2,4-dinitrotoluene (DNT). Also, a molecularly imprinted polymers (MIPs) as a recognition entity may be used for detection of explosives such as trinitro toluene (TNT) and explosive signatures such as 2,4-dinitro toluene (2,4-DNT).

Figure 19A:
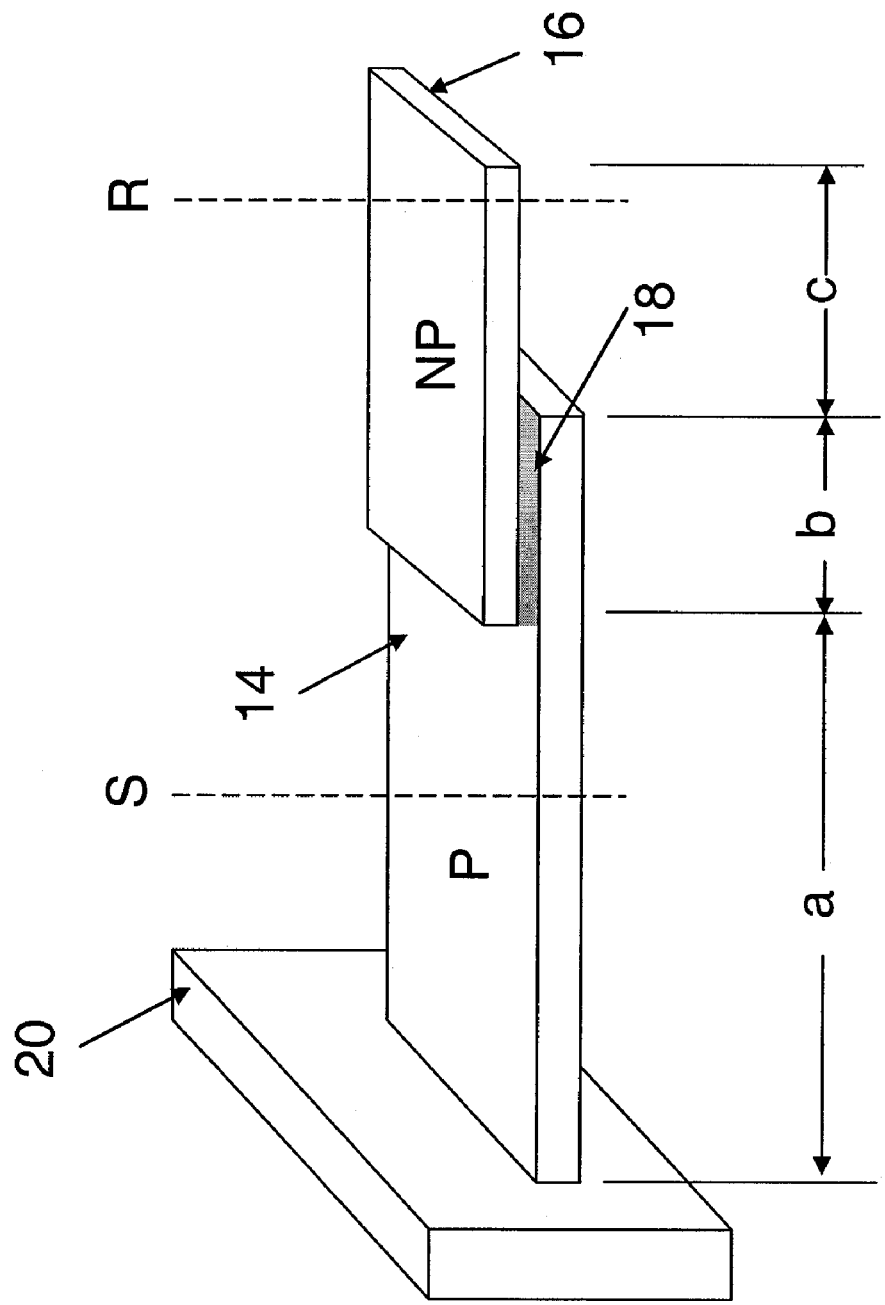
FIG. 19A shows a perspective view of a piezoelectric cantilever sensor useful in the methods of the present invention.

FIG. 19A shows an embodiment 710 of an unanchored, overhang piezoelectric cantilever sensor (oPEMC). This sensor 710 is termed, "unanchored" since the non-piezoelectric layer 16 is not attached to the base. This sensor is termed, "overhang" because the non-piezoelectric 16 layer extends beyond the distal tip of the piezoelectric layer 14 to create an overhanging portion of the non-piezoelectric layer 16 which is separated from the piezoelectric layer by overlap region 18. The base 20 serves to hold the proximate end of the piezoelectric layer 14.

The present invention encompasses sensors having parts of all suitable dimensions. For example, each of the piezoelectric layer 14, non-piezoelectric layer 16 and overlap region 18 may range from 0.1 to 10 mm in length. The width of the piezoelectric layer 14 and the non-piezoelectric layer 16 may range from 0.1 mm to 4 mm for the lengths given above. The width of the piezoelectric layer 14 may differ from the width of the non-piezoelectric layer 16 as well.

Typically an overhang piezoelectric cantilever sensor 710 has a non-piezoelectric layer 16 between about 0.1 mm and about 10.0 mm in length, and between about 0.1 mm and about 4.0 mm in width. The piezoelectric layer 14 may be between about 0.1 mm and about 10.0 mm in length, or between about 0.25 and about 4.0 mm in width. Layer 18 corresponds to the overlap between layer 14 and layer 16 and may be between about 0.1 mm and about 10 mm in length, or between about 0.1 and about 5.0 mm in length, depending on the specific construction of the overhang piezoelectric cantilever sensor.

The width of the overhang piezoelectric cantilever 710 sensor may be between about 0.1 mm and about 4.0 mm. The thickness of the piezoelectric cantilever 710 may be between about 0.1 mm and about 1.0 mm. Table 1 of FIG. 47 illustrates several example dimensions of overhang PEMC devices that correspond to FIG. 19A. In Table 1 of FIG. 47, the length dimensions a, b, and c correspond to those of FIG. 19A.

The overhang piezoelectric cantilever sensor 710 of the present invention generally exhibits a first bending mode resonance frequency mode peak at between 10-120 kHz, and a second bending mode resonance frequency mode peak at between 120 kHz-250 kHz.

Figure 19B:
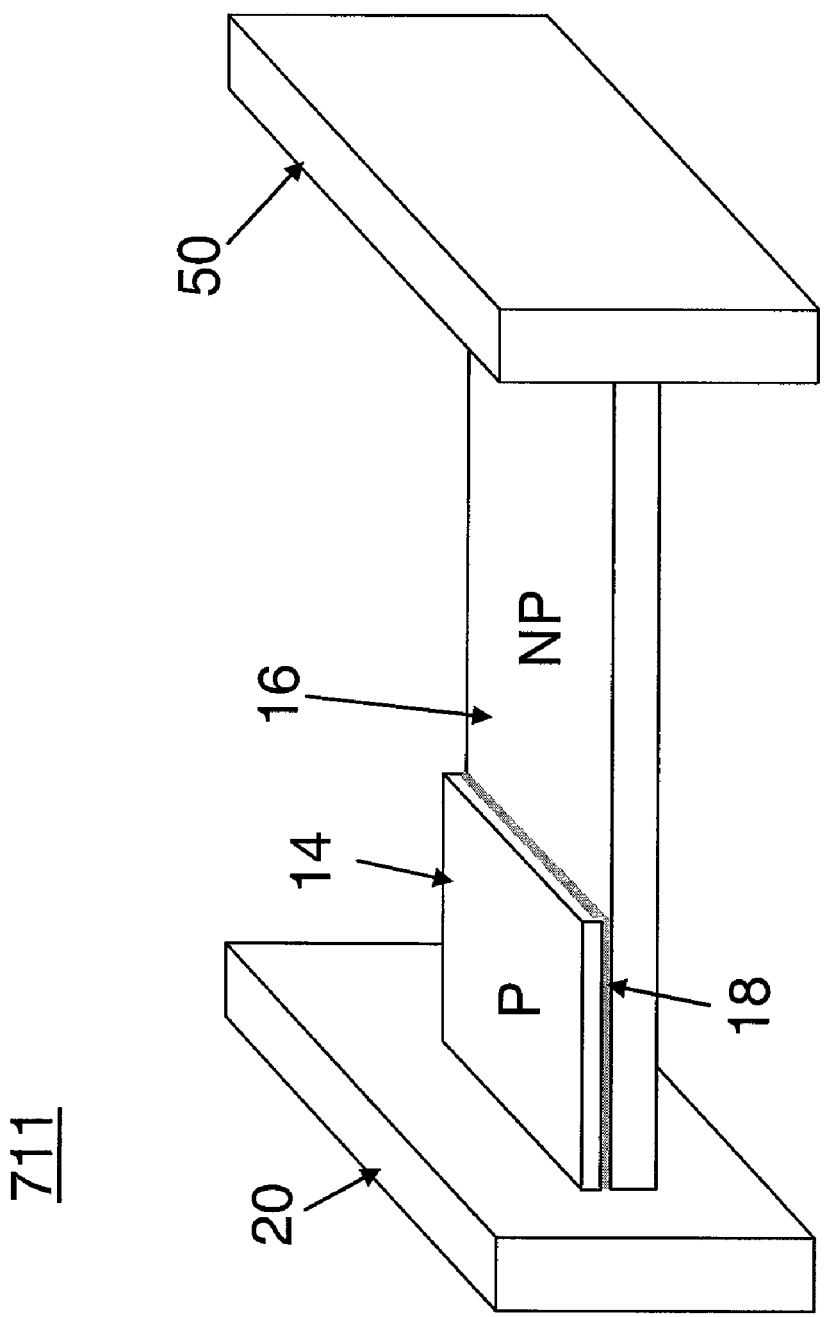
FIG. 19B shows an embodiment of an anchored piezoelectric-excited cantilever beam sensor useful in the methods of the present invention.
Figure 19C:
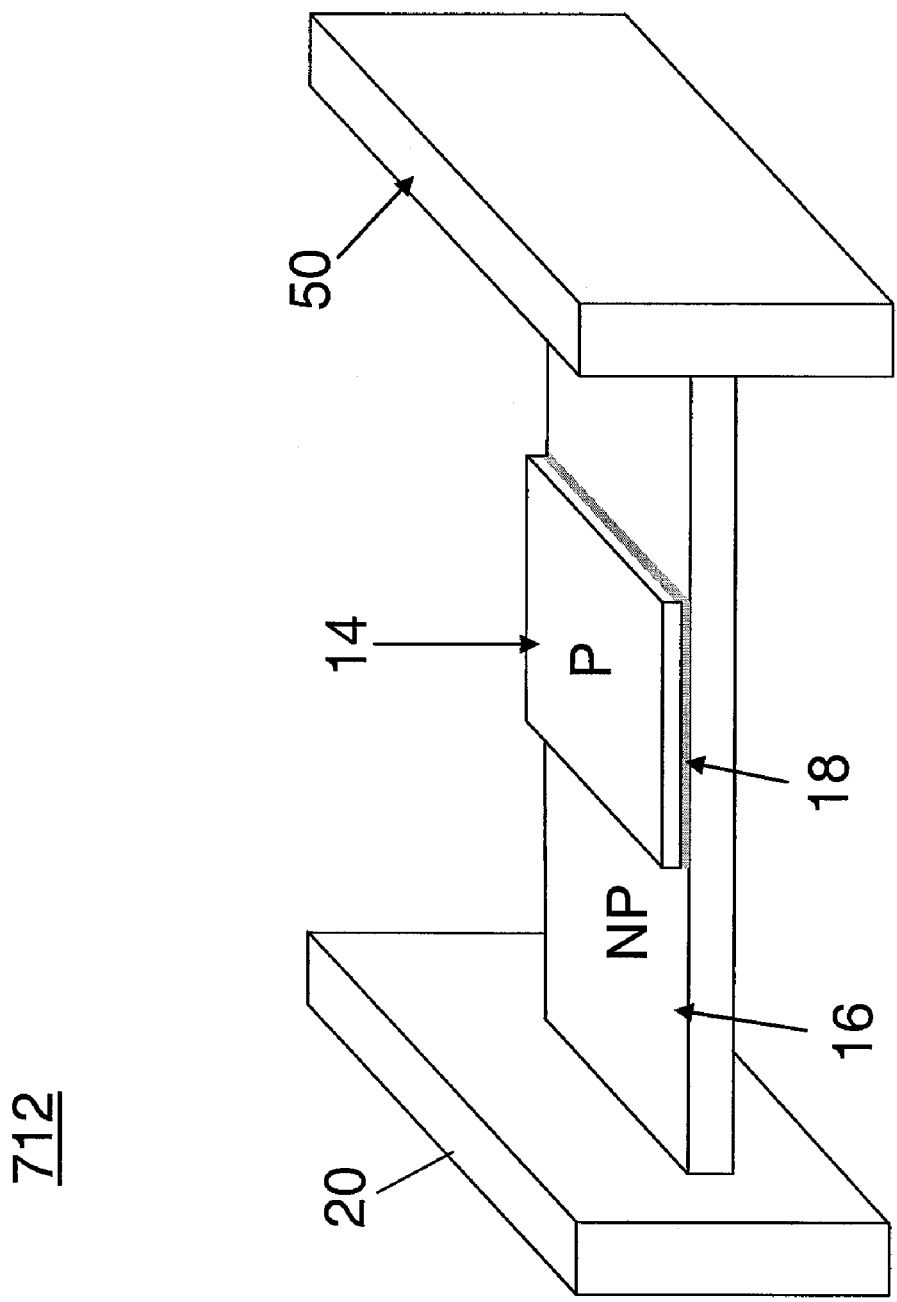
FIG. 19C shows an embodiment of a free-floating piezoelectric-excited cantilever beam sensor useful in the methods of the present invention.
Figure 19D:
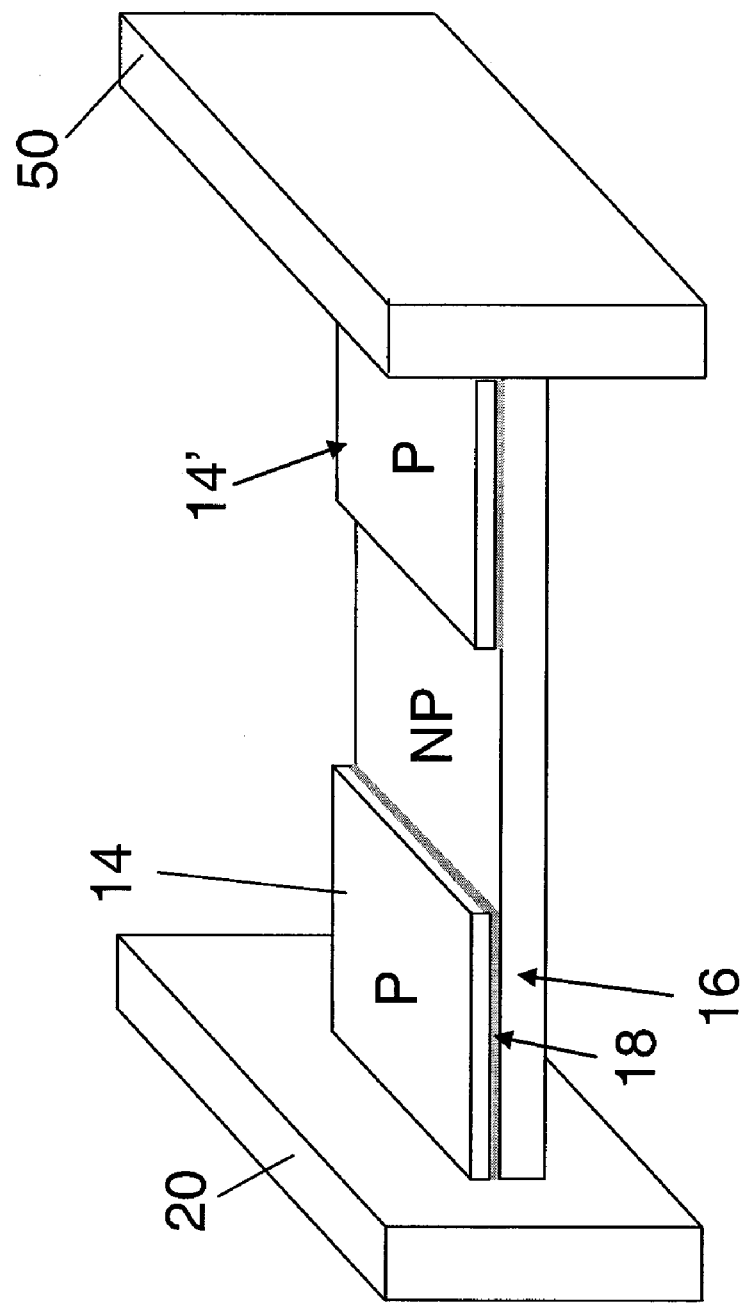
FIG. 19D shows an embodiment of an anchored bimorph piezoelectric-excited cantilever beam sensor useful in the methods of the present invention.
Figure 19E:
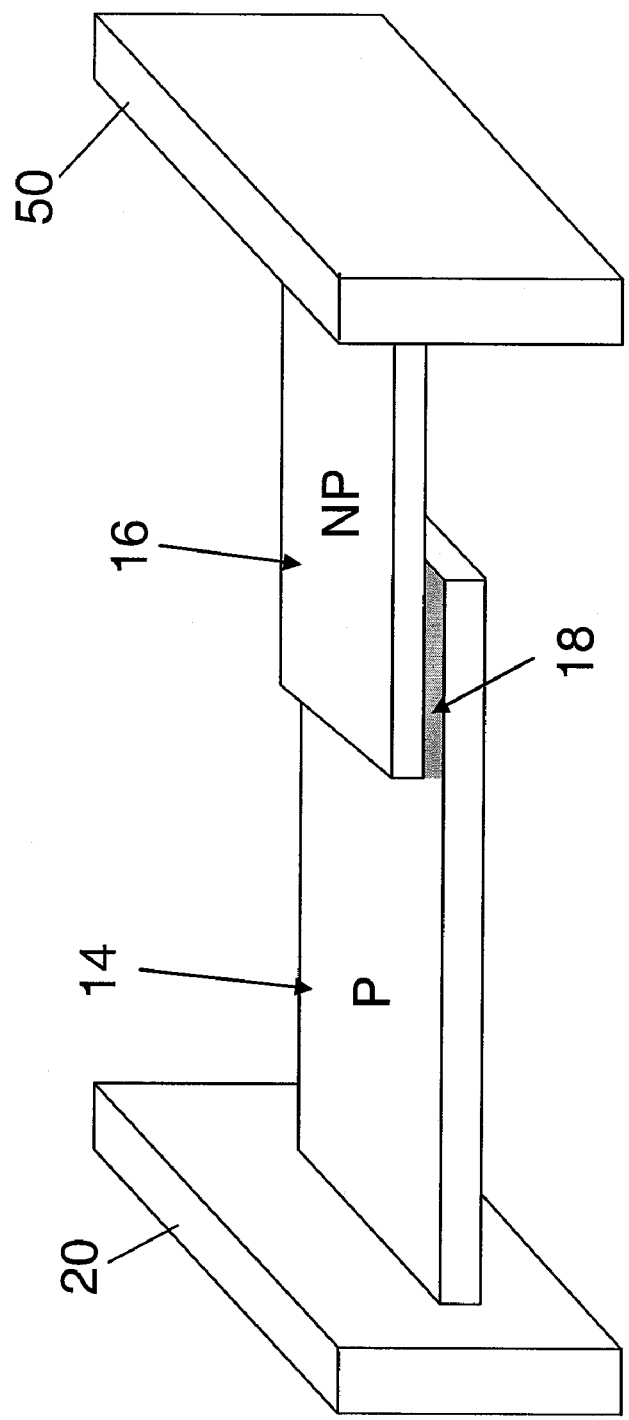
FIG. 19E shows an embodiment of an overhang piezoelectric-excited cantilever beam sensor useful in the methods of the present invention.

FIGS. 19B-19F show various embodiments of piezoelectric-excited cantilever beam sensors in accordance with the present invention, which have been demonstrated to also provide successful sensing responses. The cantilever beam sensors include all of the same elements as the overhang sensor of FIG. 19A, and, in addition, include a second base 50 to which at least one of the piezoelectric layer 14 and the non-piezoelectric layer 16 is also fixed. In FIGS. 19B-19D, the non-piezoelectric layer 16 is affixed to both bases (20, 50) to form the "beam". In FIG. 19E, the beam is formed by affixation of the piezoelectric layer 14 to the base 20, affixation of the non-piezoelectric layer 16 to the piezoelectric layer 14 via the adhesive layer 18 and affixation of the non-piezoelectric layer 16 to the base 50. In the configuration 717 of FIG. 19F, the beam is formed by affixation of the piezoelectric layer 14 to both bases (20, 50).

Anchoring of the two ends of the piezoelectric and non-piezoelectric layers was accomplished using a 3 mm glass or tungsten rod. As long as the bending modulus of the support rod is much larger than the sensor beam, one observes excellent peak shapes. Other suitable methods for anchoring can also be employed.

The design of the cantilever beam sensors of FIGS. 19B-19F is not intuitive since the expectation of a skilled person would be that affixation of both ends of the beam would provide a poor response as a result of the restrictions of the displacement of the cantilever as a result of its affixation to the bases (20, 50). In other words, in prior art cantilevers, one end of the cantilever was a free-end, i.e. not affixed to a base, in order to allow for a larger displacement of the cantilever during sensing in order to increase the response of the sensor.

Figure 19F:
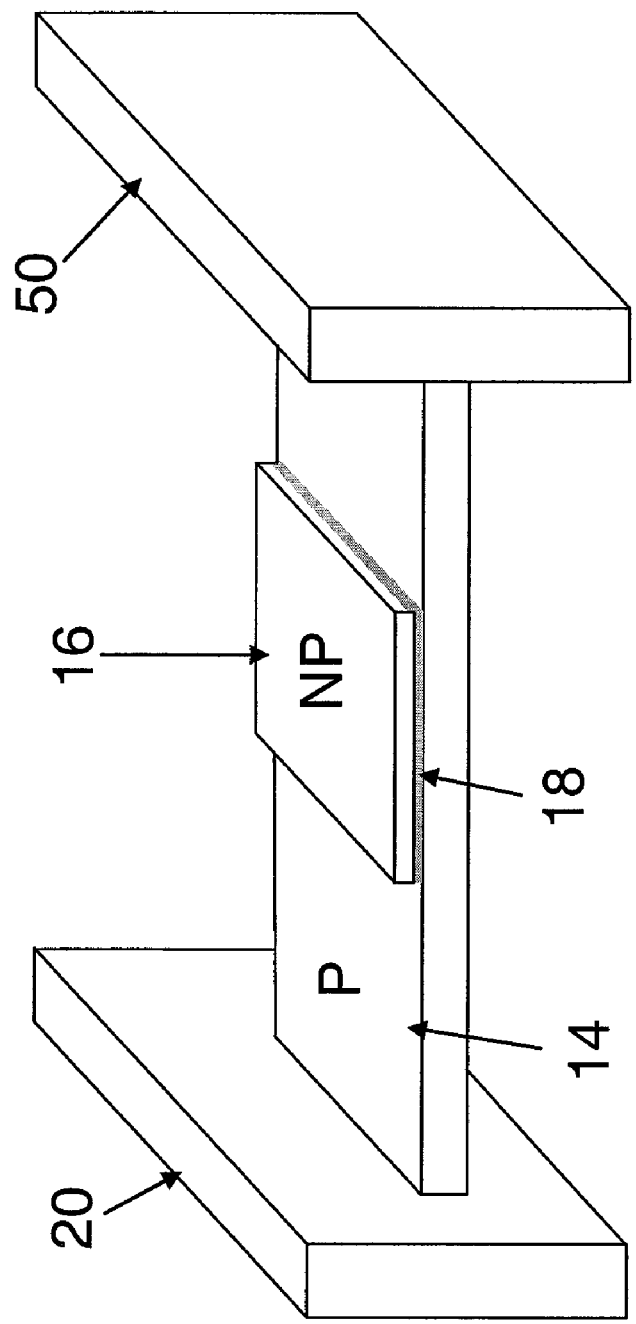
FIG. 19F shows an embodiment of an anchored lead zirconate titanate (PZT) piezoelectric-excited cantilever beam sensor useful in the methods of the present invention.
Figure 19G:
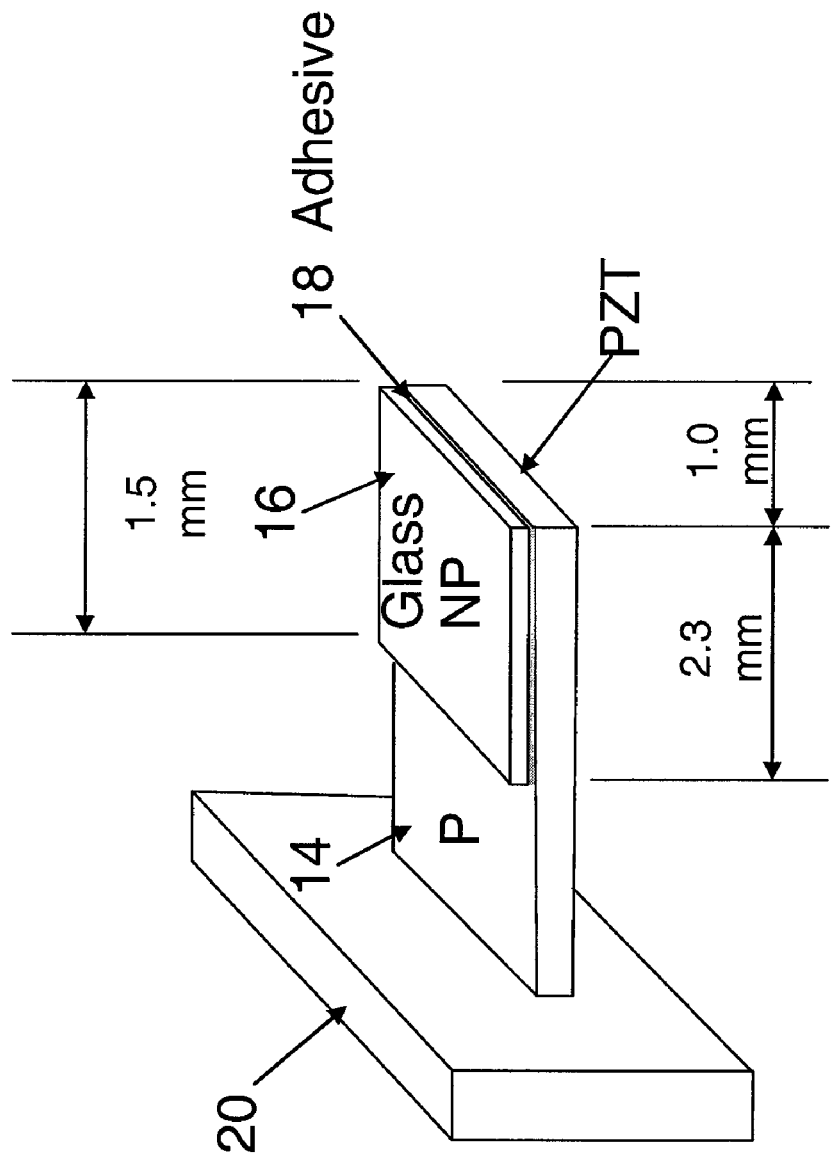
FIG. 19G shows a schematic of an embodiment of a free-floating tip PEMC (ftPEMC) sensor in accordance with the present invention.
Figure 20:
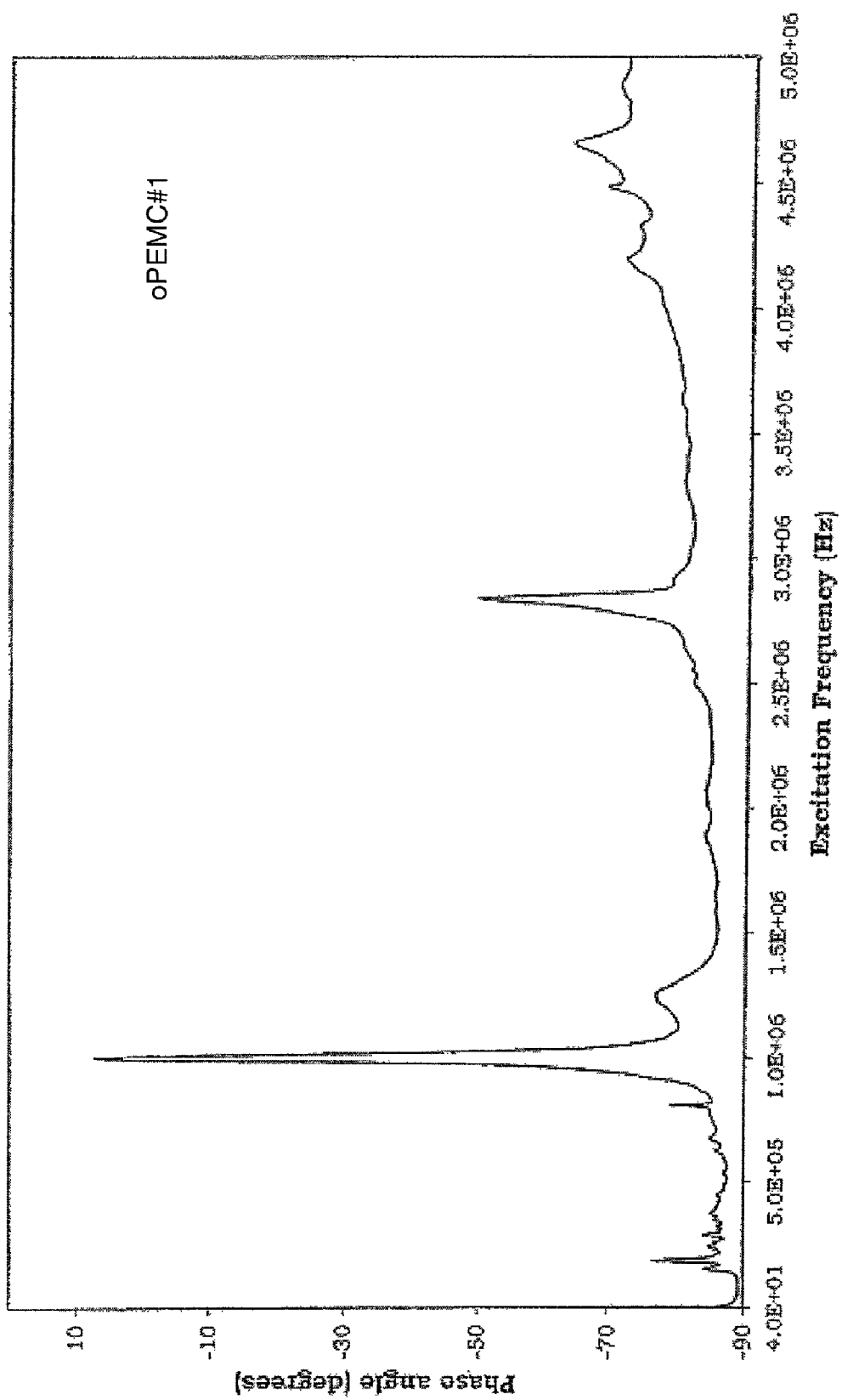
FIG. 20 is a resonance spectrum, in air, of a first embodiment of an overhang piezoelectric cantilever sensor, such as that shown in FIG. 1 (see oPEMC#1 from Table 1 of FIG. 47)

FIG. 19G depicts an alternative embodiment 719 to the overhang form of FIG. 19A termed a free-floating tip PEMC (ftPEMC) sensor. Unlike the sensors in FIGS. 19B-19F, the FIG. 19G construction has only one base 20 attachment. Performance results of this configuration and the other configurations are further discussed below.

Returning to the two base (20, 50) "beam" structures of FIGS. 19B-19F, it has been found that measurement of the stress in the piezoelectric layer, rather than the displacement of the piezoelectric layer, permits the use of cantilever "beam" sensors with both ends of the cantilever fixed to a base (20, 50). In addition, the cantilever beam sensors of the invention provide a higher fundamental mode (>100 kHz), stable and robust performance under flow conditions, and excellent mass change sensitivity which permits low sample concentration detection.

One advantage of the current invention is that the above FIGS. 19A-19G designs are mechanically robust and withstand flow conditions with minimal deterioration in performance. A second advantage is that the fundamental frequency is three to four times higher than a sensor of similar dimensions in a cantilever configuration.

FIGS. 20-31, discussed below, show the results of various experiments conducted with different embodiments of overhang Piezoelectric-Excited Millimeter-sized Cantilever (oPEMC) sensors in accordance with the present invention. Table 1 of FIG. 47 presents dimensions and resonant frequencies of overhang PEMC (oPEMC) devices. FIG. 2 shows the typical resonance spectrum of a first embodiment of an overhang piezoelectric cantilever sensor, such as shown in FIG. 19A, operated in air (see oPEMC#1 of Table 1 of FIG. 47). A plot of phase angle versus excitation frequency, at an excitation voltage of 100 mV is shown in FIG. 2. The first resonance frequency mode typically occurred between 150 and 200 kHz and the second resonance frequency mode occurred between 250 and 300 kHz. The resonance spectrum shows higher order characteristic peaks at approximately 980 kHz, 2.90 MHz and 4.60 MHz for a composite PZT cantilever that is 2 mm in width. As compared to a similar, unanchored piezoelectric cantilever configuration without an overhang, the base line up to 5 MHz was slightly more stable and the majority of the observed resonance frequencies were higher. Additionally, the quality factor (Q) of the 980 kHz characteristic peak was three times higher for the overhang embodiment, and the quality factor (Q) of the 4.60 MHz characteristic peak is a factor of two lower.

Figure 21:
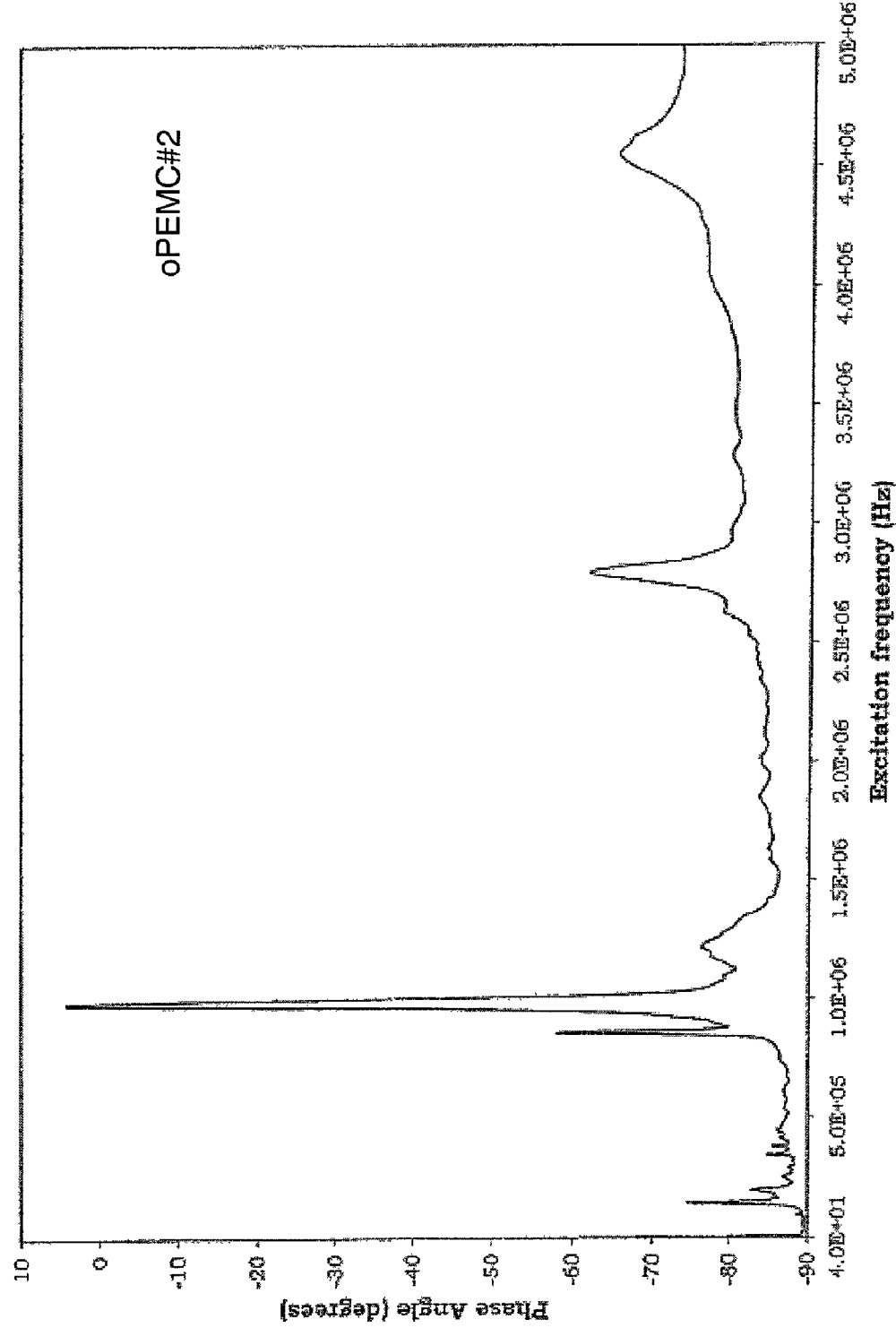
FIG. 21 is a resonance spectrum, in air, of a second embodiment of an overhang piezoelectric cantilever sensor shown in FIG. 1 (see oPEMC#2 from Table 1 of FIG. 47)

FIG. 21 shows a typical resonance spectrum of a second embodiment of an overhang piezoelectric cantilever sensor shown in FIG. 19A, operated in air (see oPEMC#2 from Table 1 of FIG. 47). FIG. 21 shows a plot of phase angle versus excitation frequency, at an excitation voltage of 100 mV. The first resonance frequency mode typically occurred between 150 and 200 kHz and the second resonance frequency mode occurred between 250 and 300 kHz. The resonance spectrum for this second embodiment of the overhang piezoelectric cantilever sensor shows higher order characteristic peaks at approximately 980 kHz, 2.90 MHz and 4.60 MHz for a composite PZT cantilever that is 2 mm in width. The overhanging portion, section 16 of FIG. 19A of this embodiment of the overhang piezoelectric cantilever sensor, is three times larger than the overhanging portion of oPEMC#1, which may have caused some attenuation of the first resonance frequency mode and the resonance frequency mode that occurred between 850-900 kHz.

Figure 22:
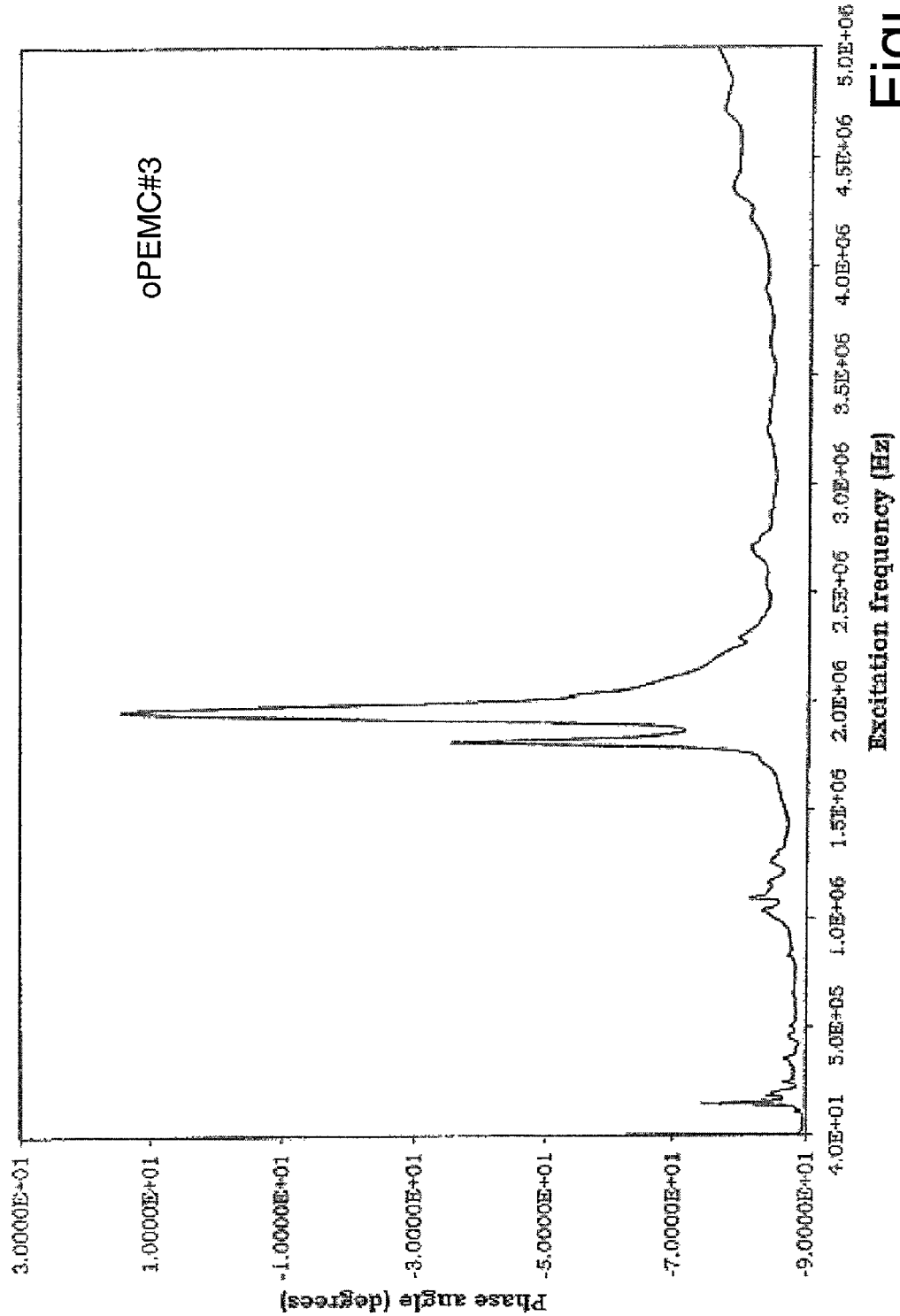
FIG. 22 is a resonance spectrum, in air, of a third embodiment of an overhang piezoelectric cantilever sensor shown in FIG. 1 (see oPEMC#3 from Table 1 of FIG. 47)

FIG. 22 shows the resonance spectrum of a third embodiment of an overhang piezoelectric cantilever sensor, operated in air (see oPEMC#3 from Table 1 of FIG. 47). FIG. 22 shows a plot of phase angle versus excitation frequency, at an excitation voltage of 100 mV. The first resonance frequency mode typically occurred between 150 and 200 kHz, with no apparent second resonance frequency mode. The resonance spectrum for this embodiment of the overhang piezoelectric cantilever sensor shows higher order characteristic peaks at approximately 1.81 MHz and 1.95 MHz for a composite PZT cantilever that is 1 mm in width. As compared to an unanchored configuration without overhang, the resonant peak for the overhang configuration at 1.81 MHz becomes defined while all other peaks beyond 2.5 MHz become dampened.

Figure 23:
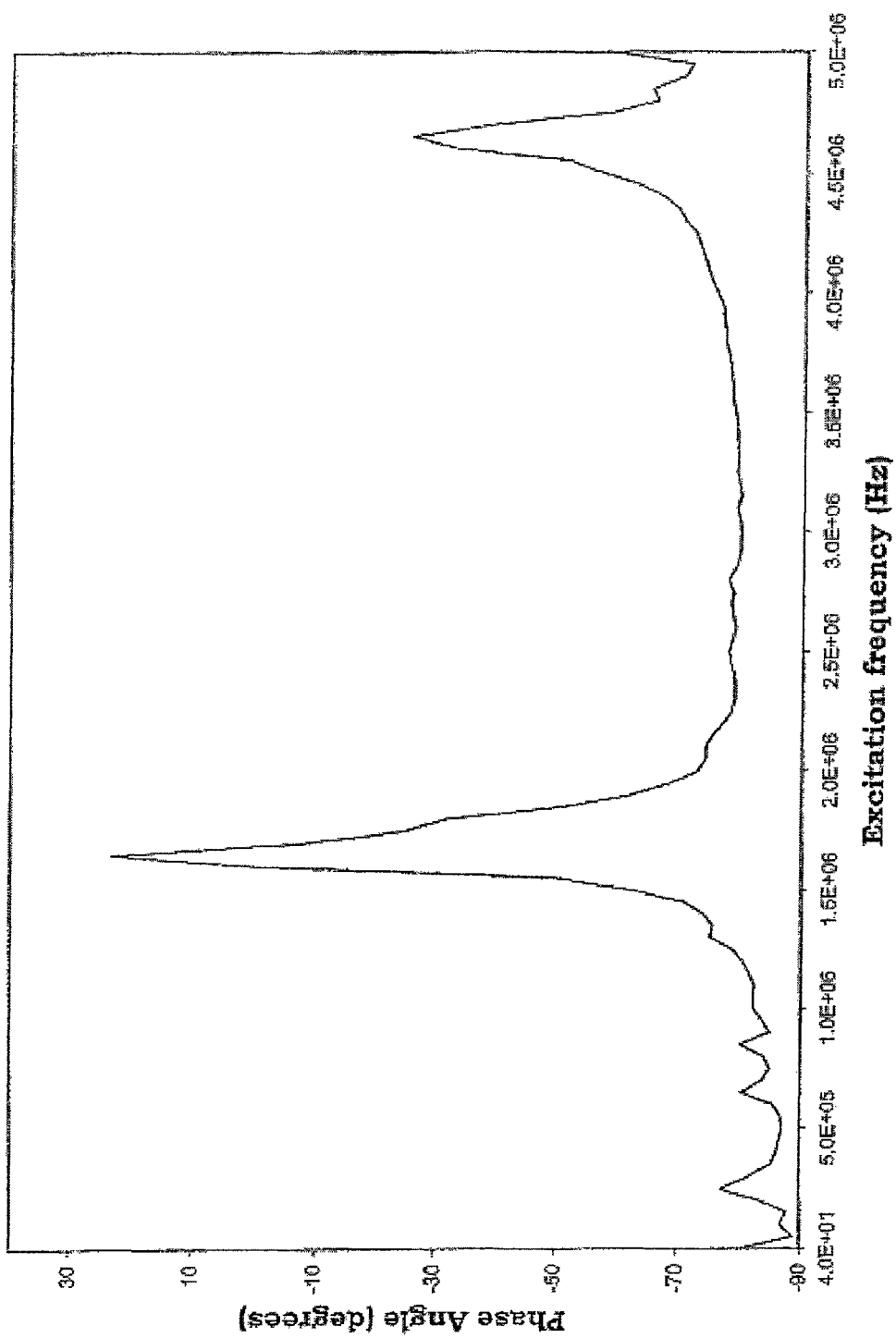
FIG. 23 is a resonance spectrum of a fourth embodiment of an overhang cantilever sensor as shown in FIG. 1 (see oPEMC#4 from Table 1 of FIG. 47)

FIG. 23 shows the resonance frequency spectrum of a fourth embodiment of an overhang piezoelectric cantilever in accordance with the present invention (see oPEMC#4 from Table 1 of FIG. 47). The resonance frequency spectrum of FIG. 23 was obtained using a 1 mm wide overhang cantilever with a piezoelectric layer constructed of ceramic PZT. The spectrum was obtained in air using a 100 mV signal to excite the cantilever. Characteristic peaks were obtained at 250 kHz, 650 kHz, 850 kHz, 1.65 MHz, and 4.65 MHz.

Figure 24:
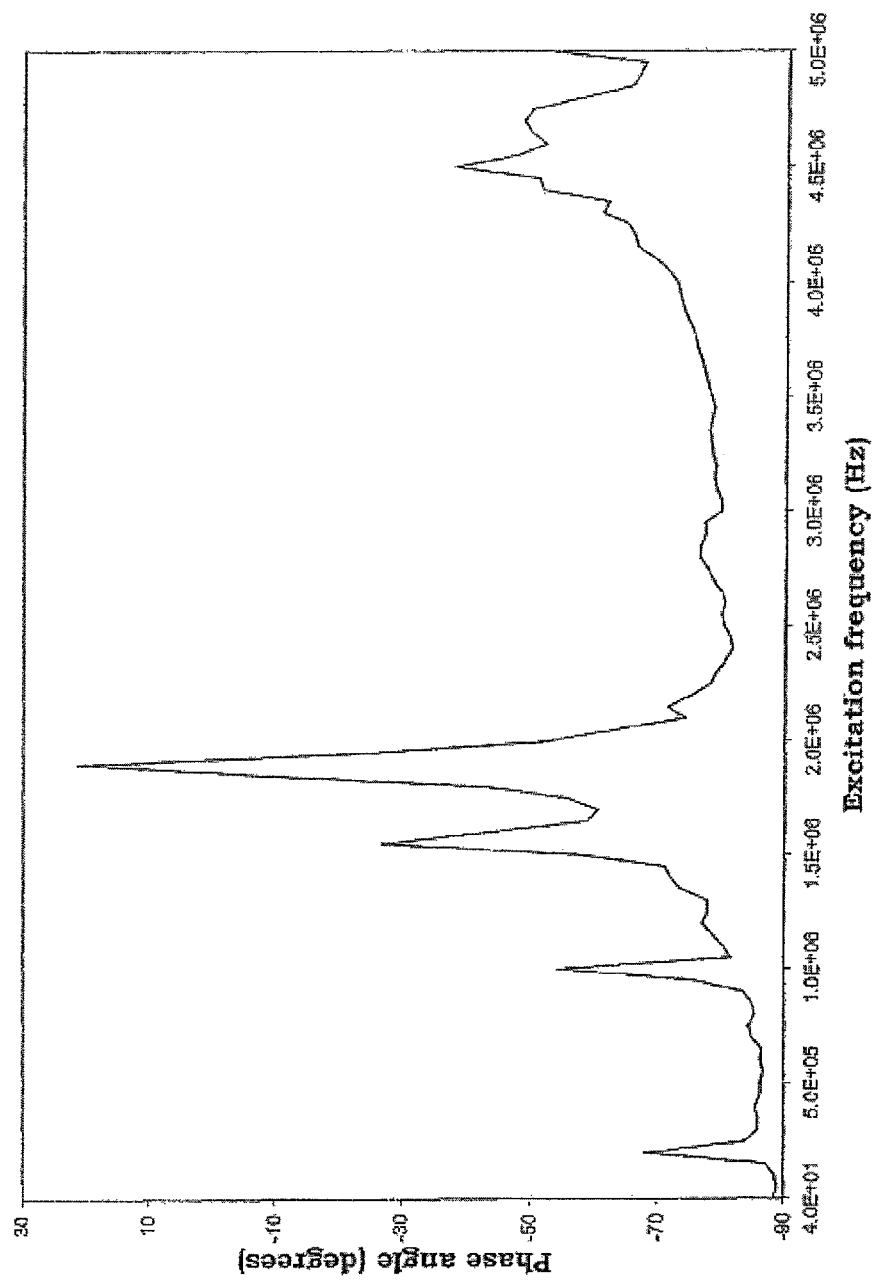
FIG. 24 is a resonance spectrum of a fifth embodiment of an overhang cantilever sensor as shown in FIG. 1 (see oPEMC#5 from Table 1 of FIG. 47)

FIG. 24 shows the resonance frequency spectrum of a fifth embodiment of an overhang piezoelectric cantilever in accordance with the present invention (se oPEMC#5 from Table 1 of FIG. 47). The resonance frequency spectrum of FIG. 24 was created using a 1 mm wide overhang cantilever with a piezoelectric layer constructed of ceramic PZT. By shortening section (a) of the cantilever, more attenuated peaks were obtained for all listed frequencies. The spectrum was obtained in air using a 100 mV signal to excite the cantilever. Characteristic peaks were obtained at 200 kHz, 1.0 MHz, 1.55 MHz, 1.90 MHz, and 4.50 MHz. Additionally, the dimensions of this embodiment the overhang piezoelectric cantilever gave rise to a sensitive, resonant mode at 1.00 MHz.

In one embodiment, the piezoelectric cantilever sensors were fabricated from quartz silica and either piezoelectric ceramic lead zirconate and titanate (PZT) or piezoceramic-polymer 1-3 fiber composite. In one embodiment, the non-piezoelectric layer was constructed out of conventional materials such as ceramics, metals, polymers and composites of one or more of ceramics, metals, and polymers, such as silicon dioxide, copper, stainless steel, and titanium.

Table 2 of FIG. 48 shows the quality factor (Q) of the corresponding resonant peaks listed in Table 1 of FIG. 47 for the different piezoelectric cantilever sensors. The quality factors were determined as a ratio of the resonant frequency to the peak width at half the peak height. As a result, the quality factor is a measure of the sharpness of the resonant peaks. It has been shown in the experiments above that the quality factors of overhang piezoelectric cantilever sensors do not decrease significantly when the sensors are placed in different environments ranging from vacuum to air flow environments.

It is observed that the Q values for overhang piezoelectric cantilever sensors typically range between 10 and 70, depending upon the respective frequency mode where the peak is detected. The overhang piezoelectric cantilever sensors, when used in vacuum, air, and viscous environments, including flows, typically do not have more than a 20%-35% decrease in Q value.

Figure 25:
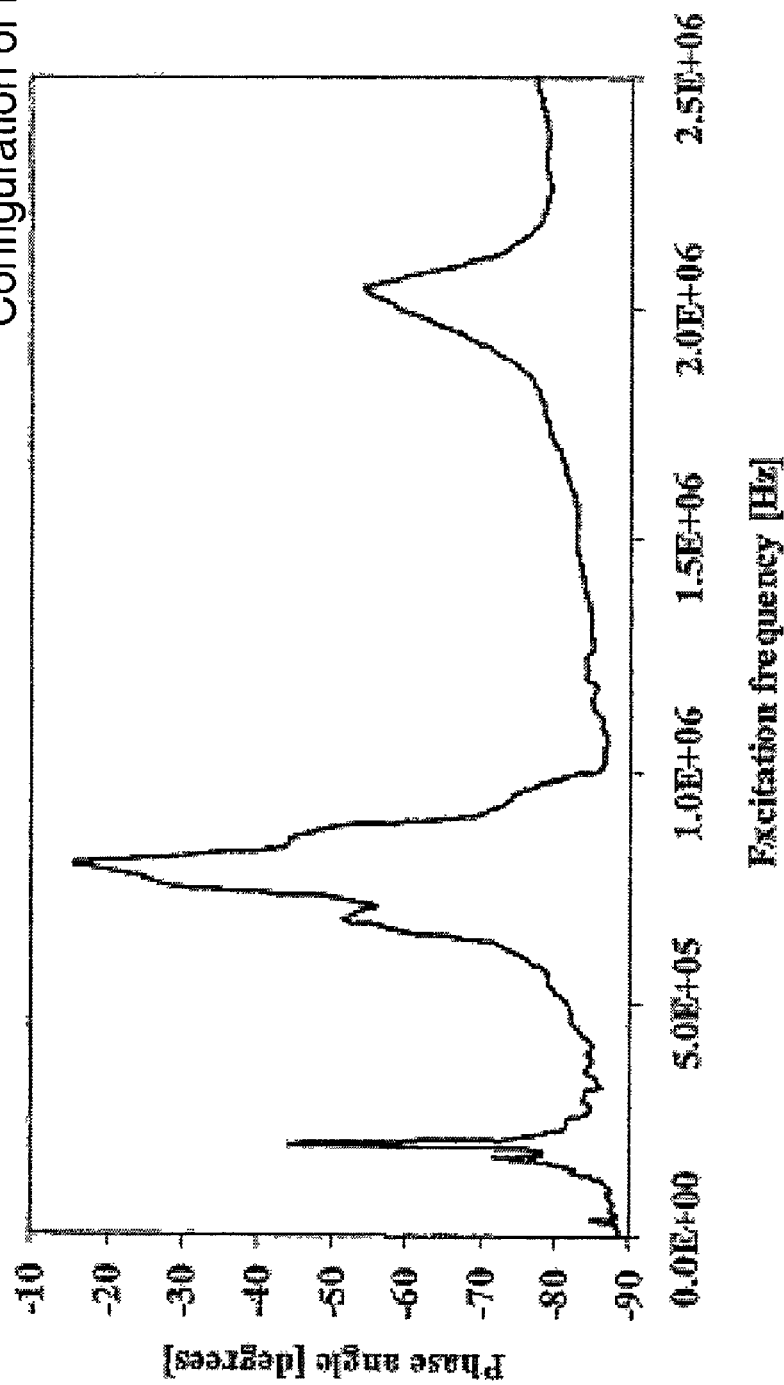
FIG. 25 shows a resonance spectrum plot of phase angle versus excitation frequency, in air of the anchored PEMCB sensor (aPEMCB, FIG. 19B) excited at 100 mV.

The performance of the configurations of FIGS. 19B-19F are now considered. FIG. 25 shows a typical resonance spectrum, plot of phase angle versus excitation frequency, in air of the anchored Piezoelectric-Excited Millimeter-sized Cantilever Beam (aPEMCB) sensor 711 of FIG. 19B excited at 100 mV. The first peak is the fundamental resonant mode, which typically occurred in the frequency range 200 to 300 kHz. The second peak is the second resonant mode, which is usually in the frequency range 700 kHz to 1 MHz. The aPEMCB resonant spectrum was measured by connecting the electrodes to an impedance analyzer (Agilent, HP4192A) that was interfaced to a personal computer for continuous measurement of impedance, phase angle and amplitude ratio in the frequency range of interest with an excitation voltage of 100 mV.

Figure 26:
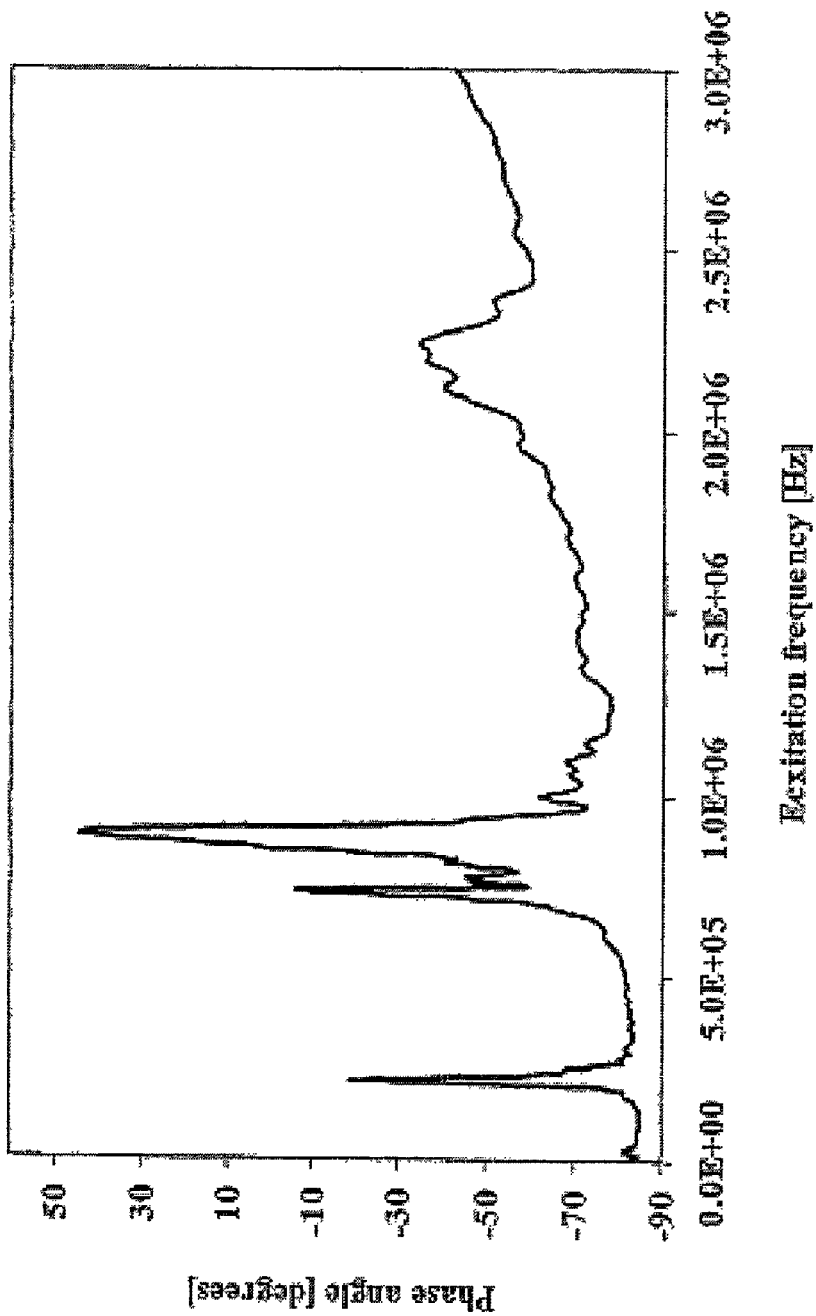
FIG. 26 shows the resonance characteristics of the free-floating PEMCB (fPEMCB#1, FIG. 19C) sensor in air, using a plot of phase angle versus excitation frequency, at an excitation voltage of 100 mV.

FIG. 26 shows the resonance characteristics of the free-floating Piezoelectric-Excited Millimeter-sized Cantilever Beam (fPEMCB#1) sensor 712 of FIG. 19C, in air, using a plot of phase angle versus excitation frequency, at an excitation voltage of 100 mV. Typically, the fundamental resonance mode occurred between 200 kHz and 250 kHz, and the second mode frequency occurred between 800 kHz and 1 MHz. The quality factor for each resonant peak is list in Table 4 of FIG. 50.

Figure 27:
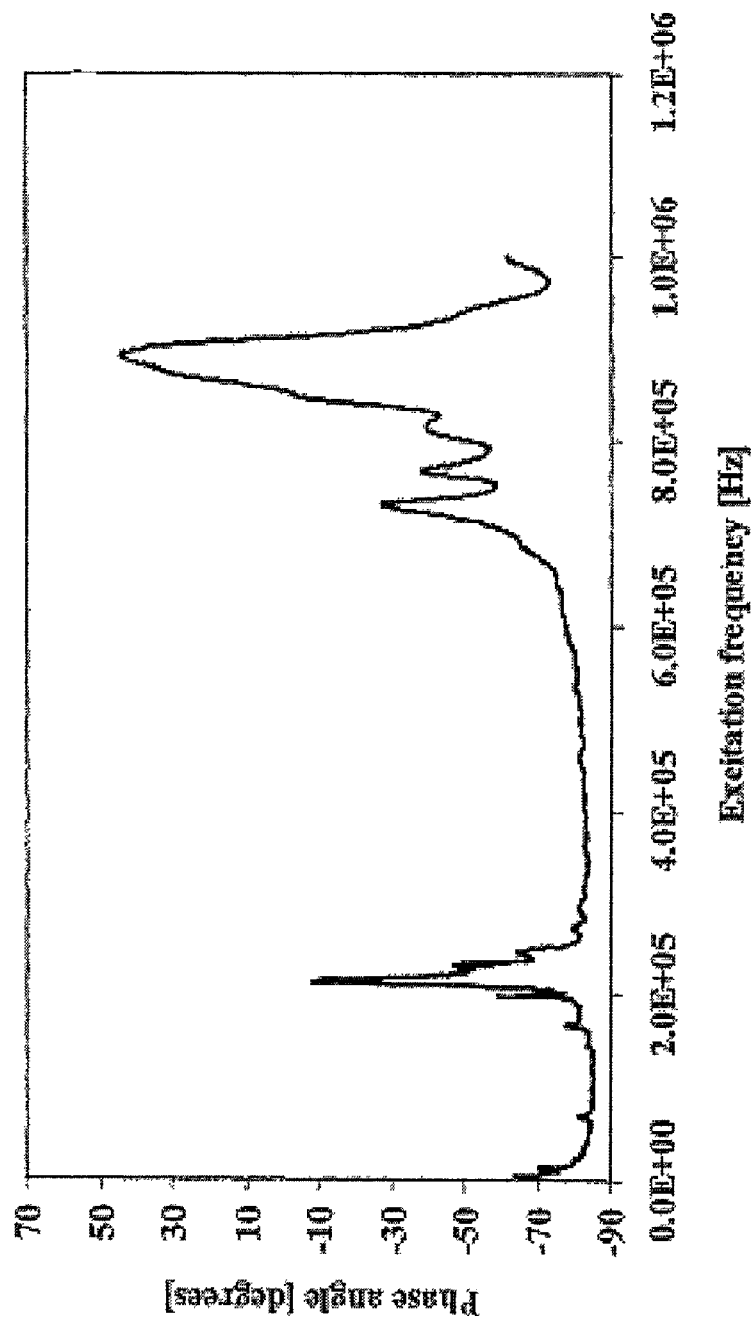
FIG. 27 shows a resonance spectrum of the anchored bimorph PEMCB (abPEMCB#1, FIG. 19D) sensor in air, using a plot of phase angle versus excitation frequency, at an excitation voltage of 100 mV.

FIG. 27 shows a typical resonance spectrum of the anchored bimorph Piezoelectric-Excited Millimeter-sized Cantilever Beam (abPEMCB#1) sensor 713 of FIG. 19D, in air, using a plot of phase angle versus excitation frequency, at an excitation voltage of 100 mV. The fundamental resonant frequency occurred at 200 kHz and the second mode at 700 kHz. The physical dimensions and quality factors for all of the sensor construction types are provided in Tables 3 and 4, respectively.

Figure 28:
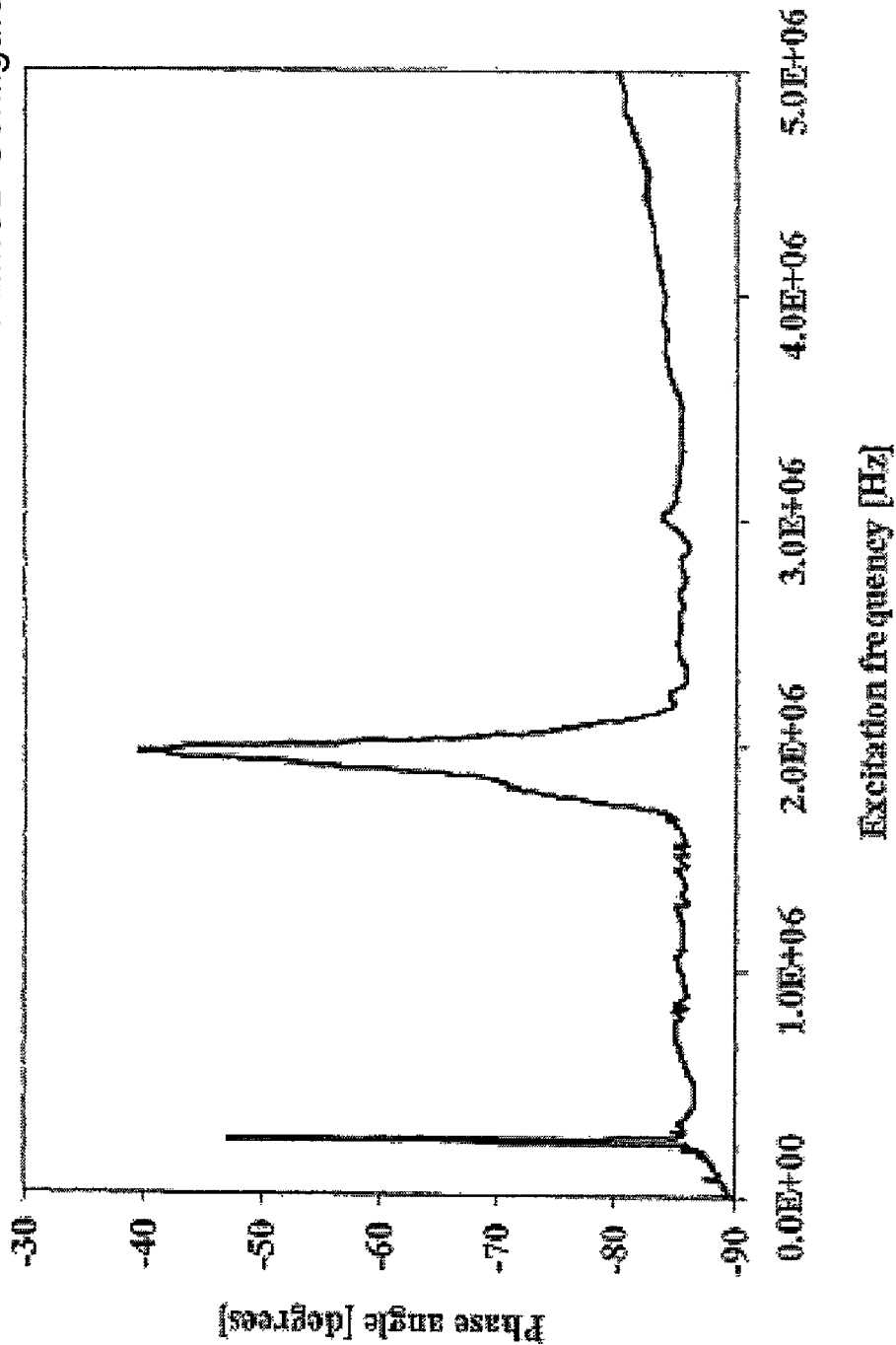
FIG. 28 shows the resonance spectrum of an overhang PEMCB (oPEMCB#1), FIG. 19E) sensor in air excited at a voltage of 100 mV.

FIG. 28 shows the resonance spectrum of an overhang beam PEMCB (oPEMCB#1) sensor 715 of FIG. 19E, in air, excited at a voltage of 100 mV. The dimensions and resonant frequencies of the anchored, free-floating, and anchored bimorph and overhang PEMC sensors of FIGS. 19B, 19C, 19D and 19E respectively are tabulated in Table 3 of FIG. 49. Here, it is seen that by varying the geometry of the PEMCB sensors, the peak positions of resonant frequencies can be tailored to specific needs. Thus, the position of the piezoelectric layer 14 and non-piezoelectric layer 16, as well as those layers being anchored or unanchored to the beam bases 20, 50, as well as the selection of which material comprises the beam allows a wide range of selection of resonant frequencies for determination of biological or chemical detection.

Table 3 of FIG. 49 shows the physical dimensions of the PEMCB sensors used in FIGS. 25-28 in millimeters and the resonant frequency of the dominant modes in air. The length of PZT and glass is the dimension of the layer 14 and 16 respectively in FIGS. 19B-19F. The width and thickness is the dimension of each layer. The PEMCB sensors were fabricated from piezoelectric ceramic lead zirconate and titanate (PZT) and quartz silica.

Another type of PEMC sensor having a different geometry from the dual-base cantilever beam devices just described is shown in FIG. 19G and was also fabricated and tested. The new geometry 19, a free-floating tip PEMC sensor, (ftPEMC) was fabricated using a 127 μm thick PZT single sheet, and a 180 μm thick quartz cover square. The PZT layer used is that same as the base sensor platform of FIG. 19A. The cantilever free end was designed with the glass layer, 1.50±0.05×1±0.05 mm² (length×width), bonded at one end of the PZT layer, 4±0.05×1±0.05 mm (length×width), by a non-conductive adhesive. At the other end, 1.70±0.05 mm length of the PZT layer was epoxied into a glass tube. As a result, the cantilever free end has 0.8 mm of exposed PZT layer. Top and bottom electrodes were made on the 1.7 mm long PZT layer, before it was epoxied, using a 30 gauge copper wire soldered to BNC couplers. The PZT layer at the cantilever free end was insulated with an 8 μm thick polyurethane layer. The glass layer, 1.5±0.05×1±0.05 mm², provides a surface for antibody immobilization and antigen detection.

Any of the above-described PEMC or PEMCB devices can result in the formation of a sensor if a recognition entity, such as an antibody or a DNA, is coated on the surface of the PEMC or PEMCB device. With the proper coating, the resulting sensor coating will attract and bond to a targeted analyte, which may be an airborne pathogen, an airborne protein, or an airborne biological agent. In one embodiment, the direct detection of airborne *Bacillus anthracis* (BA) spores was explored using millimeter-sized PZT cantilever sensors (PEMC) coated with an immobilized BA antigen. The attachment of BA on the coated PEMC sensor is detected as a frequency change in the PEMC device due to the added mass of the BA because the attached BA affects the mass, and thus the mechanical resonance, of the cantilever device In one embodiment, an experimental apparatus included a horizontal tube with the PEMC sensor suspended vertically with its glass surface facing the air flow. The quartz surface was silanylated followed by immobilization of rabbit Anti-BA specific for the pathogen BA before exposure to a flowing air stream (11 cm/s) containing 42 to 278,000 spores/L-air. The BA was introduced upstream of the sensor using an axial flow nebulizer. The concentration of the BA solution in the nebulizer was measured using a Coulter Counter Multisizer II. The sensor was fabricated from a 2×5 mm PZT laminated with a 0.5 mm offset to 2×5 mm borosilicate glass anchored in a non-conductive epoxy base.

Figure 29A:
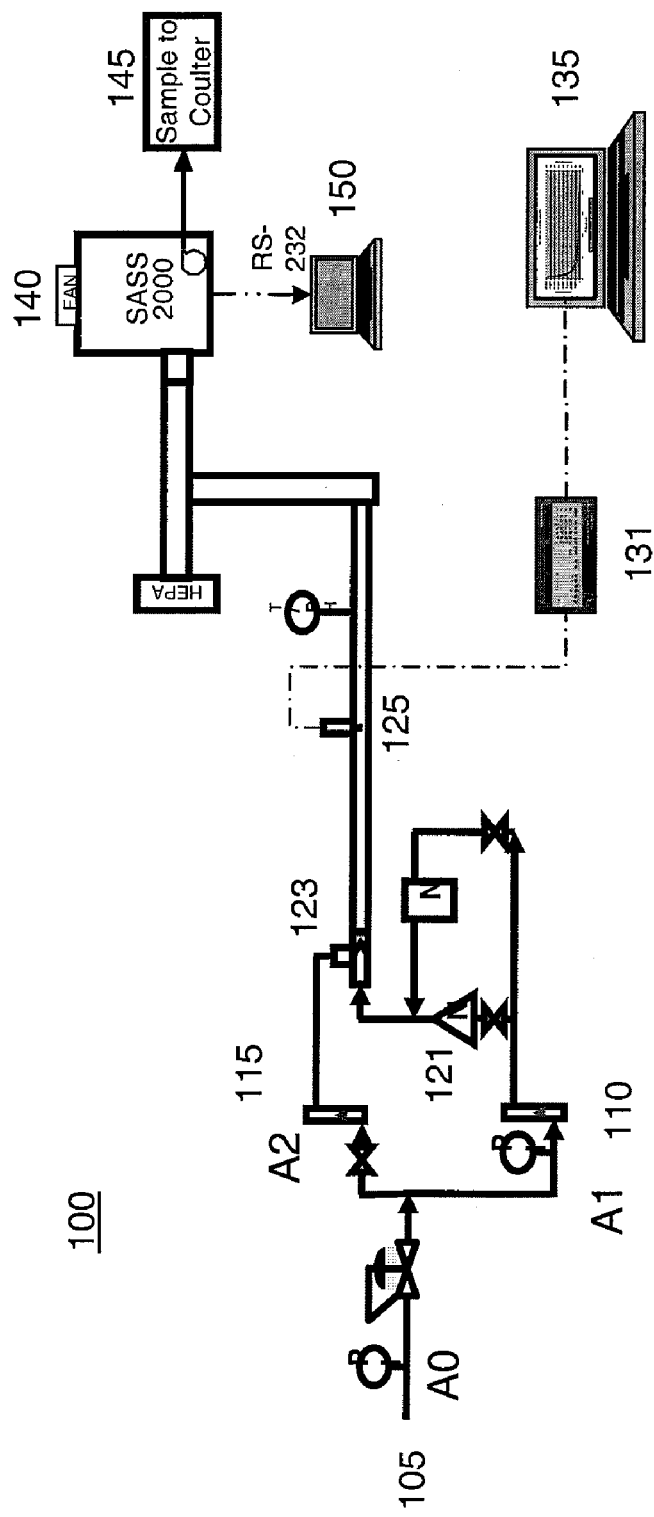
FIGS. 29A-B show an apparatus used to implement airborne *Bacillus anthracis* detection.
Figure 29B:
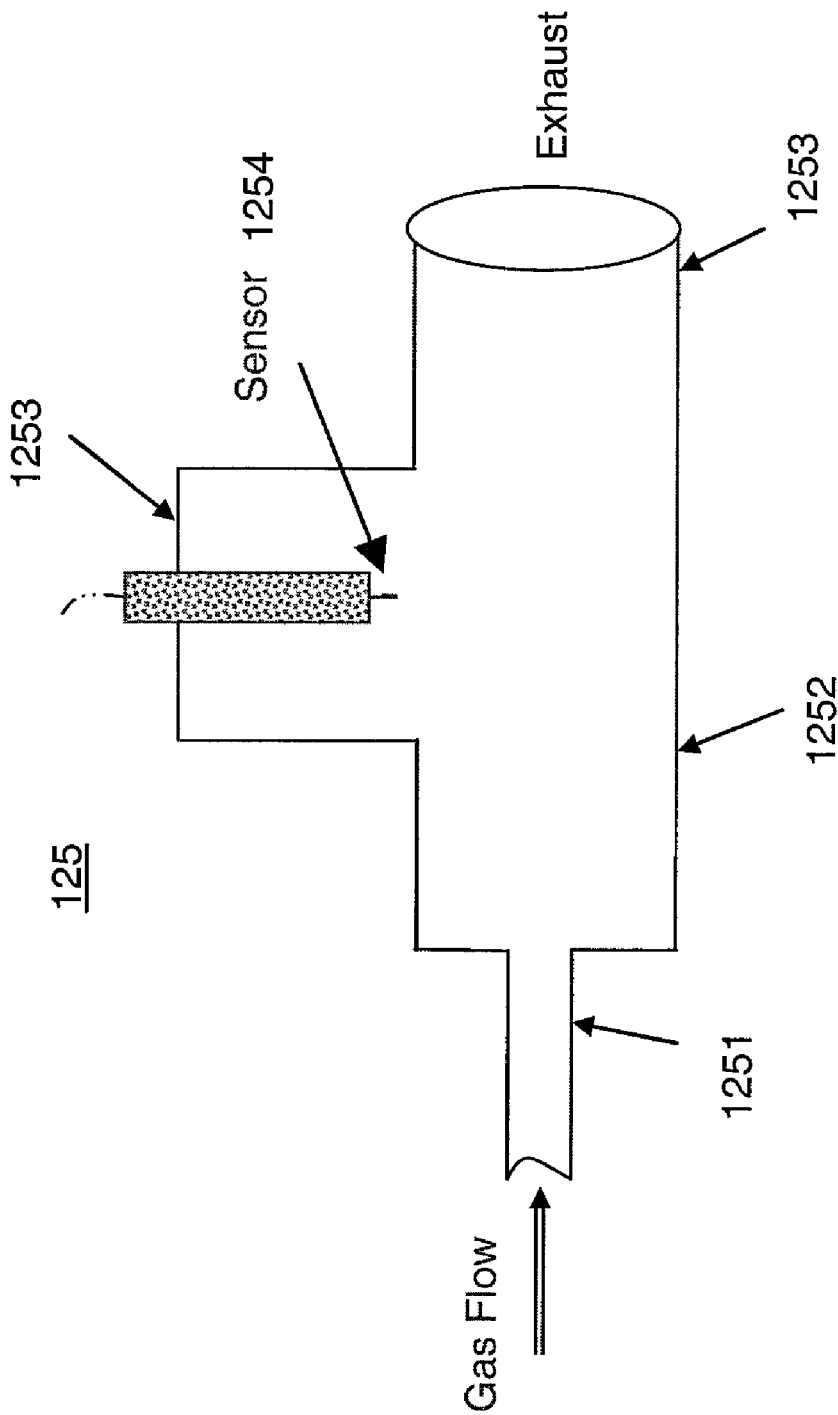

FIG. 29A shows the apparatus 100 used to flow airborne *Bacillus anthracis* (BA) to PEMC-type sensor for detection of airborne BA. Supply air 110 (A0) conditioned to zero humidity is split into two streams. One stream uses air valve 110 (A1) and is used to feed nebulizer 121 a known concentration of BA in deionized water. The nebulizer 121 produces liquid particles of about 5 microns in size. A low shear nebulizer is used to prevent damage to the BA spores as they flow through the nebulizer. The liquid particles are carried by make-up air from adjustable air valve 115 (A2) which is adjustable from about 1-200 lpm though a 2" pipe. In the configuration of FIG. 29A, the two streams are mixed at mixer 123 and carry the aerosolized BA at a 1 m/s velocity although higher velocities are possible. The PEMC sensor is inserted in a "T-shaped" exposure tube assembly 125 in an orthogonal fashion, as shown in FIG. 29B, is interfaced to an impedance analyzer 131 and a personal computer 135 that collects resonant frequency data every 30 seconds. The humidity and temperature of the flowing Bio-aerosol is continuously monitored. Periodically, the exit stream is sampled using a commercial SASS 2000 air sampler 140, which provides a 5 ml liquid sample. These samples were either analyzed using a PEMC sensor in a separate apparatus or its particle size and distribution is determined using a Coulter counter. The SASS 2000 air sampler is monitored using an RS-232 interface to a personal computer 150.

Flow cell 125 in FIG. 11B comprises a gas flow input portion 1251, a gas flow body portion 1252, an exhaust opening portion 1253, and a sensor mounting portion 1253. The sensor 1254 in the sensor mounting portion may be variably positioned in a vertical direction to adjust the depth of penetration if the sensor into the airflow through the body 1252. In one embodiment, the sensor is oriented to expose the recognition entity of the cantilever sensor orthogonally to the direction of airflow to maximize exposure of the recognition entity to elements in the airflow.

Using the configuration of FIG. 29A, a steady state frequency response of the sensor was achieved initially by flowing humid air (RH=85±3% and T=23±0.3 degrees C.) at a flow rate of 2.4 lpm. Nebulizer charge was 10 million spores in 4 mL and nebulized for 15 minutes which yielded gas phase concentration of 278,000 spores/L of air. The frequency of a PZT cantilever is a function of its mass and temperature, and the fluid dynamic properties of the surrounding gas. Upon exposure to airborne BA, resonance frequency decreased 700 Hz due to spore attachment to the coated cantilever device. Post-detection, the sensor was immersed in PBS for confirmation of BA attachment by releasing the attached BA using a low pH buffer. The frequency change resulting from the release of the spores was 350 Hz. The frequency change due to temperature and moisture effects were 60 Hz per degree C. and 2 Hz per % of relative humidity (RH).

Figure 30A:
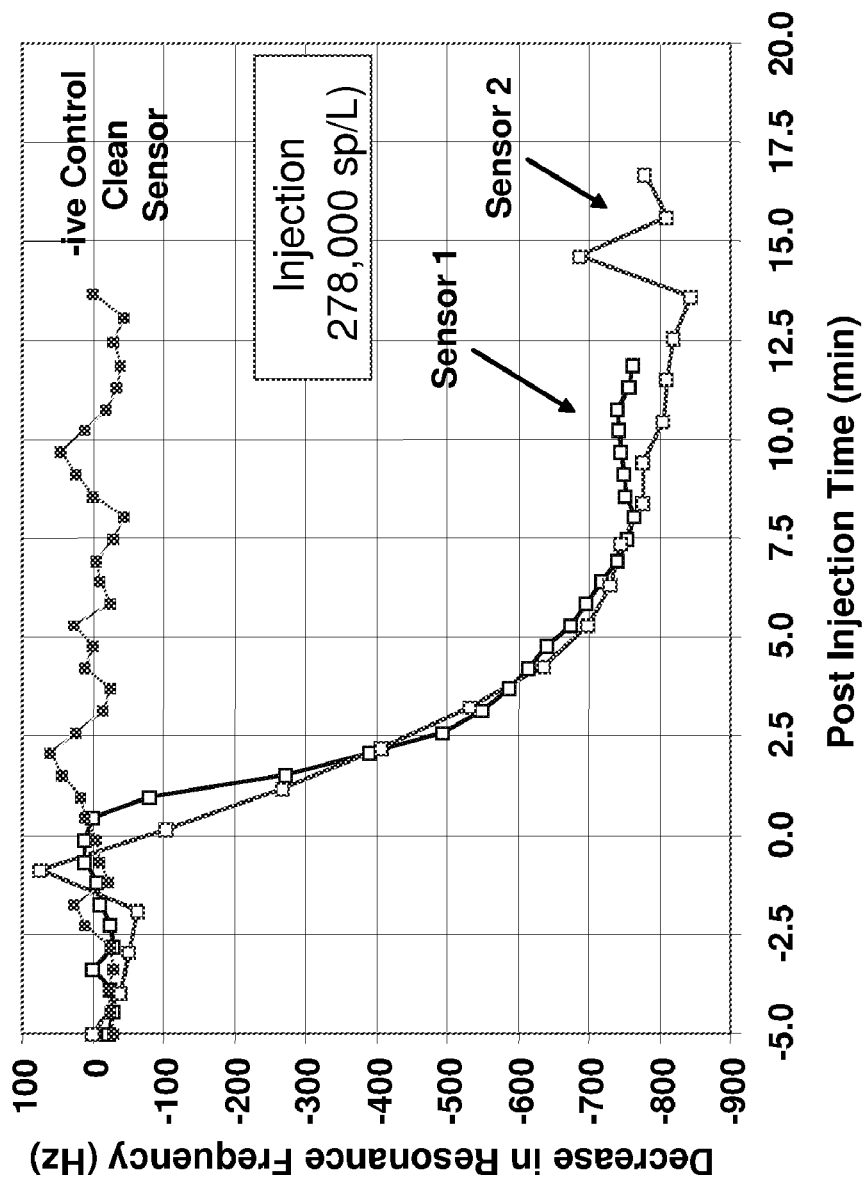
FIG. 30A shows the results of detection experiments for detection of *Bacillus anthracis* in air.

PEMC sensors can have a sensitivity of 10 femtogram depending upon construction and the vibration mode used for detection. For the results of FIG. 30A, two sensors were used. Sensor 1 when exposed to flowing BA spores at concentration of 278,000 spores per Liter of air (Humidity 95%, 24 C), and gave a 760 Hz response. Using the same spore concentration, Sensor 2 gave nearly an identical response of 760 Hz shift. FIG. 30A also shows excellent repeatability between separate runs with different sensors of similar construction when the same mode is used for detection. Thus, successful, quantitative, and repeatable detection of BA spores was observed.

Figure 30B:
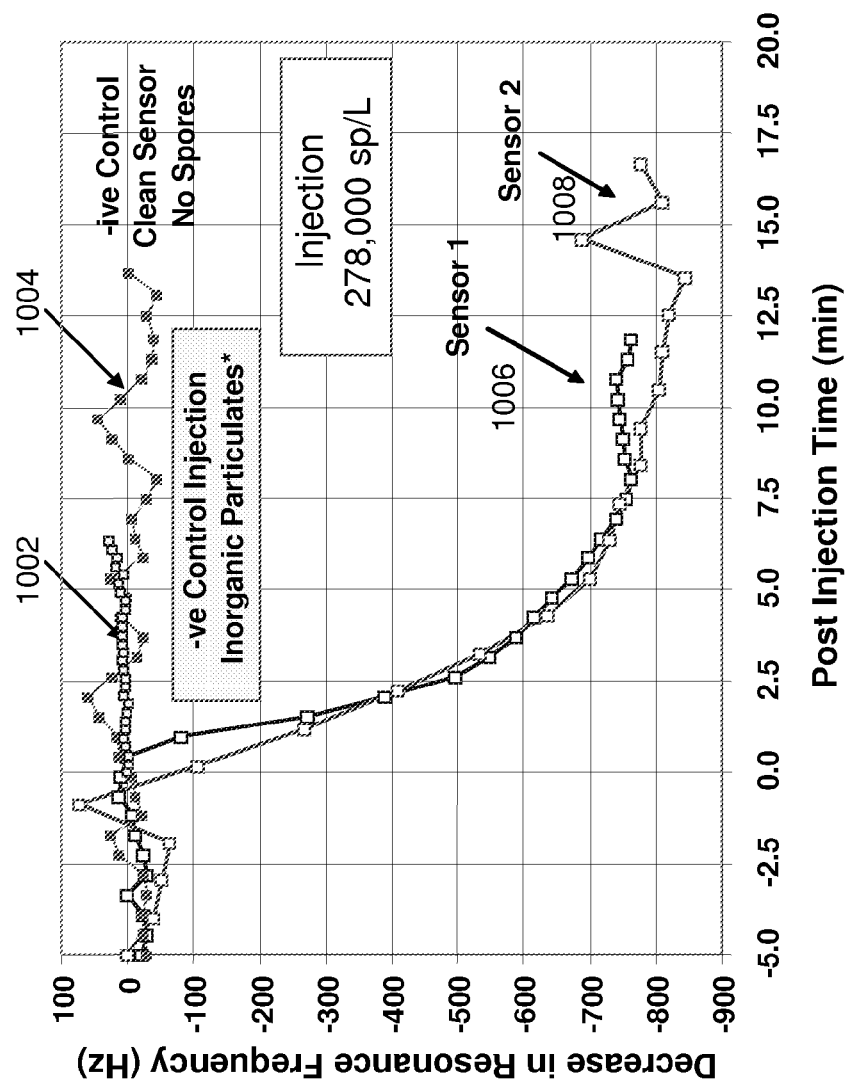
FIG. 30B shows the results of detection experiments for detection of *Bacillus anthracis* in air with a control of inorganic particles.

FIG. 12 B shows the results of exposing four sensors. Sensor 1 (1006) and Sensor 2 (1008) were prepared with a recognition entity that would detect BA spores. Control sensors 1002 and 1004 were likewise prepared with the same recognition entity. FIG. 30B depicts the consistency of results between sensor 1 and sensor 2 in detecting spores in an 278,000 spores per liter gas environment. Sensor plot 1002 depicts a sensor response to a controlled injection of inorganic particulates of aluminum silicate particles in the 0.2 to 0.6 micrometer size. The sensor plot 1002 indicates that there was no substantive response as expected. Sensor plot 1004 depicts a sensor response to a clean air environment. Note that there is no substantive response as expected. This evinces that detection of analytes using the PEMC/PEMCB sensors is very specific to the recognition entity used and that the sensors thus configured are insensitive to non-target substances.

The PEMC sensor responds to changes in mass, temperature and fluid density. Fluctuations in system temperature, humidity (mass and density effects) and pressure (density) can mask the detection of the pathogen. Design of the PEMC sensor minimizes these masking effects. It is noted that the frequency of the PEMC device responded within the time for the spores to travel from the nebulizer to the sensor. The time to detect the BA is on the order of 2 minutes.

As mentioned above, confirmation of the detection of BA attachment to the PEMC sensor was performed by release in low pH buffer. Direct microscopic observation was also used as confirmation. In the low pH buffer confirmation, the ratio of the attachment to the release of 2:1 is consistent with that reported by others for air versus liquid mass change. Confirmation of the BA aerosolization was confirmed via particle size analysis of the nebulizer feed and of the exhaust captured by a air sampler device (SASS 200) in the configuration of FIG. 29A. The SASS 2000 captures approximately 30% of the inlet airborne BA. The results of detection confirmation are given in FIG. 31.

Figure 31:
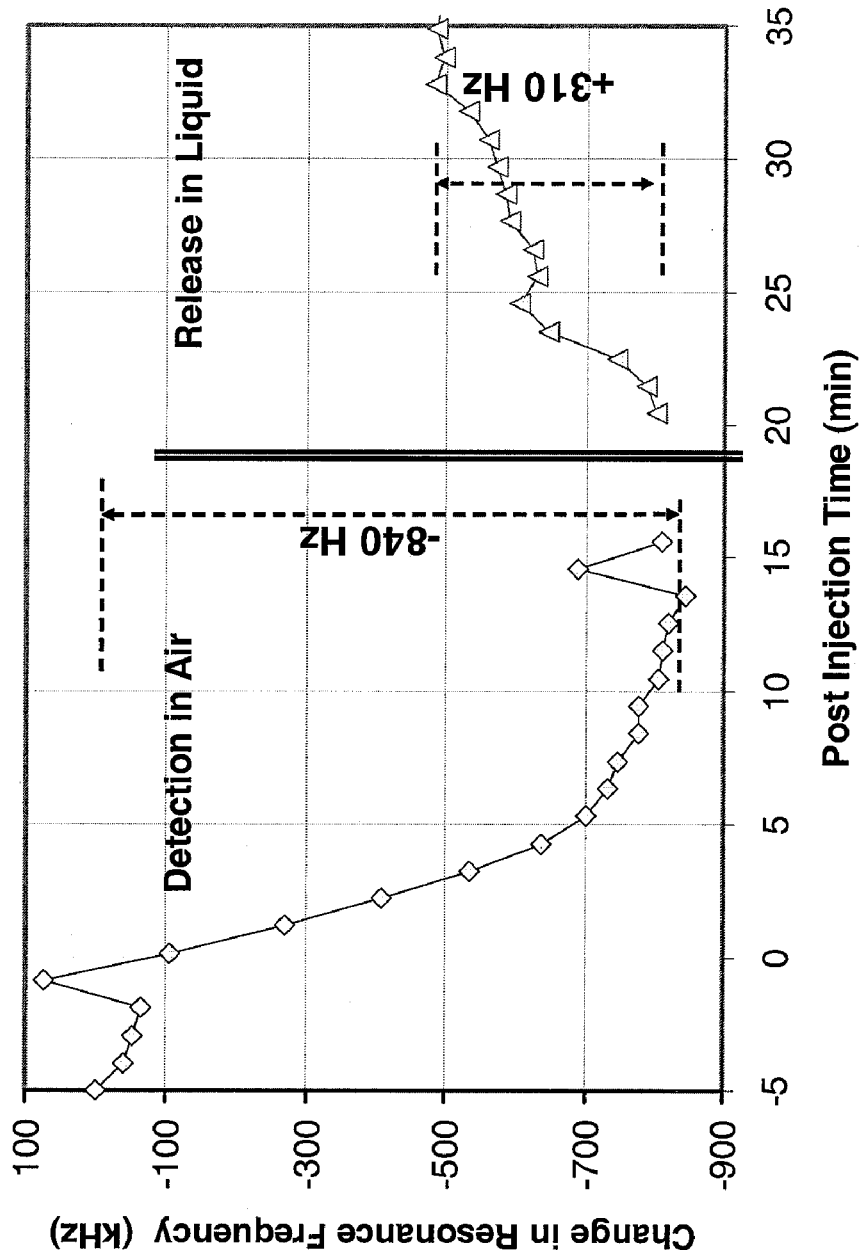
FIG. 31 shows detection confirmation for the experiments of FIG. 30A.

After performing the experiments shown in FIG. 30A, the sensor that was exposed to 278,000 spores per liter of air sample, was inserted in a release buffer (with a pH 2.2) and the resonant frequency was measured. At this pH, the antigen is released from the sensor surface and the reduced mass increases the resonance frequency confirming that the reduction in frequency was indeed due to BA attachment. This confirmation is shown in FIG. 31.

Figure 33:
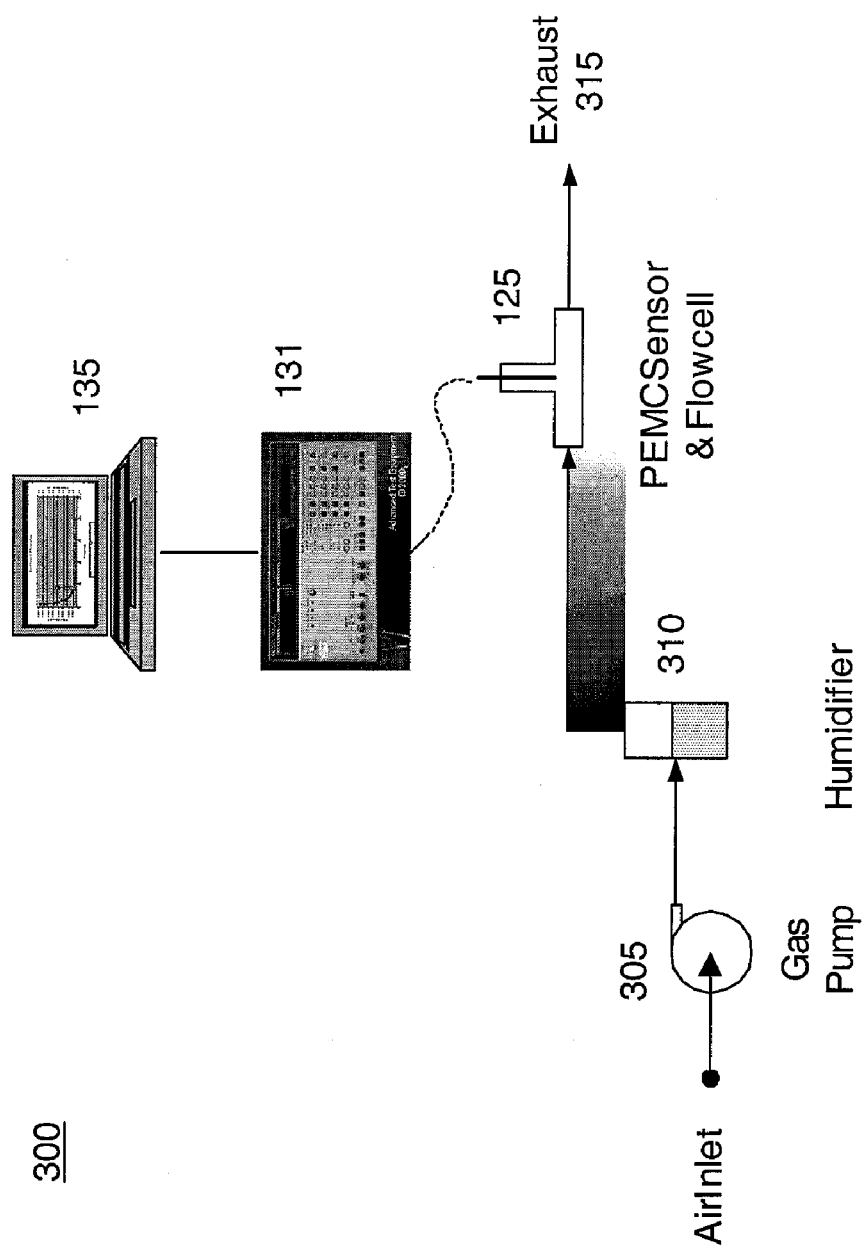
FIG. 33 depicts a humidity infuser aspect of the present invention.

An additional confirmation of the attachment of BA was provided by direct microscopic examination. The scanning electron micrograph of FIG. 33 shows a broken cantilever used in one of the airborne anthrax detection experiments. The sensor was broken to enable mounting on a SEM pedestal mount and was then used for microscopic analysis. The top panel of FIG. 33 shows the presence of anthrax spores used in detection in the region of the sensor surface indicated in the bottom panel. These micrographs show that the anthrax antigen binds to the antibody which is chemically immobilized on the sensor surface.

As noted earlier, since PEMC sensors are vibrating while in contact with the gas stream, only chemical bound attachment can occur thereby reducing or eliminating false positives from gas borne particulate contaminants in an airflow sample. Gas phase experiments were conducted with 0.2 to 6.0 micron clay particles as inert contaminates. It was observed that no change in sensor output was seen from exposure to the contaminants. This also confirms that inert contaminates do not attach to the PEMC surface during operation.

Thus it can see understood and shown by example that the sensors of the present invention may be used for the detection of bioterrorism agents, the detection of airborne pathogens, the detection of markers of TNT such as DNT, the detection of airborne toxins, and the detection of any other target analyte that will bind to suitably prepared PEMC or PEMCB surface. The sensors of the present invention can also be implemented in sensor arrays wherein a plurality of sensors are arranged in a single device for sensing a plurality of different analytes simultaneously. In this manner, the sensors of the present invention can be used, for example, to identify unknown species in a gas, or to indicate the presence of a plurality of different analytes in a gas.

As noted above, detection is affected by humidity. Specifically, very low humidity adversely affects binding affinity. Thus, it is advantageous to include humidification in association with an airborne analyte sensor. FIG. 33 depicts a configuration using the airborne sensor of FIG. 29B. In this embodiment, a gas pump 305 has an air inlet to intake air from an air sample, such as a chamber, a vessel, or a room, and pump the air intake to a humidifier 310. The humidifier 310 adds an amount of humidity to the pumped air so that the PEMC or PEMCB sensor in the flowcell 125 reacts well to target analytes contained in the air intake. The PEMC/PEMCB flowcell 125 then exhausts the air 315 to a safe location. The sensor in the flowcell 125 is measured using an impedance analyzer 131 and a personal computer 135 that collects resonant frequency data from the flowcell. FIG. 33 is simple application of the PEMC/PEMCB sensor in the flowcell for airborne detection of an analyte.

Figure 34:
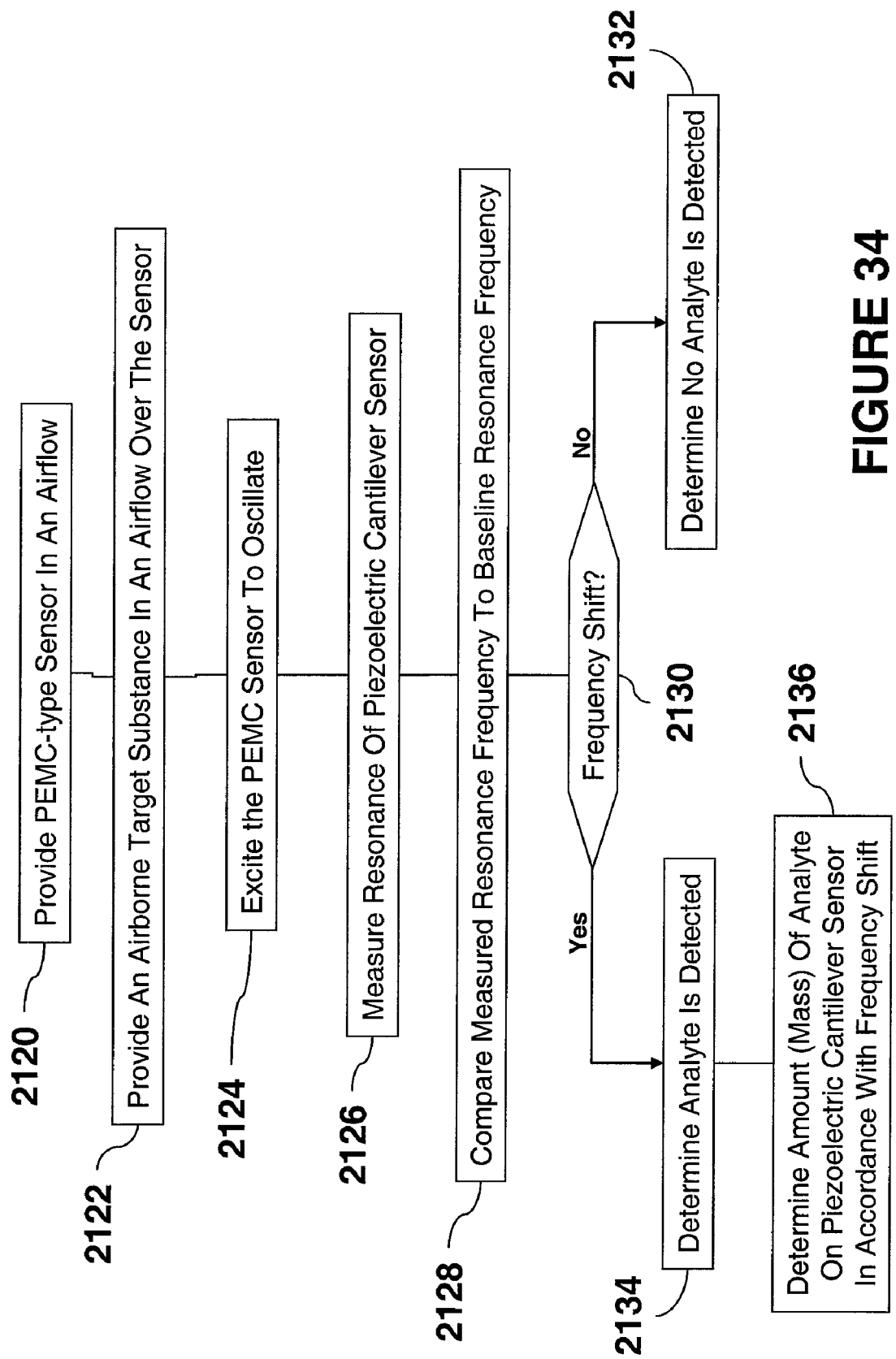
FIG. 34 is a flow diagram of a method of the present invention.

FIG. 34 depicts a flow diagram of a method involving aspects of the invention. The method concerns the detection of an airborne analyte using PEMC-type sensors (including PEMC and PEMCB types). The method starts with providing an PEMC type sensor in step 2120. These sensors can include any of the types shown in FIGS. 19A-19G and variants thereof. These type include the single base cantilever types shown in FIGS. 19A and 19G, the dual base beam type sensors having a non-piezoelectric beam as shown in FIGS. 19B-19D, the beam type sensor having a piezoelectric beam as in FIG. 19F, and the overlapped layer structure shown in FIG. 19E.

Next, an aerosolized target analyte is passed over the sensor in an airflow in step 2122. Here, it is preferable if the recognition entity which attracts the analyte is oriented orthogonally to the airflow having the analyte. Exposure to the airflow allows the recognition entity to capture target analytes. Next, the PEMC sensor is excited via the electrodes into oscillation in step 2124. The oscillation frequency of the cantilever or beam assembly is dependent upon the mass of the assembly which includes the analyte collected by the recognition entity. The oscillation frequency, (i.e. the resonant frequency of the cantilever assembly) of the sensor is measured in step 2126. The measured oscillation frequency of the cantilever assembly is then compared to a natural (resonant) baseline frequency of the cantilever assembly in step 2128. Such comparisons can be made with calculation means that includes a personal computer, an embedded processor, analog or digital circuits, or a hand calculation.

A frequency shift is detected in decision step 2130. If no frequency shift is detected as in step 2132, then a determination is made that no analyte is present on the recognition entity. This may result if the airflow sample is pure or if the recognition entity is not compatible with any analyte within the airflow. If a frequency shift is detected, a determination is made at step 2134 that the target analyte is detected. Further, the specific amount of analyte (i.e. the mass of the analyte deposited on the recognition entity) is determined in step 2136. This step is performed by examining the magnitude of the frequency shift and correlating that magnitude with a mass of the analyte needed to change the resonant frequency of the PEMC sensor. Note that no special preparations were performed as are need in the case of a liquid-based sampling of an analyte. Also, no special concentrating step or enrichment steps are included in the above method as compared to liquid-based analyte detections.

To provide quality control or more accuracy of the detection of an analyte, a comparison, not shown in FIG. 33, is made between a control sensor and the measurement sensor that detects the analyte. For example, a control sensor is preferably identical to the measurement sensor except that the control sensor does not have the recognition entity for the target analyte. When exposed to the same airflow as the measurement sensor, the control sensor resonant frequency change can be differenced from the resonant frequency of the measurement sensor to provide an accurate result.

Additional Sensor Configurations

All of the configurations of FIGS. 35-47 are useful for the construction of sensors which can be used for the detection of analytes in gas or liquid mediums as are the configurations of FIGS. 19A-19G. Thus, the application of the configurations of FIGS. 35-47 is similar to that discussed herein for the detection of airborne chemicals or biologicals. FIGS. 35-47 share some characteristics with those of FIGS. 19A-19G. For example, where indicated, a base element 20 is present where an attachment is made to either a piezoelectric 14 (P) type of element or a non-piezoelectric 16 type of element. The adhesive layer 18 separates a P type layer 14 from a NP type layer 16. FIGS. 35-47 depict electrodes 28 connected to at points 30 to various locations of the piezoelectric 14 type of element for excitation of the cantilever structure or beam structure. FIGS.

35-47 indicate the wide range of configurations that can be implemented with PEMC and PEMCB devices. A brief description of each follows.

Figure 35:
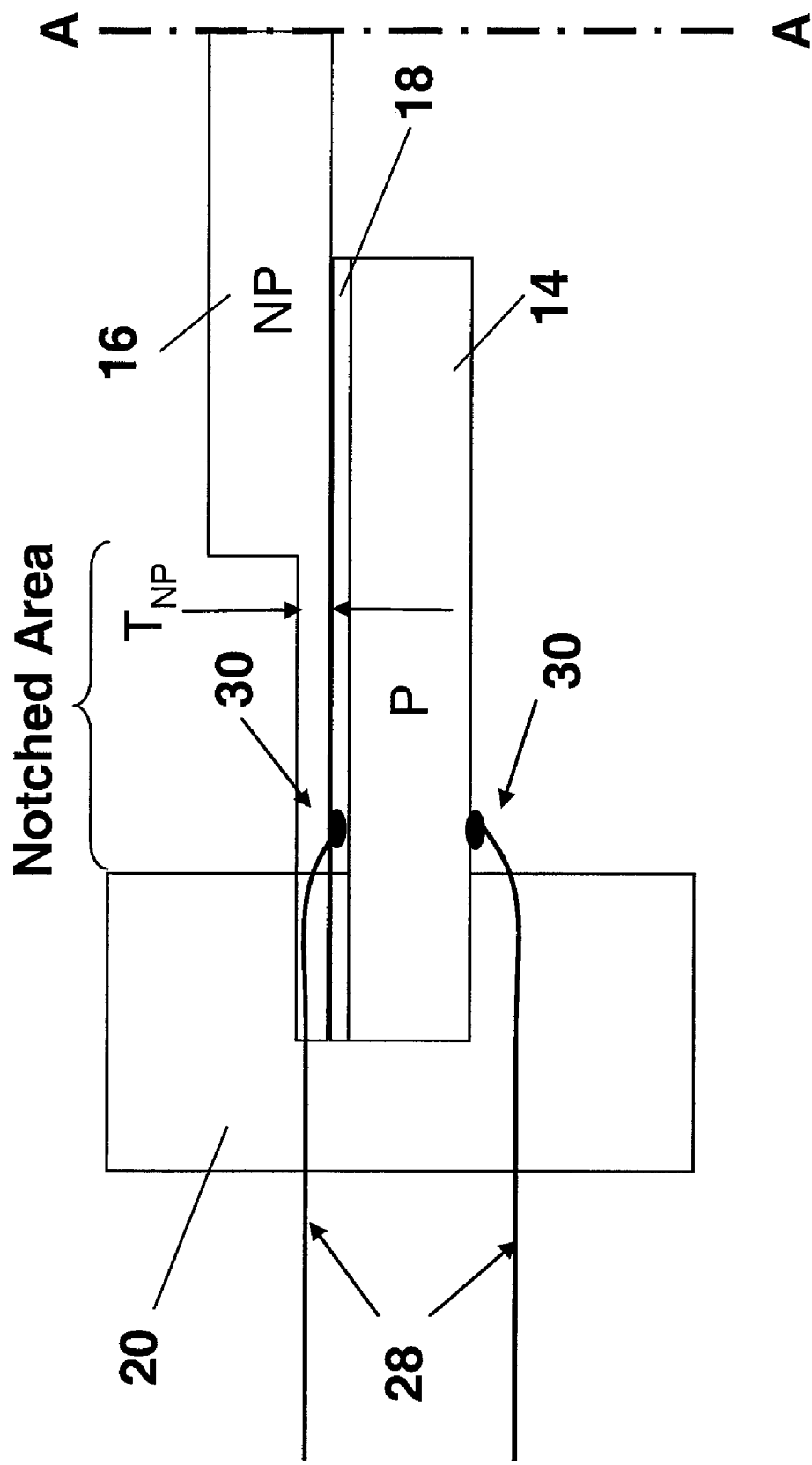
FIG. 35 is a notched configuration for a sensor.

FIG. 35 depicts a configuration of a PEMC or PEMCB sensor where the NP section 16 is contiguous with P section 14. The thickness of the NP layer 16 ($T_{Np}$) can vary along length of the NP layer 14 and $T_{NP}$ can be designed to support a sensitive sensor. In this configuration, the modulus of bending is in the NP layer 14 notched area is less than that of the thicker portion of the NP layer 14. Although only a free-end cantilever arm comprising a P and NP layer are shown, the configuration of FIG. 35 may be duplicated in mirror form about the center line A-A. This mirror duplication of FIG. 35 depicts a symmetry for a beam type (PEMCB) sensor. There are several instances of a centerline depiction in FIGS. 35-47 where the geometry depiction can be either a free-end cantilever or a beam type configuration of sensor. In addition, all of the basic information about electrode wire 28 and contact 30 placement and the width of the notch applies to this configuration and to all others.

Figure 36:
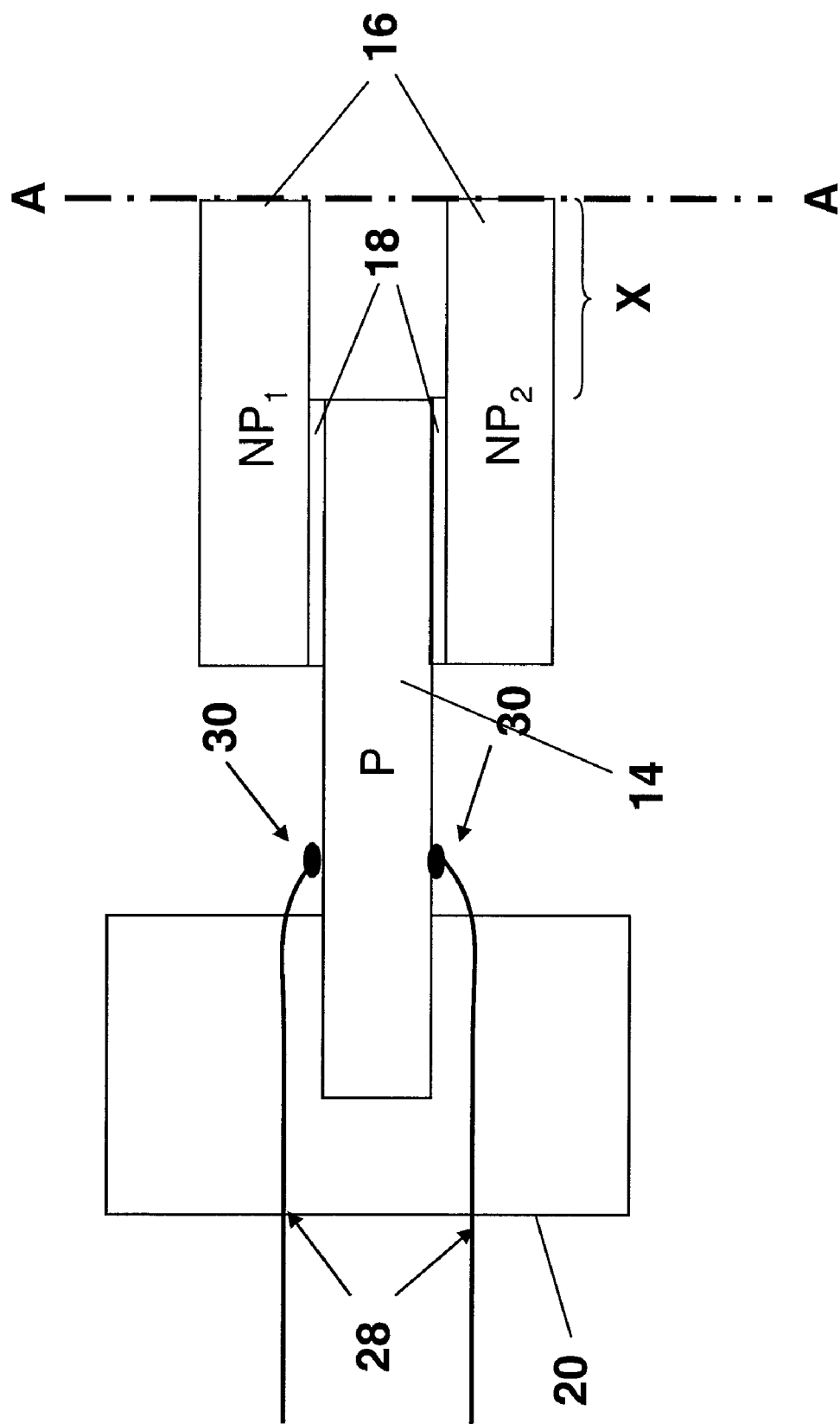
FIG. 36 is a sandwiched configuration for a sensor.
Figure 37:
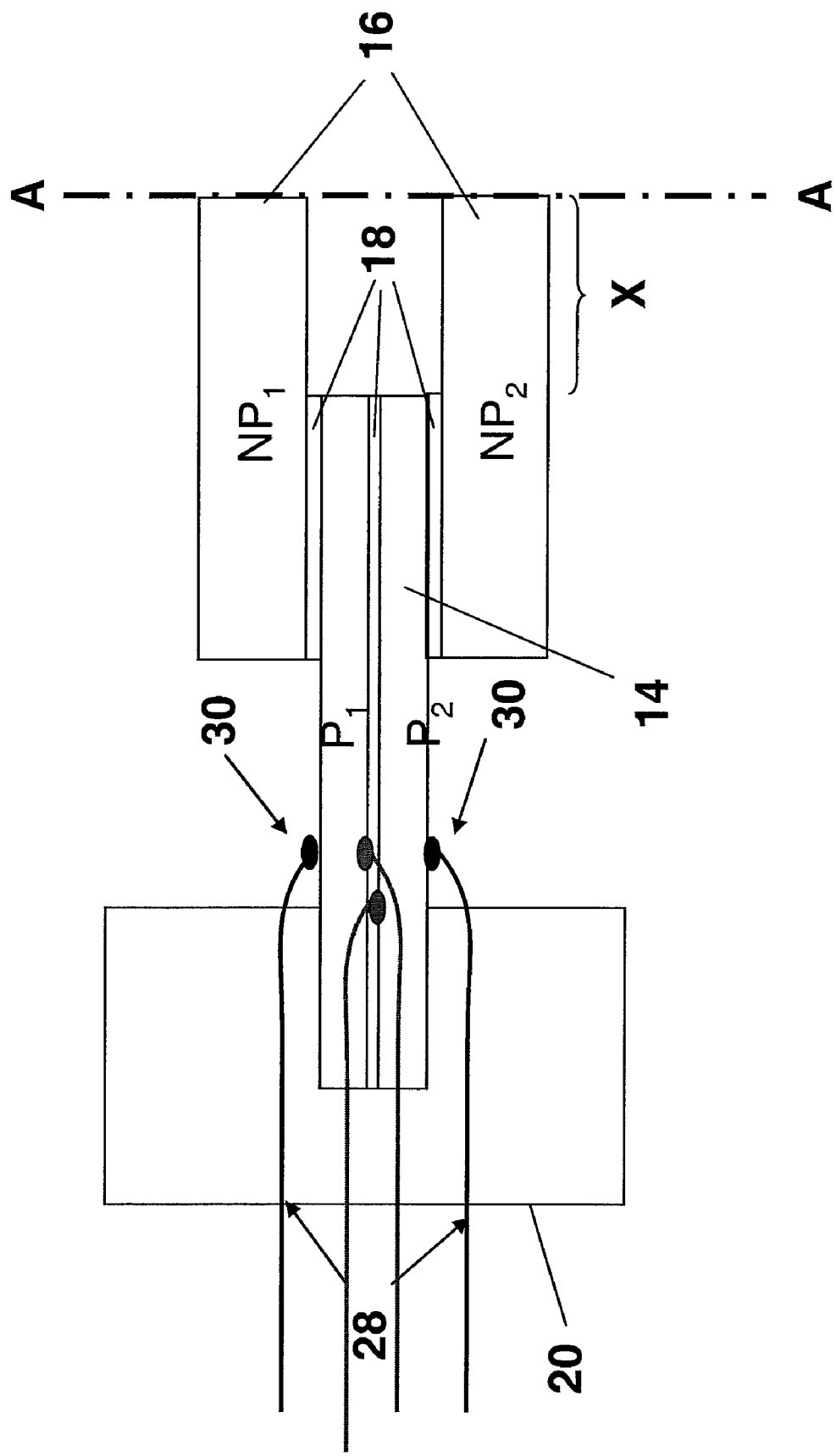
FIG. 37 is an alternative sandwiched configuration for a sensor.

FIG. 36 depicts two layers of NP 16; one at the top and one at the bottom, which can be used effectively if the Bending Modulus (EI) of NP1 is not equal to that of NP2 Here, the designations NP1 and NP2 on FIG. 36 indicate that the two NP layers may differ in geometry as well as material. For example, NP1 can be smaller or a different shape than NP2. Also NP1 can be made of glass whereas NP2 is made of ceramic. As in FIG. 35, the minor image around centerline A-A would create a beam configuration. In this case, the distance X is greater than or equal to 0, meaning that P can be contiguous to the minor anchor or it could be two separate pieces. In the case where X>0, you could excite one or BOTH pieces of P but in the later case the two excitations could be synchronized. FIG. 37 depicts a configuration similar to FIG. 36 except for two aspects. In FIG. 36, NP1=NP2 because having P1 and P2 creates an axis of symmetry. The minor image around A-A creates a beam configuration. In this case, X is greater than or equal to zero. This means that P can be contiguous to the mirror anchor OR it could be two separate pieces. In the case where X>0, you could excite one or both pieces of P but in the later case, the two excitations would preferably be synchronized.

Figure 38:
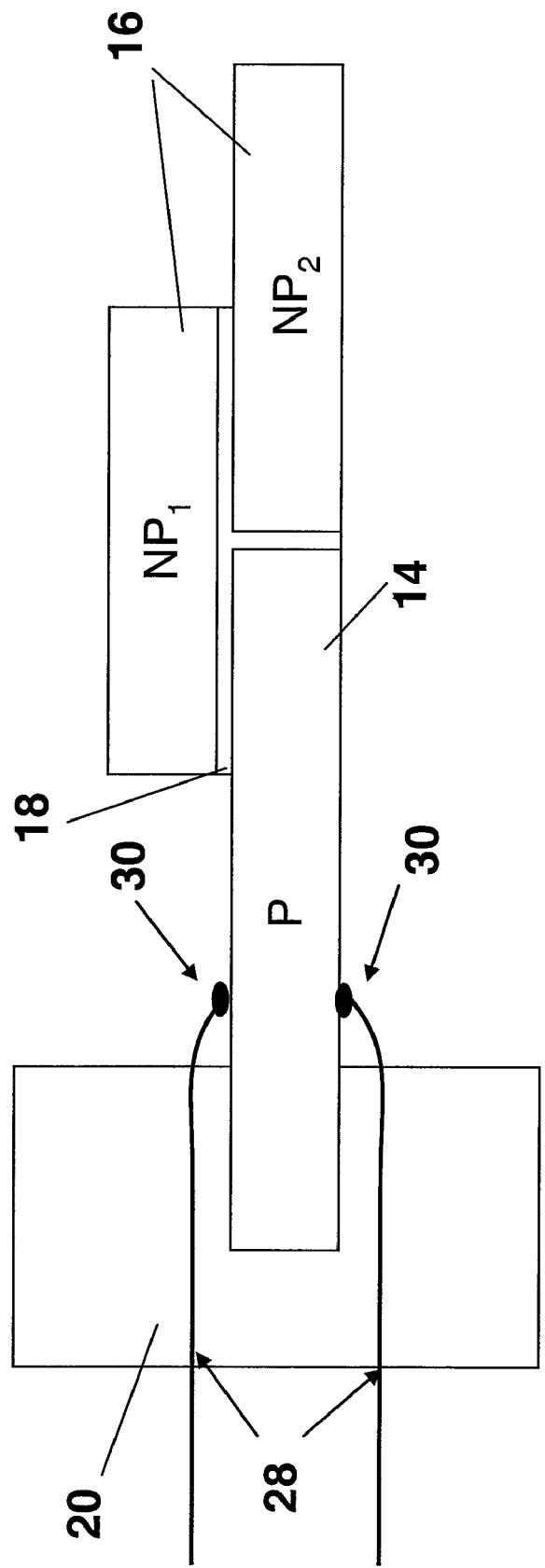
FIG. 38 is an alternative to FIG. 19A for a sensor geometry.

FIG. 38 depicts a configuration similar to FIG. 19A with the exception of an additional piece of NP 16 type material. The advantage of this structure over FIG. 19A is that more control over the position of the resonant frequency peak may be achieved and the configuration can be effective in dampening unwanted modes. NP1 16 can be equal or unequal to NP2 16 depending on the desired properties. The free-end cantilever configuration of FIG. 38 could be converted to a beam configuration by simply fixing the distal end of NP2 into a base element. Note also, that the portion labeled NP2 in FIG. 38 could be created simply by removing the electrodes (laser ablation, chemical etching, etc.) from a section of P type material and using an unexcitable portion of P type material.

Figure 39:
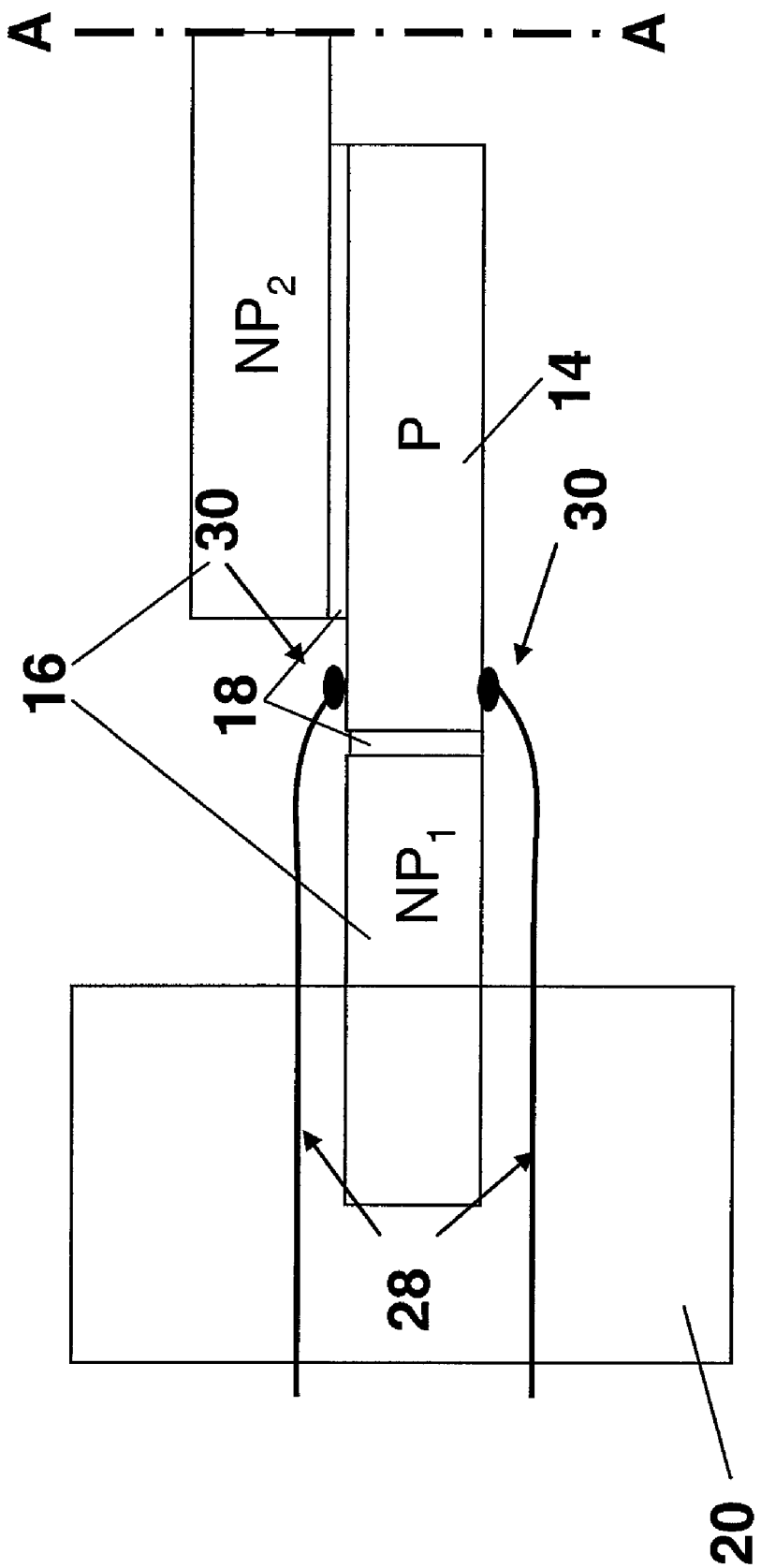
FIG. 39 is another alternative configuration for FIG. 19A of a sensor.

FIG. 39 depicts a configuration similar to FIG. 19A with the exception of the addition of NP1. Here, NP1 connects to base 20 instead of a P type of layer. This configuration offers an improved signal because, unlike the FIG. 19A configuration, the proximal end of P is not constrained so that some of its signal energy is not dissipated thereby generating a larger signal. Stated differently, some of the signal energy from FIG. 19A may be lost because the proximal end is constrained. The configuration of FIG. 39 represents an improvement over that of FIG. 19A. As in the configurations of FIGS. 35-37, a beam configuration can be created by adding the mirror image around centerline A-A.

Figure 40:
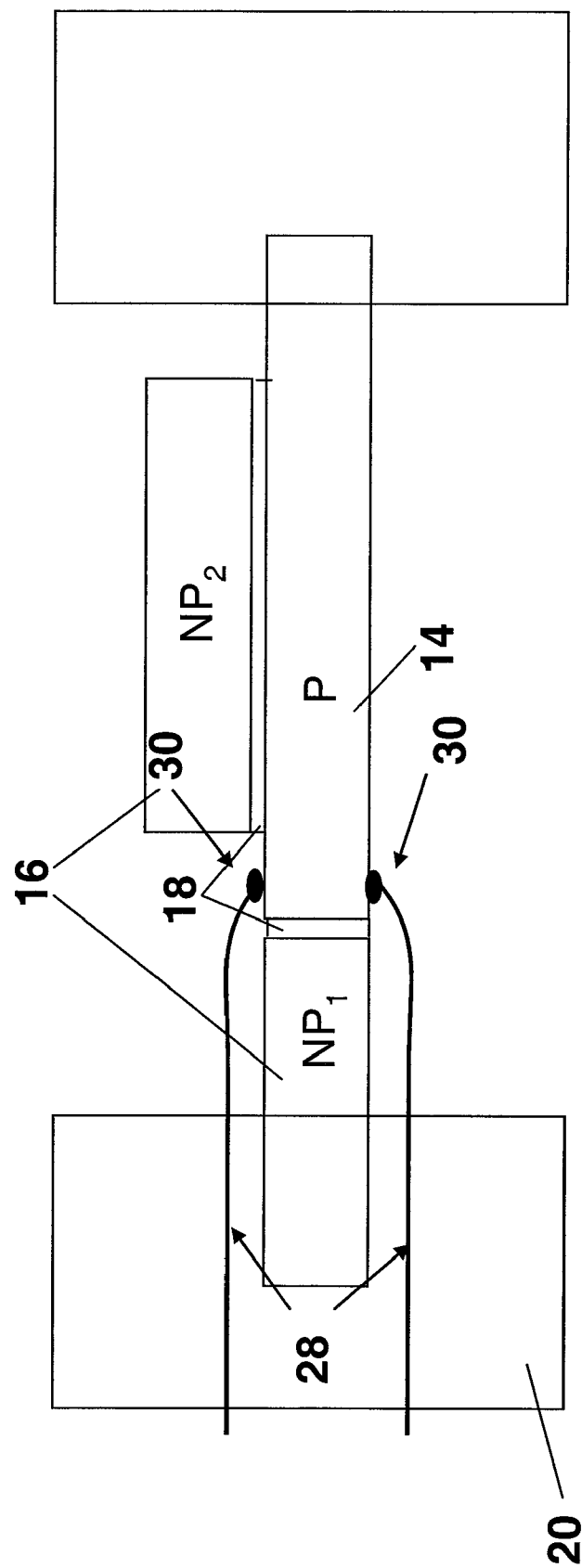
FIG. 40 is beam type configuration of FIG. 19F.
Figure 41:
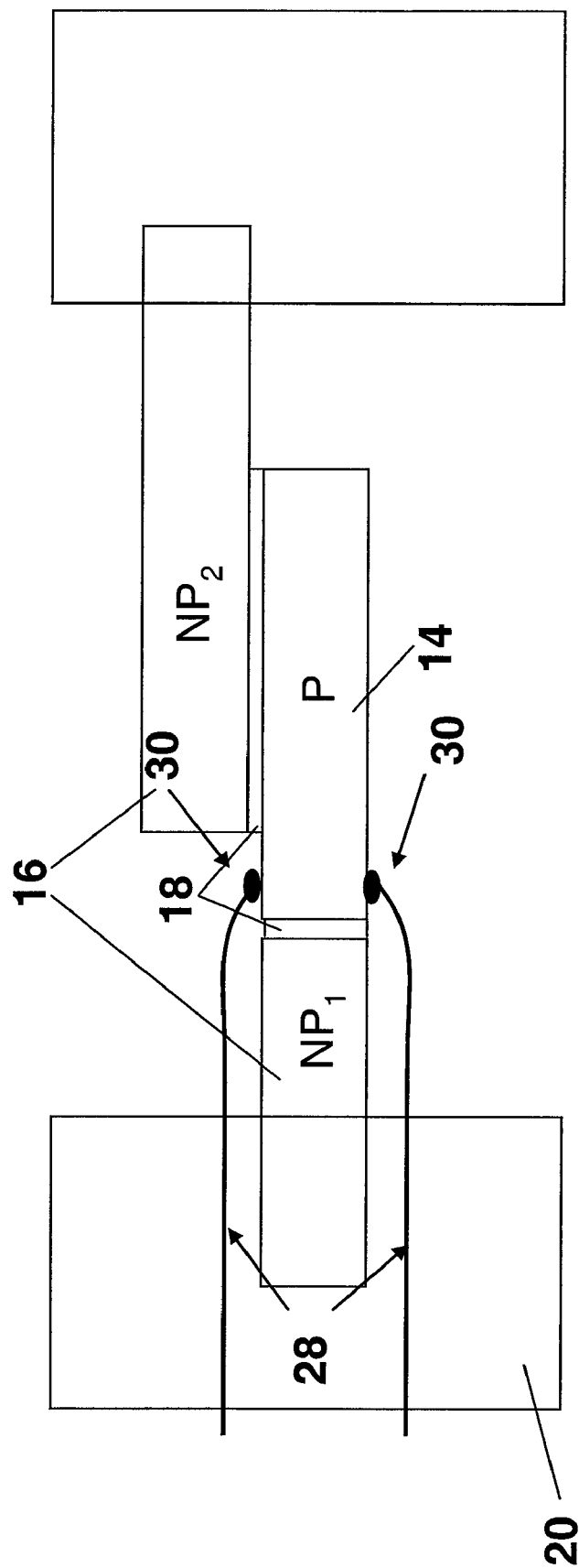
FIG. 41 is an alternative configuration of FIG. 19E.
Figure 42:
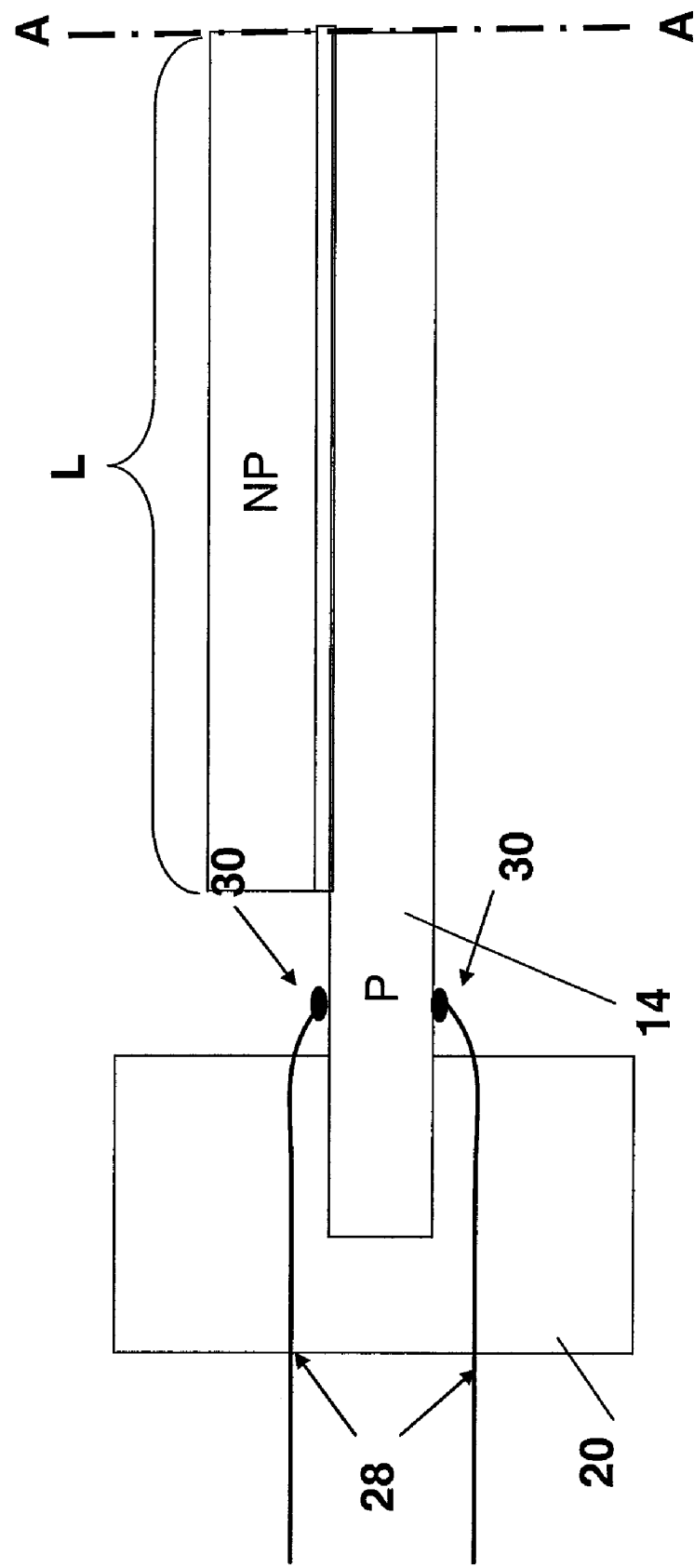
FIG. 42 is an alternative configuration of FIG. 19G.
Figure 43:
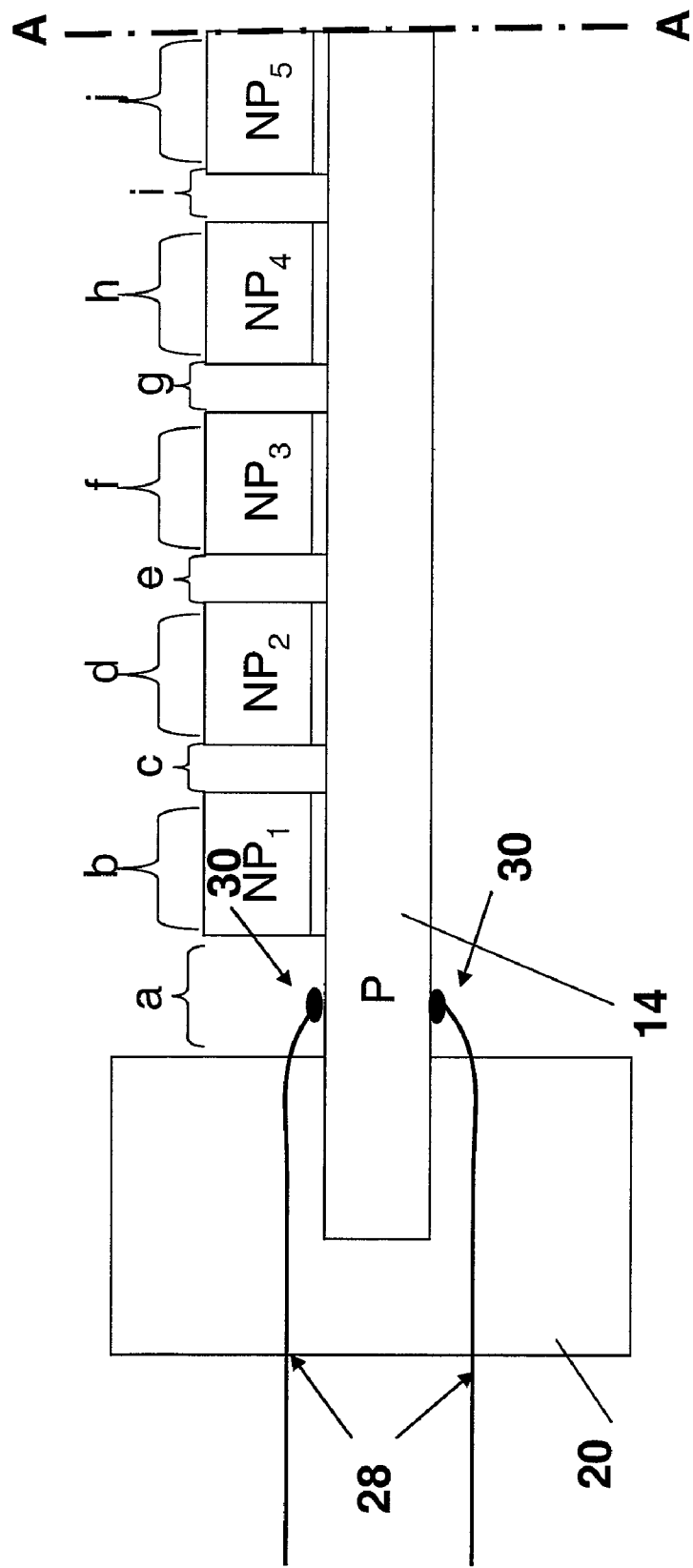
FIG. 43 is an alternative configuration of FIG. 42.

FIG. 40 depicts a configuration similar to the structure of FIG. 19F with the exception of the addition of the reversal of the P and NP regions and the addition of the P type of layer 14. This configuration may offer an improved signal because the proximal end of P is not constrained such some of its signal energy may not be dissipated. Thus, a larger signal is generated. FIG. 41 depicts a configuration similar to that of FIG. 19E with the exception of the addition of NP1. This configuration may offer an improved signal because the proximal end of P is not constrained such some of its signal energy may not be dissipated. Thus, a larger signal is generated. FIG. 42 depicts a configuration similar to FIG. 19G with the exception that the Bending Modulus (EI) of the NP layer varies as a function of the length L. By varying this parameter, an enhancement in sensitivity by increasing the stress concentrated at the position of the electrodes is achieved. One practical way to achieve this would be as shown in FIG. 43 where the NP layer is composed of multiple discrete segments which can vary in width along with adjacent sections that are empty space or an alternate material of a lower modulus. A beam configuration is created by adding the mirror image around A-A in either of FIG. 42 or 43.

Figure 44:
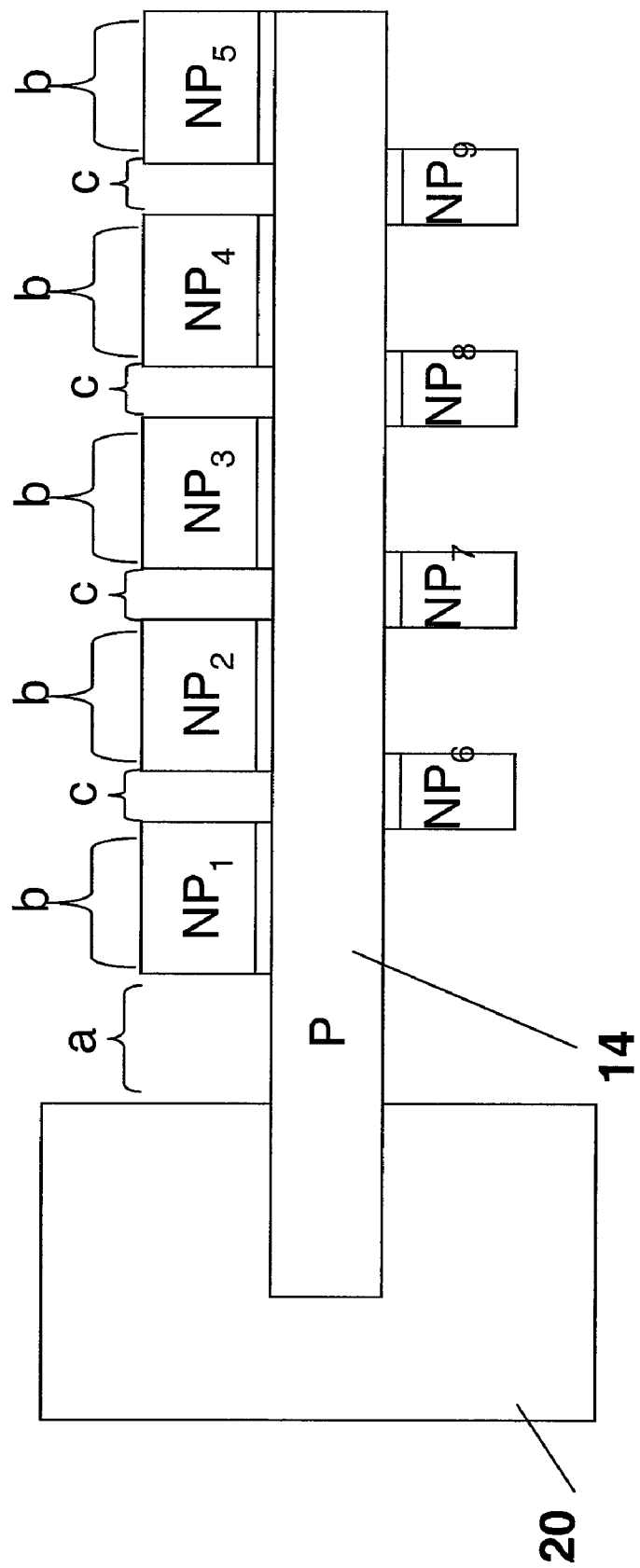
FIG. 44 is an alternative configuration of FIG. 36.
Figure 45:
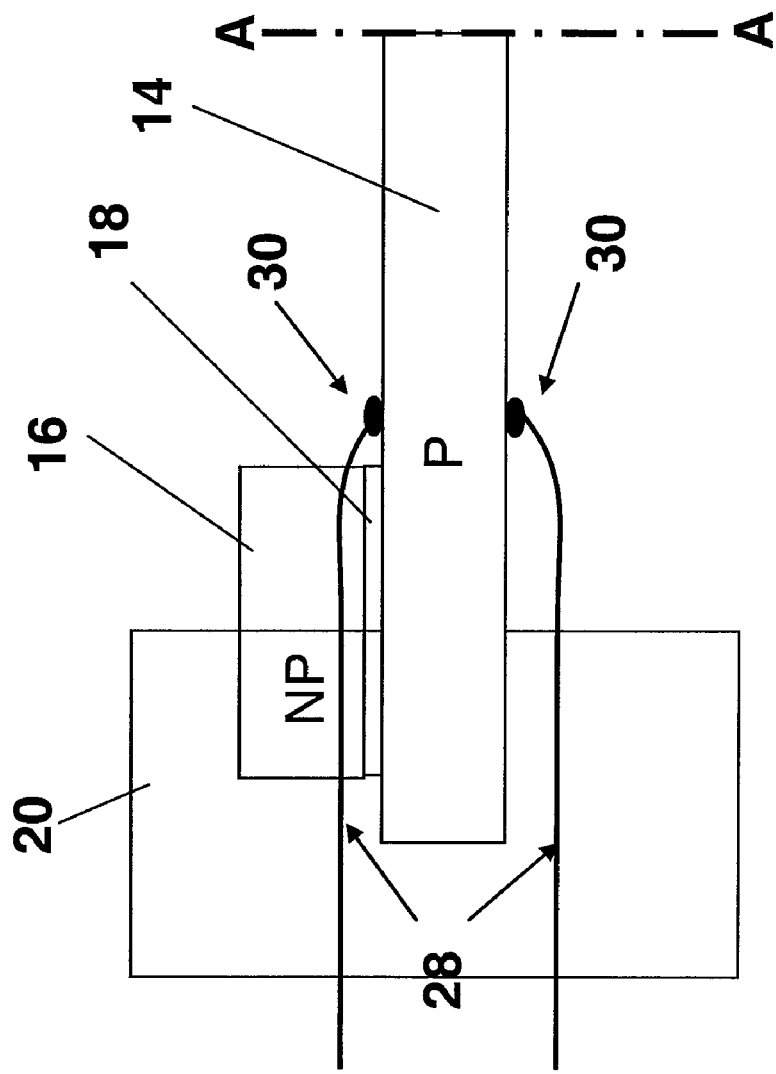
FIG. 45 is a multiple layered sensor configuration where the layers are at least partially anchored in a base.
Figure 46:
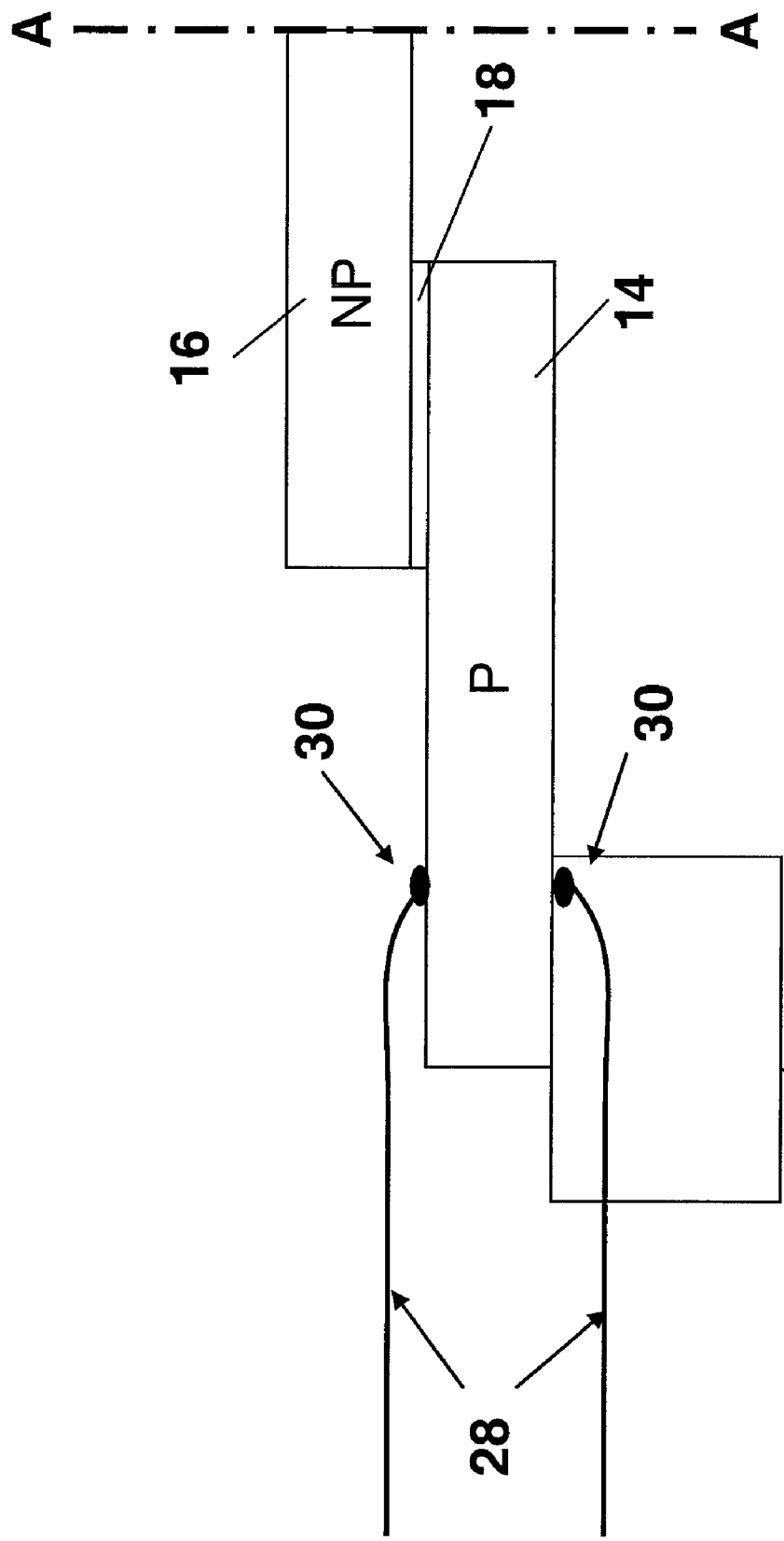
FIG. 46 is a configuration having an modified base.

FIG. 44 is a configuration that is similar to FIG. 36 except that the top NP layer has a Bending Modulus (EI) that varies as a function of length and a bottom layer that varies as a function of length. This is effectively the mirror image of FIG. 43 but where the bottom layer is different than the top layer to create a resonant structure. In FIG. 44, the top and bottom layers could be identical, but only if the P layer were a sandwich construction as shown in FIG. 37. FIG. 45 is a configuration that concentrates stress sufficiently at the point of the electrodes to create a sensitive response. However, it gives a more stable response due to the position of NP 16. A beam can structure can be created by minoring around the A-A centerline. FIG. 46 is a configuration that is useful for manufacturability because of the abbreviated base 20. However, it provides more unwanted vibration modes. A beam structure is created by mirroring about the A-A centerline.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed:
1. A method for detection of an airborne target analyte comprising the steps of:
  providing a millimeter-sized sensor comprising;
    a piezoelectric layer having a first end and a second end, the first end proximate to and attached to a first base;
    a non-piezoelectric layer having a first end and a second end, wherein:
    a portion of the non-piezoelectric layer overlaps and is attached to the piezoelectric layer; and
    the base is not attached to the non-piezoelectric layer;
      a recognition entity associated with the non-piezoelectric layer, wherein the combination of the piezoelectric layer, the non-piezoelectric layer, and the recognition entity comprising a cantilever portion; and electrodes operatively attached to the piezoelectric layer, wherein electrical stimulation from the electrodes causes the cantilever portion to oscillate;

mounting the millimeter-sized sensor in an airflow;

exposing the recognition entity of the cantilever to the target analyte in the airflow;

measuring an oscillation frequency of the cantilever; and comparing the measured oscillation frequency to a baseline oscillation frequency to determine a frequency shift indicative of a presence of the target analyte on the recognition entity.

2. The method of claim 1, wherein providing a millimeter-sized sensor further includes providing a sensor wherein the piezoelectric layer comprises both piezoelectric and non-piezoelectric portions arranged linearly.

3. The method of claim 1, wherein providing a millimeter-sized sensor further includes providing a sensor wherein the piezoelectric layer comprises two piezoelectric layers separated by an adhesive.

4. The method of claim 1, wherein providing a millimeter-sized sensor further includes providing a sensor wherein the non-piezoelectric layer comprises a plurality of linearly arranged and spaced non-piezoelectric portions.

5. The method of claim 1, further comprising:
determining an amount of the target analyte present on the recognition entity.

6. The method of claim 1, wherein providing a millimeter-sized sensor further comprises providing the millimeter-sized sensor wherein the recognition entity is selected from one of the group consisting of antibodies, DNA molecules, aptamers, phage and biochemical reagents and wherein the selection is one of the group consisting of naturally and synthetically constituted.

7. The method of claim 6, wherein the recognition entity is an antibody that recognizes and binds the airborne analyte.

8. The method of claim 7, wherein the airborne analyte is chemically immobilized on the cantilever sensor surface by binding with the antibody.

9. The method of claim 1, wherein exposing the recognition entity of the cantilever to the target analyte in the airflow comprises exposing the recognition entity to one of the group consisting of a biological substance and a chemical substance in the airflow.

10. The method of claim 9, wherein the biological substance is a *Bacillus anthracis* spore.

11. The method of claim 1, further comprising:
providing a plurality of millimeter-sized sensors in a sensor array, wherein each of the plurality of millimeter sized sensors in the array is exposed to the airflow to detect one at least one analyte.

12. The method of claim 11, wherein the at least one analyte is detected by measuring a plurality of frequency shifts, one frequency shift for each provided millimeter-sized sensor.

13. The method of claim 1, wherein mounting the millimeter-sized sensor in an airflow comprises mounting the millimeter-sized sensor substantially orthogonal to the airflow.

14. The method of claim 13, wherein the airflow is in the range of 0.01 to 10 meters/second.

15. The method of claim 1, wherein exposing the recognition entity of the cantilever to the target analyte in the airflow comprises exposing the recognition entity to the target analyte without collecting the target analyte in a liquid medium.

16. The method of claim 1, wherein measuring an oscillation frequency of the cantilever comprises measuring a resonant frequency at which the cantilever oscillates after exposure to the target analyte.

17. The method of claim 1, wherein providing a millimeter-sized sensor comprises providing a millimeter-sized sensor wherein the second end of the non-piezoelectric layer is attached to a second base.

18. A method for detection of an airborne target analyte comprising the steps of:
providing a millimeter-sized sensor comprising;
a first non-piezoelectric layer having a first end and a second end, the first end proximate to and attached to a base;
a piezoelectric layer having a first end and a second end, wherein:
a portion of the piezoelectric layer is attached to the first non-piezoelectric layer in a linear arrangement; and
the base is not attached to the non-piezoelectric layer;
a recognition entity associated with a second non-piezoelectric layer, wherein the second non-piezoelectric layer overlaps and is attached to the piezoelectric layer, wherein the combination of the piezoelectric layer, the first and second non-piezoelectric layers, and the recognition entity comprises a cantilever portion; and
electrodes operatively attached to the piezoelectric layer, wherein electrical stimulation from the electrodes causes the cantilever portion to oscillate;
mounting the millimeter-sized sensor in an airflow;
exposing the recognition entity of the cantilever to the target analyte in the airflow;
measuring an oscillation frequency of the cantilever; and
comparing the measured oscillation frequency to a baseline oscillation frequency to determine a frequency shift indicative of a presence of the target analyte on the recognition entity.

19. An apparatus for detecting an airborne target analyte, the apparatus comprising:
a millimeter-sized sensor comprising;
a first layer having a first end and a second end, the first end proximate to and attached to a first base;
a second layer having a first end and a second end, wherein a portion of the second layer overlaps and is attached to the first layer with an adhesive, and wherein the first layer is selected from the group consisting of a piezoelectric material and a non-piezoelectric material and the second layer is a different material from the first layer;
and further wherein,
the first base is not attached to the non-piezoelectric material layer;
a recognition entity associated with the second layer, wherein the combination of the first layer, the second layer, and the recognition entity comprising a cantilever portion; and
electrodes operatively attached to the piezoelectric material, wherein electrical stimulation from the electrodes causes the cantilever portion to oscillate;
an exposure tube assembly comprising the millimeter-sized sensor;
a nebulizer to aerosolize the target analyte;
an air supply feeding the nebulizer, the air supply also used to pass the aerosolized target analyte into the exposure tube assembly;
an analyzer that collects resonant frequency data from the millimeter sized sensor, wherein the analyzer compares the measured resonant frequency of the millimeter-sized sensor to a baseline resonant frequency to determine a frequency change, the frequency change indicating an amount of mass of the target analyte collected on the recognition entity of the millimeter-sized sensor.

20. The apparatus of claim 19, further comprising an array of millimeter-sized sensors, each sensor in the array providing frequency information to the analyzer for a determination of the presence and amount of at least one analyte.

21. The apparatus of claim 19, where the analyte is a *Bacillus anthracis* spore.

22. An apparatus for detection of a target analyte, the apparatus comprising:

a piezoelectric layer having a first end and a second end, the first end proximate to and attached to a first base;

a non-piezoelectric layer having a first end and a second end, wherein a portion of the non-piezoelectric layer overlaps and is attached to the piezoelectric layer;

and the base is not attached to the non-piezoelectric layer;

a recognition entity associated with the non-piezoelectric layer, wherein the combination of the piezoelectric layer, the non-piezoelectric layer, and the recognition entity comprises a cantilever portion; and electrodes operatively attached to the piezoelectric layer, wherein electrical stimulation from the electrodes causes the cantilever portion to oscillate.

23. The apparatus of claim 22, wherein the piezoelectric layer further comprises both piezoelectric and non-piezoelectric portions arranged linearly.

24. The apparatus of claim 22, wherein the piezoelectric layer further comprises two piezoelectric layers separated by an adhesive.

25. The apparatus of claim 22, wherein the non-piezoelectric layer further comprises a plurality of linearly arranged and spaced non-piezoelectric portions.

26. An apparatus for detection of a target analyte, the apparatus comprising:

a first non-piezoelectric layer having a first end and a second end, the first end proximate to and attached to a base;

a piezoelectric layer having a first end and a second end, wherein a portion of the piezoelectric layer is attached to the first non-piezoelectric layer in a linear arrangement, wherein the base is not attached to the non-piezoelectric layer;

a recognition entity associated with a second non-piezoelectric layer, wherein the second non-piezoelectric layer overlaps and is attached to the piezoelectric layer, wherein the combination of the piezoelectric layer, the first and second non-piezoelectric layers, and the recognition entity comprises a cantilever portion; and electrodes operatively attached to the piezoelectric layer, wherein electrical stimulation from the electrodes causes the cantilever portion to oscillate.

27. An apparatus for detection of a target analyte, the apparatus comprising:

a millimeter-sized sensor comprising:

a base;

a piezoelectric layer attached to the base at a proximate end of the piezoelectric layer;

a non-piezoelectric layer attached to a distal portion of the piezoelectric layer, wherein the base is not attached to the non-piezoelectric layer;

electrodes operatively attached to the piezoelectric layer, wherein electrical excitation of the electrodes causes a mechanical oscillation in the piezoelectric layer, wherein oscillations at resonance subject the sensor to higher stress levels than oscillations at non-resonance; and wherein enhanced detection of the target analyte is achieved by varying a bending modulus of the sensor to enhance stress and electrical impedance at a point of electrode attachment.

* * * * *